(12) United States Patent
Follini et al.

(10) Patent No.: US 12,419,668 B2
(45) Date of Patent: Sep. 23, 2025

(54) ROD COUPLING ASSEMBLIES FOR BONE STABILIZATION CONSTRUCTS

(71) Applicant: SI-BONE INC., Santa Clara, CA (US)

(72) Inventors: Francois Follini, Santa Clara, CA (US); Derek P. Lindsey, San Jose, CA (US); Bret Schneider, San Jose, CA (US)

(73) Assignee: SI-Bone Inc., Santa Clara, CA (US)

( * ) Notice: Subject to any disclaimer, the term of this patent is extended or adjusted under 35 U.S.C. 154(b) by 320 days.

(21) Appl. No.: 17/777,679

(22) PCT Filed: Nov. 23, 2020

(86) PCT No.: PCT/US2020/061849
§ 371 (c)(1),
(2) Date: May 18, 2022

(87) PCT Pub. No.: WO2021/102429
PCT Pub. Date: May 27, 2021

(65) Prior Publication Data
US 2023/0000526 A1    Jan. 5, 2023

Related U.S. Application Data

(60) Provisional application No. 62/938,546, filed on Nov. 21, 2019.

(51) Int. Cl.
*A61B 17/70* (2006.01)
(52) U.S. Cl.
CPC ...... *A61B 17/7037* (2013.01); *A61B 17/7032* (2013.01); *A61B 17/7098* (2013.01)

(58) Field of Classification Search
CPC ............ A61B 17/7032; A61B 17/7034; A61B 17/7035; A61B 17/7037; A61B 17/7044; A61B 17/7076
See application file for complete search history.

(56) References Cited

U.S. PATENT DOCUMENTS

| | | |
|---|---|---|
| 1,951,278 A | 3/1934 | Ericsson |
| 2,136,471 A | 11/1938 | Schneider |
| 2,243,717 A | 5/1941 | Moreira |
| 2,414,882 A | 1/1947 | Longfellow |
| 2,562,419 A | 7/1951 | Ferris |

(Continued)

FOREIGN PATENT DOCUMENTS

| | | |
|---|---|---|
| CN | 1128944 A | 8/1996 |
| CN | 1190882 A | 8/1998 |

(Continued)

OTHER PUBLICATIONS

Acumed; Acutrak Headless Compressioin Screw (product information); 12 pgs; © 2005; retrieved Sep. 25, 2014 from http://www.rcsed.ac.uk/fellows/lvanrensburg/classification/surgtech/acumed/manuals/acutrak-brochure%200311.pdf.

(Continued)

*Primary Examiner* — Larry E Waggle, Jr.
(74) *Attorney, Agent, or Firm* — Shay Glenn LLP

(57) ABSTRACT

Bone implants and stabilizing rod coupling assemblies to secure a stabilizing rod relative to the bone implant. Bone implants may include a radially recessed collet receiving region that includes a proximal end with an undercut ledge configuration that is sized and configured to interface with and couple to a collet of a tulip assembly.

17 Claims, 36 Drawing Sheets

(56) References Cited

U.S. PATENT DOCUMENTS

| | | |
|---|---|---|
| 2,675,801 A | 4/1954 | Bambara et al. |
| 2,697,433 A | 12/1954 | Zehnder |
| 3,076,453 A | 2/1963 | Tronzo |
| 3,506,982 A | 4/1970 | Steffee |
| 3,694,821 A | 10/1972 | Moritz |
| 3,709,218 A | 1/1973 | Halloran |
| 3,744,488 A | 7/1973 | Cox |
| 4,059,115 A | 11/1977 | Jumashev et al. |
| 4,156,943 A | 6/1979 | Collier |
| 4,197,645 A | 4/1980 | Scheicher |
| 4,292,964 A | 10/1981 | Ulrich |
| 4,341,206 A | 7/1982 | Perrett et al. |
| 4,344,190 A | 8/1982 | Lee et al. |
| 4,399,813 A | 8/1983 | Barber |
| 4,423,721 A | 1/1984 | Otte et al. |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A | 12/1986 | Harder et al. |
| 4,638,799 A | 1/1987 | Moore |
| 4,657,550 A | 4/1987 | Daher |
| 4,743,256 A | 5/1988 | Brantigan |
| 4,773,402 A | 9/1988 | Asher et al. |
| 4,787,378 A | 11/1988 | Sodhi |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A | 11/1989 | Brantigan |
| 4,898,186 A | 2/1990 | Ikada et al. |
| 4,904,261 A | 2/1990 | Dove et al. |
| 4,950,270 A | 8/1990 | Bowman et al. |
| 4,961,740 A | 10/1990 | Ray et al. |
| 4,969,888 A | 11/1990 | Scholten et al. |
| 4,981,481 A | 1/1991 | Kranz et al. |
| 5,034,011 A | 7/1991 | Howland |
| 5,034,013 A | 7/1991 | Kyle et al. |
| 5,035,697 A | 7/1991 | Frigg |
| 5,041,118 A | 8/1991 | Wasilewski |
| 5,053,035 A | 10/1991 | McLaren |
| 5,059,193 A | 10/1991 | Kuslich |
| 5,066,296 A | 11/1991 | Chapman et al. |
| 5,098,434 A | 3/1992 | Serbousek |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,139,500 A | 8/1992 | Schwartz |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,380,325 A | 1/1995 | Lahille et al. |
| 5,390,683 A | 2/1995 | Pisharodi |
| 5,433,718 A | 7/1995 | Brinker |
| 5,443,466 A | 8/1995 | Shah |
| 5,458,638 A | 10/1995 | Kuslich et al. |
| 5,470,334 A | 11/1995 | Ross et al. |
| 5,480,402 A | 1/1996 | Kim |
| 5,569,249 A | 10/1996 | James et al. |
| 5,591,235 A | 1/1997 | Kuslich |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs et al. |
| 5,626,616 A | 5/1997 | Speece |
| 5,643,264 A | 7/1997 | Sherman et al. |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,709,683 A | 1/1998 | Bagby |
| 5,713,904 A | 2/1998 | Errico et al. |
| 5,716,358 A | 2/1998 | Ochoa et al. |
| 5,725,581 A | 3/1998 | Brånemark |
| 5,743,912 A | 4/1998 | LaHille et al. |
| 5,759,035 A | 6/1998 | Ricci |
| 5,766,174 A | 6/1998 | Perry |
| 5,766,252 A | 6/1998 | Henry et al. |
| 5,766,261 A | 6/1998 | Neal et al. |
| 5,788,699 A | 8/1998 | Bobst et al. |
| 5,800,440 A | 9/1998 | Stead |
| 5,868,749 A | 2/1999 | Reed |
| 5,897,556 A | 4/1999 | Drewry et al. |
| 5,928,239 A | 7/1999 | Mirza |
| 5,941,885 A | 8/1999 | Jackson |
| 5,961,522 A | 10/1999 | Mehdizadeh |
| 5,961,554 A | 10/1999 | Janson et al. |
| 6,010,507 A | 1/2000 | Rudloff |
| 6,015,409 A | 1/2000 | Jackson |
| 6,030,162 A | 2/2000 | Huebner et al. |
| 6,053,916 A | 4/2000 | Moore |
| 6,056,749 A | 5/2000 | Kuslich |
| 6,066,175 A | 5/2000 | Henderson et al. |
| 6,086,589 A | 7/2000 | Kuslich et al. |
| 6,096,080 A | 8/2000 | Nicholson et al. |
| 6,120,292 A | 9/2000 | Buser et al. |
| 6,120,504 A | 9/2000 | Brumback et al. |
| 6,129,730 A | 10/2000 | Bono et al. |
| 6,143,031 A | 11/2000 | Knothe et al. |
| 6,197,062 B1 | 3/2001 | Fenlin |
| 6,206,924 B1 | 3/2001 | Timm |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,264,657 B1 | 7/2001 | Urbahns et al. |
| 6,270,528 B1 | 8/2001 | McKay |
| 6,287,343 B1 | 9/2001 | Kuslich et al. |
| 6,302,885 B1 | 10/2001 | Essiger |
| 6,302,914 B1 | 10/2001 | Michelson |
| 6,306,140 B1 | 10/2001 | Siddiqui |
| 6,319,253 B1 | 11/2001 | Ackeret et al. |
| 6,406,498 B1 | 6/2002 | Tormala et al. |
| 6,409,768 B1 | 6/2002 | Tepic et al. |
| 6,436,139 B1 | 8/2002 | Shapiro et al. |
| 6,451,020 B1 | 9/2002 | Zucherman et al. |
| 6,471,707 B1 | 10/2002 | Miller et al. |
| 6,485,518 B1 | 11/2002 | Cornwall et al. |
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,527,775 B1 | 3/2003 | Warburton |
| 6,551,343 B1 | 4/2003 | Törmälii et al. |
| 6,556,857 B1 | 4/2003 | Estes et al. |
| 6,558,386 B1 | 5/2003 | Cragg |
| 6,565,566 B1 | 5/2003 | Wagner et al. |
| 6,575,899 B1 | 6/2003 | Foley et al. |
| 6,575,991 B1 | 6/2003 | Chesbrough et al. |
| 6,579,293 B1 | 6/2003 | Chandran |
| 6,582,431 B1 | 6/2003 | Ray |
| 6,582,467 B1 | 6/2003 | Teitelbaum et al. |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,607,530 B1 | 8/2003 | Carl et al. |
| 6,620,163 B1 | 9/2003 | Michelson |
| 6,635,059 B2 | 10/2003 | Randall et al. |
| 6,666,868 B2 | 12/2003 | Fallin |
| 6,669,529 B1 | 12/2003 | Scaries |
| 6,673,075 B2 | 1/2004 | Santilli |
| 6,692,501 B2 | 2/2004 | Michelson |
| 6,712,852 B1 | 3/2004 | Chung et al. |
| 6,723,099 B1 | 4/2004 | Goshert |
| 6,723,100 B2 | 4/2004 | Biedermann et al. |

(56) References Cited

U.S. PATENT DOCUMENTS

| | | |
|---|---|---|
| 6,740,118 B2 | 5/2004 | Eisermann et al. |
| 6,743,257 B2 | 6/2004 | Castro |
| D493,533 S | 7/2004 | Blain |
| 6,793,656 B1 | 9/2004 | Mathews |
| 6,827,740 B1 | 12/2004 | Michelson |
| 6,984,235 B2 | 1/2006 | Huebner |
| 6,989,033 B1 | 1/2006 | Schmidt |
| 6,991,461 B2 | 1/2006 | Gittleman |
| 6,993,406 B1 | 1/2006 | Cesarano et al. |
| 7,018,416 B2 | 3/2006 | Hanson et al. |
| 7,118,579 B2 | 10/2006 | Michelson |
| 7,147,666 B1 | 12/2006 | Grisoni |
| 7,175,663 B1 | 2/2007 | Stone |
| 7,211,085 B2 | 5/2007 | Michelson |
| 7,223,269 B2 | 5/2007 | Chappuis |
| 7,300,439 B2 | 11/2007 | May |
| 7,314,488 B2 | 1/2008 | Reiley |
| 7,335,205 B2 | 2/2008 | Aeschlimann et al. |
| 7,338,500 B2 | 3/2008 | Chappuis |
| 7,396,365 B2 | 7/2008 | Michelson |
| 7,452,359 B1 | 11/2008 | Michelson |
| 7,452,369 B2 | 11/2008 | Barry |
| 7,481,831 B2 | 1/2009 | Bonutti |
| 7,527,649 B1 | 5/2009 | Blain |
| 7,534,254 B1 | 5/2009 | Michelson |
| 7,537,616 B1 | 5/2009 | Branch et al. |
| 7,569,054 B2 | 8/2009 | Michelson |
| 7,569,059 B2 | 8/2009 | Cerundolo |
| 7,601,155 B2 | 10/2009 | Petersen |
| 7,608,097 B2 | 10/2009 | Kyle |
| 7,608,098 B1 | 10/2009 | Stone et al. |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,846,162 B2 | 12/2010 | Nelson et al. |
| 7,850,732 B2 | 12/2010 | Heinz |
| 7,857,832 B2 | 12/2010 | Culbert et al. |
| 7,887,565 B2 | 2/2011 | Michelson |
| 7,892,265 B2 | 2/2011 | Perez-Cruet et al. |
| 7,901,439 B2 | 3/2011 | Horton |
| 7,909,832 B2 | 3/2011 | Michelson |
| 7,922,765 B2 | 4/2011 | Reiley |
| 7,942,879 B2 | 5/2011 | Christie et al. |
| 7,951,176 B2 | 5/2011 | Grady et al. |
| 8,052,728 B2 | 11/2011 | Hestad |
| 8,062,365 B2 | 11/2011 | Schwab |
| 8,066,705 B2 | 11/2011 | Michelson |
| 8,066,709 B2 | 11/2011 | Michelson |
| 8,092,505 B2 | 1/2012 | Sommers |
| 8,142,481 B2 | 3/2012 | Warnick |
| 8,202,305 B2 | 6/2012 | Reiley |
| 8,221,499 B2 | 7/2012 | Lazzara et al. |
| 8,257,398 B2 | 9/2012 | Jackson |
| 8,268,099 B2 | 9/2012 | O'Neill et al. |
| 8,308,779 B2 | 11/2012 | Reiley |
| 8,308,783 B2 | 11/2012 | Morris et al. |
| 8,317,862 B2 | 11/2012 | Troger et al. |
| 8,348,950 B2 | 1/2013 | Assell et al. |
| 8,350,186 B2 | 1/2013 | Jones et al. |
| 8,353,932 B2 | 1/2013 | Jackson |
| 8,388,667 B2 | 3/2013 | Reiley et al. |
| 8,394,129 B2 | 3/2013 | Morgenstern Lopez |
| 8,398,635 B2 | 3/2013 | Vaidya |
| 8,398,682 B2 | 3/2013 | Jackson et al. |
| 8,414,648 B2 | 4/2013 | Reiley |
| 8,425,570 B2 | 4/2013 | Reiley |
| 8,430,930 B2 | 4/2013 | Hunt |
| 8,444,693 B2 | 5/2013 | Reiley |
| 8,449,585 B2 | 5/2013 | Wallenstein et al. |
| 8,467,851 B2 | 6/2013 | Mire et al. |
| 8,470,004 B2 | 6/2013 | Reiley |
| 8,475,505 B2 | 7/2013 | Nebosky et al. |
| 8,529,608 B2 | 9/2013 | Terrill et al. |
| 8,597,299 B2 | 12/2013 | Farr et al. |
| 8,608,802 B2 | 12/2013 | Bagga et al. |
| D697,209 S | 1/2014 | Walthall et al. |
| 8,641,737 B2 | 2/2014 | Matthis et al. |
| 8,641,766 B2 | 2/2014 | Donner et al. |
| 8,663,298 B2 * | 3/2014 | Keyer et al. ........ A61B 17/7037 606/305 |
| 8,663,332 B1 | 3/2014 | To et al. |
| 8,672,986 B2 | 3/2014 | Klaue et al. |
| 8,734,462 B2 | 5/2014 | Reiley et al. |
| 8,778,026 B2 | 7/2014 | Mauldin |
| 8,840,623 B2 | 9/2014 | Reiley |
| 8,840,651 B2 | 9/2014 | Reiley |
| 8,845,693 B2 | 9/2014 | Smith et al. |
| 8,858,601 B2 | 10/2014 | Reiley |
| 8,888,827 B2 | 11/2014 | Harper et al. |
| 8,894,685 B2 | 11/2014 | Mickiewicz et al. |
| 8,920,477 B2 | 12/2014 | Reiley |
| 8,926,670 B2 | 1/2015 | Jackson |
| 8,936,623 B2 | 1/2015 | Jackson |
| 8,945,190 B2 | 2/2015 | Culbert et al. |
| 8,945,193 B2 | 2/2015 | Kirschman |
| 8,951,254 B2 | 2/2015 | Mayer et al. |
| 8,951,293 B2 | 2/2015 | Glazer et al. |
| 8,951,295 B2 | 2/2015 | Matityahu et al. |
| 8,961,571 B2 | 2/2015 | Lee et al. |
| 8,979,911 B2 | 3/2015 | Martineau et al. |
| 8,986,348 B2 | 3/2015 | Reiley |
| RE45,484 E | 4/2015 | Foley et al. |
| 9,039,743 B2 | 5/2015 | Reiley |
| 9,044,321 B2 | 6/2015 | Mauldin et al. |
| 9,060,876 B1 | 6/2015 | To et al. |
| 9,089,371 B1 | 7/2015 | Faulhaber |
| D738,498 S | 9/2015 | Frey et al. |
| 9,131,955 B2 | 9/2015 | Swofford |
| 9,149,286 B1 | 10/2015 | Greenhalgh et al. |
| 9,173,692 B1 | 11/2015 | Kaloostian |
| 9,198,676 B2 | 12/2015 | Pilgeram et al. |
| 9,220,535 B2 | 12/2015 | Röbling et al. |
| 9,314,286 B2 | 4/2016 | Bottlang et al. |
| 9,314,348 B2 | 4/2016 | Emstad |
| 9,358,047 B2 | 6/2016 | Mishra et al. |
| 9,358,057 B1 | 6/2016 | Whipple et al. |
| 9,375,243 B1 | 6/2016 | Vestgaarden |
| 9,375,323 B2 | 6/2016 | Reiley |
| 9,445,852 B2 | 9/2016 | Sweeney |
| 9,451,999 B2 | 9/2016 | Simpson et al. |
| 9,452,065 B1 | 9/2016 | Lawson |
| 9,486,264 B2 | 11/2016 | Reiley et al. |
| 9,492,201 B2 | 11/2016 | Reiley |
| 9,498,264 B2 | 11/2016 | Harshman et al. |
| 9,510,872 B2 | 12/2016 | Donner et al. |
| 9,517,095 B2 | 12/2016 | Vaidya |
| 9,526,548 B2 | 12/2016 | Asfora |
| 9,554,909 B2 | 1/2017 | Donner |
| 9,561,063 B2 | 2/2017 | Reiley |
| 9,566,100 B2 | 2/2017 | Asfora |
| 9,603,613 B2 | 3/2017 | Schoenefeld et al. |
| 9,603,644 B2 | 3/2017 | Sweeney |
| D783,821 S | 4/2017 | Folsom et al. |
| 9,615,856 B2 | 4/2017 | Arnett et al. |
| 9,622,783 B2 | 4/2017 | Reiley et al. |
| 9,655,656 B2 | 5/2017 | Whipple |
| 9,662,124 B2 | 5/2017 | Assell et al. |
| 9,662,128 B2 | 5/2017 | Reiley |
| 9,662,157 B2 | 5/2017 | Schneider et al. |
| 9,662,158 B2 | 5/2017 | Reiley |
| 9,675,394 B2 | 6/2017 | Reiley |
| 9,743,969 B2 | 8/2017 | Reiley |
| 9,757,154 B2 | 9/2017 | Donner et al. |
| 9,763,695 B2 | 9/2017 | Mirda |
| 9,763,802 B2 | 9/2017 | Baynham |
| 9,775,648 B2 | 10/2017 | Greenberg et al. |
| 9,788,866 B2 | 10/2017 | Jackson |
| 9,808,292 B2 | 11/2017 | Jackson |
| 9,808,298 B2 | 11/2017 | Stroncek et al. |
| 9,808,299 B2 | 11/2017 | Goel et al. |

(56) References Cited

U.S. PATENT DOCUMENTS

| | | |
|---|---|---|
| 9,808,337 B2 | 11/2017 | Housman et al. |
| 9,820,789 B2 | 11/2017 | Reiley |
| 9,826,986 B2 | 11/2017 | Donner et al. |
| 9,833,321 B2 | 12/2017 | Rindal et al. |
| 9,839,448 B2 | 12/2017 | Reckling et al. |
| 9,848,889 B2 | 12/2017 | Taylor et al. |
| 9,848,892 B2 | 12/2017 | Biedermann et al. |
| 9,883,874 B1 | 2/2018 | Vestgaarden |
| 9,888,911 B2 | 2/2018 | Siegal |
| 9,936,983 B2 | 4/2018 | Mesiwala et al. |
| 9,949,776 B2 | 4/2018 | Mobasser et al. |
| 9,949,843 B2 | 4/2018 | Reiley et al. |
| D816,843 S | 5/2018 | Lewis |
| 9,956,013 B2 | 5/2018 | Reiley et al. |
| 9,993,276 B2 | 6/2018 | Russell |
| 9,993,277 B2 | 6/2018 | Krinke et al. |
| 9,999,449 B2 | 6/2018 | Bonutti |
| 10,004,547 B2 | 6/2018 | Reiley |
| 10,034,676 B2 | 7/2018 | Donner |
| 10,058,430 B2 | 8/2018 | Donner et al. |
| 10,064,670 B2 | 9/2018 | Mootien et al. |
| D831,828 S | 10/2018 | Horton et al. |
| 10,166,022 B2 | 1/2019 | Early et al. |
| 10,166,033 B2 | 1/2019 | Reiley et al. |
| 10,179,014 B1 | 1/2019 | Menmuir et al. |
| 10,188,403 B2 | 1/2019 | Mirochinik et al. |
| 10,188,432 B2 * | 1/2019 | Jackson et al. .... A61B 17/7037 |
| 10,188,442 B2 | 1/2019 | Mazel |
| 10,194,951 B2 | 2/2019 | Jackson et al. |
| 10,194,962 B2 | 2/2019 | Schneider et al. |
| 10,201,427 B2 | 2/2019 | Mauldin et al. |
| 10,219,841 B1 | 3/2019 | Compton et al. |
| 10,219,885 B2 | 3/2019 | Mamo et al. |
| D846,977 S | 4/2019 | Williams et al. |
| D847,336 S | 4/2019 | Asfora et al. |
| 10,245,044 B2 | 4/2019 | Petersen |
| 10,245,076 B2 | 4/2019 | Fitzpatrick |
| 10,245,087 B2 | 4/2019 | Donner et al. |
| 10,258,380 B2 | 4/2019 | Sinha |
| 10,258,393 B2 | 4/2019 | Caploon et al. |
| 10,258,394 B2 | 4/2019 | Harshman et al. |
| 10,271,882 B2 | 4/2019 | Biedermann et al. |
| D847,994 S | 5/2019 | Asfora et al. |
| 10,278,737 B2 | 5/2019 | Smith |
| 10,285,745 B2 | 5/2019 | Cummins et al. |
| 10,292,778 B2 | 5/2019 | Kostrzewski et al. |
| D850,616 S | 6/2019 | Asfora et al. |
| 10,314,631 B2 | 6/2019 | Gonzalez Blohm et al. |
| 10,321,937 B2 | 6/2019 | Cormier et al. |
| 10,321,945 B2 | 6/2019 | Schifano et al. |
| 10,335,200 B2 | 7/2019 | Jackson |
| 10,335,202 B2 | 7/2019 | Ziolo et al. |
| 10,335,204 B2 | 7/2019 | Matthis et al. |
| 10,335,206 B2 | 7/2019 | Nichols et al. |
| 10,335,211 B2 | 7/2019 | Chan et al. |
| 10,335,212 B2 | 7/2019 | Paolino et al. |
| 10,335,216 B2 | 7/2019 | Mari et al. |
| 10,335,217 B2 | 7/2019 | Lindner |
| 10,342,586 B2 | 7/2019 | Schneider |
| 10,349,983 B2 | 7/2019 | Purcell et al. |
| 10,349,986 B2 | 7/2019 | Wall et al. |
| 10,357,287 B2 | 7/2019 | Schlaepfer et al. |
| 10,363,070 B2 | 7/2019 | Jackson et al. |
| 10,363,073 B2 | 7/2019 | Raina et al. |
| 10,363,140 B2 | 7/2019 | Mauldin et al. |
| 10,363,143 B2 | 7/2019 | Neubardt |
| 10,368,919 B2 | 8/2019 | Pham et al. |
| 10,413,332 B2 | 9/2019 | Schumacher et al. |
| 10,426,539 B2 | 10/2019 | Schifano et al. |
| 10,433,880 B2 | 10/2019 | Donner et al. |
| 10,441,319 B2 | 10/2019 | Jackson et al. |
| 10,456,268 B2 | 10/2019 | Mercier et al. |
| 10,463,402 B2 | 11/2019 | Biester et al. |
| 10,478,227 B2 | 11/2019 | Leff et al. |
| 10,485,596 B2 | 11/2019 | Koller et al. |
| 10,492,841 B2 | 12/2019 | Hartdegen et al. |
| 10,492,921 B2 | 12/2019 | McShane, III et al. |
| 10,517,734 B2 | 12/2019 | Donner |
| 10,531,898 B2 | 1/2020 | Boulot |
| 10,531,904 B2 | 1/2020 | Kolb |
| 10,537,340 B2 | 1/2020 | Mirochinik et al. |
| D875,931 S | 2/2020 | Asfora et al. |
| 10,555,758 B2 | 2/2020 | Magee et al. |
| 10,588,676 B2 | 3/2020 | Kang et al. |
| 10,588,677 B2 | 3/2020 | McDonnell |
| 10,595,917 B2 | 3/2020 | Loftus |
| 10,596,003 B2 | 3/2020 | Donner et al. |
| 10,603,054 B2 | 3/2020 | Asfora et al. |
| 10,603,055 B2 | 3/2020 | Donner et al. |
| 10,603,087 B2 | 3/2020 | Brenzel et al. |
| 10,603,176 B2 | 3/2020 | Arnold et al. |
| 10,610,275 B2 | 4/2020 | Brianza |
| 10,610,276 B2 | 4/2020 | Lutz |
| 10,610,370 B2 | 4/2020 | Baynham |
| 10,610,728 B2 | 4/2020 | Fano et al. |
| 10,617,453 B2 | 4/2020 | Beckett et al. |
| 10,653,454 B2 | 5/2020 | Frey et al. |
| 10,653,455 B2 | 5/2020 | Lehman et al. |
| 10,653,544 B2 | 5/2020 | Forsell |
| 10,660,657 B2 | 5/2020 | Slobitker et al. |
| 10,660,679 B2 | 5/2020 | Kang et al. |
| 10,660,684 B2 | 5/2020 | Kang et al. |
| 10,667,923 B2 | 6/2020 | Sullivan et al. |
| 10,682,131 B2 | 6/2020 | Fallin et al. |
| 10,682,150 B2 | 6/2020 | Stark |
| 10,682,437 B2 | 6/2020 | Roth |
| 10,709,570 B2 | 7/2020 | Stauffer et al. |
| 10,711,334 B2 | 7/2020 | Patel et al. |
| 10,729,475 B2 | 8/2020 | Childs |
| 10,729,482 B2 | 8/2020 | Fantigrossi et al. |
| 10,743,995 B2 | 8/2020 | Fallin et al. |
| D895,111 S | 9/2020 | Frey et al. |
| 10,758,283 B2 | 9/2020 | Frey et al. |
| 10,758,285 B2 | 9/2020 | Geist et al. |
| 10,792,074 B2 | 10/2020 | Jackson |
| 10,799,277 B2 | 10/2020 | Kulper et al. |
| 10,799,367 B2 | 10/2020 | Vrionis et al. |
| 10,806,597 B2 | 10/2020 | Sournac et al. |
| 10,842,511 B2 | 11/2020 | Patel et al. |
| 10,842,634 B2 | 11/2020 | Pasini et al. |
| D904,615 S | 12/2020 | Asfora et al. |
| D905,232 S | 12/2020 | Schifano et al. |
| 10,856,922 B2 | 12/2020 | Loke et al. |
| 10,864,029 B2 | 12/2020 | Redmond et al. |
| 10,898,333 B2 | 1/2021 | Cordaro |
| 10,905,472 B2 | 2/2021 | Mari et al. |
| 10,912,654 B2 | 2/2021 | Scheland |
| 10,932,838 B2 | 3/2021 | Mehl et al. |
| 10,939,944 B2 | 3/2021 | Wapner et al. |
| 10,940,008 B2 | 3/2021 | Patel |
| 10,959,758 B2 | 3/2021 | Mesiwala et al. |
| 10,959,830 B2 | 3/2021 | Williams et al. |
| 10,987,142 B2 | 4/2021 | Poelstra et al. |
| 10,993,754 B2 | 5/2021 | Kuntz et al. |
| 10,993,757 B2 | 5/2021 | Schifano et al. |
| 11,000,325 B2 | 5/2021 | Sommers et al. |
| 11,006,985 B2 | 5/2021 | Caploon et al. |
| D921,898 S | 6/2021 | Schifano et al. |
| D922,568 S | 6/2021 | Schifano et al. |
| 11,020,129 B2 | 6/2021 | LaNeve et al. |
| 11,033,309 B2 | 6/2021 | Zadeh |
| 11,051,856 B2 | 7/2021 | Jackson |
| 11,052,229 B2 | 7/2021 | Althoff et al. |
| 11,058,443 B2 | 7/2021 | Siccardi et al. |
| 11,058,550 B2 | 7/2021 | LaNeve et al. |
| 11,058,556 B2 | 7/2021 | LaNeve et al. |
| 11,071,573 B2 | 7/2021 | Schneider et al. |
| D927,295 S | 8/2021 | Lanois |
| 11,116,519 B2 | 9/2021 | Sand et al. |
| 11,116,557 B2 | 9/2021 | Zander et al. |
| 11,147,591 B2 | 10/2021 | Jackson |
| 11,147,597 B2 | 10/2021 | Jackson |
| 11,147,688 B2 | 10/2021 | Reckling et al. |
| 11,154,402 B1 | 10/2021 | LaNeve et al. |

(56) References Cited

U.S. PATENT DOCUMENTS

| | | |
|---|---|---|
| D935,025 S | 11/2021 | Schifano et al. |
| D935,876 S | 11/2021 | Lanois |
| 11,166,821 B2 | 11/2021 | Sazy |
| 11,172,939 B2 | 11/2021 | Donner et al. |
| 11,172,969 B2 | 11/2021 | Suddaby |
| 11,219,534 B2 | 1/2022 | Wall |
| 11,224,467 B2 | 1/2022 | Peterson et al. |
| 11,224,490 B2 | 1/2022 | MacMillan et al. |
| 11,234,830 B2 | 2/2022 | Mesiwala et al. |
| 11,259,854 B2 | 3/2022 | Thornes et al. |
| 11,266,767 B2 | 3/2022 | Roth et al. |
| 11,273,043 B1 | 3/2022 | Abbasi |
| 11,284,798 B2 | 3/2022 | Donner et al. |
| 11,284,887 B2 | 3/2022 | Hartdegen et al. |
| 11,291,485 B2 | 4/2022 | Mauldin et al. |
| 11,298,747 B2 | 4/2022 | Klein et al. |
| D951,455 S | 5/2022 | Ginn |
| 11,318,020 B2 | 5/2022 | Bohl |
| 11,331,123 B2 * | 5/2022 | Ballard et al. ..... A61B 17/8695 |
| 11,337,821 B2 | 5/2022 | Mauldin et al. |
| 11,369,419 B2 | 6/2022 | Mesiwala et al. |
| 11,382,755 B2 | 7/2022 | LaNeve et al. |
| 11,382,770 B2 | 7/2022 | LaNeve et al. |
| 11,389,305 B2 | 7/2022 | LaNeve et al. |
| 11,413,073 B2 | 8/2022 | Castro |
| 11,419,652 B2 | 8/2022 | Wickham et al. |
| 11,419,653 B2 | 8/2022 | Castro |
| 11,419,654 B2 | 8/2022 | Castro |
| 11,432,829 B2 | 9/2022 | Castro |
| 11,452,548 B2 | 9/2022 | Harshman et al. |
| 11,510,801 B2 | 11/2022 | Archbold |
| D972,137 S | 12/2022 | Schifano et al. |
| 11,517,361 B2 | 12/2022 | Major et al. |
| 11,553,945 B2 | 1/2023 | Castro |
| 11,553,953 B1 | 1/2023 | Robbins |
| 11,580,268 B2 | 2/2023 | Suddaby |
| 11,583,326 B2 | 2/2023 | Suddaby |
| 11,607,251 B2 | 3/2023 | Albert et al. |
| 11,607,256 B1 | 3/2023 | Folsom et al. |
| 11,660,126 B1 | 5/2023 | Abbasi et al. |
| 11,696,771 B2 | 7/2023 | Assell et al. |
| 11,737,884 B2 | 8/2023 | Vestgaarden |
| 11,806,197 B2 | 11/2023 | Frey et al. |
| 11,850,156 B2 | 12/2023 | Mauldin et al. |
| 11,883,296 B2 | 1/2024 | Morgenstern Lopez et al. |
| 11,925,475 B2 | 3/2024 | Trabish et al. |
| 11,980,552 B2 | 5/2024 | Castro |
| 12,016,589 B2 | 6/2024 | Murphy |
| 12,036,131 B2 | 7/2024 | Castro |
| 12,036,135 B2 | 7/2024 | Castro |
| 12,053,208 B2 | 8/2024 | Vitale et al. |
| 12,127,769 B2 | 10/2024 | Casey et al. |
| 12,167,877 B2 | 12/2024 | Harshman et al. |
| 12,171,439 B2 | 12/2024 | Nayet et al. |
| 12,207,828 B2 | 1/2025 | Asfora |
| 12,245,795 B2 | 3/2025 | Spangler et al. |
| 12,251,165 B2 | 3/2025 | Mosnier et al. |
| 12,251,320 B2 | 3/2025 | Casey et al. |
| 12,262,918 B2 | 4/2025 | Yacoub et al. |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0019637 A1 | 2/2002 | Frey et al. |
| 2002/0029043 A1 | 3/2002 | Ahrens et al. |
| 2002/0038123 A1 | 3/2002 | Visotsky et al. |
| 2002/0049497 A1 | 4/2002 | Mason |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0120335 A1 | 8/2002 | Angelucci et al. |
| 2002/0128652 A1 | 9/2002 | Ferree |
| 2002/0143334 A1 | 10/2002 | von Hoffmann et al. |
| 2002/0143335 A1 | 10/2002 | von Hoffmann et al. |
| 2002/0151903 A1 | 10/2002 | Takei et al. |
| 2002/0169507 A1 | 11/2002 | Malone |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083668 A1 | 5/2003 | Rogers et al. |
| 2003/0083688 A1 | 5/2003 | Simonson |
| 2003/0088251 A1 | 5/2003 | Braun et al. |
| 2003/0097131 A1 | 5/2003 | Schon et al. |
| 2003/0139815 A1 | 7/2003 | Grooms et al. |
| 2003/0181979 A1 | 9/2003 | Ferree |
| 2003/0181982 A1 | 9/2003 | Kuslich |
| 2003/0199983 A1 | 10/2003 | Michelson |
| 2003/0229358 A1 | 12/2003 | Errico et al. |
| 2003/0233146 A1 | 12/2003 | Grinberg et al. |
| 2003/0233147 A1 | 12/2003 | Nicholson et al. |
| 2004/0010315 A1 | 1/2004 | Song |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |
| 2004/0097927 A1 | 5/2004 | Yeung et al. |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |
| 2004/0147929 A1 | 7/2004 | Biedermann et al. |
| 2004/0158324 A1 | 8/2004 | Lange |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0186572 A1 | 9/2004 | Lange et al. |
| 2004/0210221 A1 | 10/2004 | Kozak et al. |
| 2004/0225360 A1 | 11/2004 | Malone |
| 2004/0230305 A1 | 11/2004 | Gorensek et al. |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0037319 A1 | 2/2005 | Bulard et al. |
| 2005/0049590 A1 | 3/2005 | Alleyne et al. |
| 2005/0055023 A1 | 3/2005 | Sohngen et al. |
| 2005/0070905 A1 | 3/2005 | Donnelly et al. |
| 2005/0070907 A1 | 3/2005 | Abernathie |
| 2005/0071004 A1 | 3/2005 | Re et al. |
| 2005/0075641 A1 | 4/2005 | Singhatat et al. |
| 2005/0080415 A1 | 4/2005 | Keyer et al. |
| 2005/0107878 A1 | 5/2005 | Conchy |
| 2005/0112397 A1 | 5/2005 | Rolfe et al. |
| 2005/0113919 A1 | 5/2005 | Cragg et al. |
| 2005/0124993 A1 | 6/2005 | Chappuis |
| 2005/0131409 A1 | 6/2005 | Chervitz et al. |
| 2005/0137605 A1 | 6/2005 | Assell et al. |
| 2005/0143837 A1 | 6/2005 | Ferree |
| 2005/0149192 A1 | 7/2005 | Zucherman et al. |
| 2005/0159749 A1 | 7/2005 | Levy et al. |
| 2005/0159812 A1 | 7/2005 | Dinger et al. |
| 2005/0165398 A1 | 7/2005 | Reiley |
| 2005/0192572 A1 | 9/2005 | Abdelgany et al. |
| 2005/0216082 A1 | 9/2005 | Wilson et al. |
| 2005/0228384 A1 | 10/2005 | Zucherman et al. |
| 2005/0228388 A1 | 10/2005 | Brodke et al. |
| 2005/0246021 A1 | 11/2005 | Ringeisen et al. |
| 2005/0251146 A1 | 11/2005 | Martz et al. |
| 2005/0273101 A1 | 12/2005 | Schumacher |
| 2005/0277940 A1 | 12/2005 | Neff |
| 2006/0004396 A1 | 1/2006 | Easley et al. |
| 2006/0025771 A1 | 2/2006 | Jackson |
| 2006/0036247 A1 | 2/2006 | Michelson |
| 2006/0036251 A1 | 2/2006 | Reiley |
| 2006/0036252 A1 | 2/2006 | Baynham et al. |

(56) References Cited

U.S. PATENT DOCUMENTS

| | | |
|---|---|---|
| 2006/0054171 A1 | 3/2006 | Dall |
| 2006/0058793 A1 | 3/2006 | Michelson |
| 2006/0058800 A1 | 3/2006 | Ainsworth et al. |
| 2006/0062825 A1 | 3/2006 | Maccecchini |
| 2006/0084986 A1 | 4/2006 | Grinberg et al. |
| 2006/0089644 A1 | 4/2006 | Felix |
| 2006/0089656 A1 | 4/2006 | Allard et al. |
| 2006/0095038 A1 | 5/2006 | Jackson |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0178673 A1 | 8/2006 | Curran |
| 2006/0195094 A1 | 8/2006 | McGraw et al. |
| 2006/0217717 A1 | 9/2006 | Whipple |
| 2006/0241600 A1 | 10/2006 | Ensign et al. |
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1 | 2/2007 | McCord et al. |
| 2007/0038219 A1 | 2/2007 | Matthis et al. |
| 2007/0049933 A1 | 3/2007 | Ahn et al. |
| 2007/0066977 A1 | 3/2007 | Assell et al. |
| 2007/0073295 A1 | 3/2007 | Biederman et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0093898 A1 | 4/2007 | Schwab et al. |
| 2007/0106383 A1 | 5/2007 | Abdou |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |
| 2007/0161985 A1 | 7/2007 | Demakas et al. |
| 2007/0161989 A1 | 7/2007 | Heinz et al. |
| 2007/0173820 A1 | 7/2007 | Trieu |
| 2007/0219634 A1 | 9/2007 | Greenhalgh et al. |
| 2007/0233080 A1 | 10/2007 | Na et al. |
| 2007/0233146 A1 | 10/2007 | Henniges et al. |
| 2007/0233247 A1 | 10/2007 | Schwab |
| 2007/0250166 A1 | 10/2007 | McKay |
| 2007/0270833 A1 | 11/2007 | Bonutti et al. |
| 2007/0270858 A1 | 11/2007 | Trieu et al. |
| 2007/0270879 A1 | 11/2007 | Isaza et al. |
| 2007/0282443 A1 | 12/2007 | Globerman et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0071356 A1 | 3/2008 | Greenhalgh et al. |
| 2008/0109083 A1 | 5/2008 | Van Hoeck et al. |
| 2008/0125868 A1 | 5/2008 | Branemark et al. |
| 2008/0132901 A1 | 6/2008 | Recoules-Arche et al. |
| 2008/0140082 A1 | 6/2008 | Erdem et al. |
| 2008/0147079 A1 | 6/2008 | Chin et al. |
| 2008/0154314 A1 | 6/2008 | McDevitt |
| 2008/0154374 A1 | 6/2008 | Labrom |
| 2008/0161810 A1 | 7/2008 | Melkent |
| 2008/0161927 A1 | 7/2008 | Savage et al. |
| 2008/0183204 A1 | 7/2008 | Greenhalgh et al. |
| 2008/0234758 A1 | 9/2008 | Fisher et al. |
| 2008/0249579 A1 | 10/2008 | Taylor |
| 2008/0255562 A1 | 10/2008 | Gil et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0294202 A1 | 11/2008 | Peterson et al. |
| 2008/0306554 A1 | 12/2008 | McKinley |
| 2009/0012529 A1 | 1/2009 | Blain et al. |
| 2009/0018660 A1 | 1/2009 | Roush |
| 2009/0024174 A1 | 1/2009 | Stark |
| 2009/0036927 A1 | 2/2009 | Vestgaarden |
| 2009/0037148 A1 | 2/2009 | Lin et al. |
| 2009/0043393 A1 | 2/2009 | Duggal et al. |
| 2009/0082810 A1 | 3/2009 | Bhatnagar et al. |
| 2009/0082869 A1 | 3/2009 | Slemker et al. |
| 2009/0099602 A1 | 4/2009 | Aflatoon |
| 2009/0099610 A1 | 4/2009 | Johnson et al. |
| 2009/0105770 A1 | 4/2009 | Berrevooets et al. |
| 2009/0118771 A1 | 5/2009 | Gonzalez-Hernandez |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0171394 A1 | 7/2009 | Adbou |
| 2009/0187247 A1 | 7/2009 | Metcalf, Jr. et al. |
| 2009/0216238 A1 | 8/2009 | Stark |
| 2009/0270929 A1 | 10/2009 | Suddaby |
| 2009/0287254 A1 | 11/2009 | Nayet et al. |
| 2009/0312798 A1 | 12/2009 | Varela |
| 2009/0319043 A1 | 12/2009 | McDevitt et al. |
| 2009/0324678 A1 | 12/2009 | Thorne et al. |
| 2010/0003638 A1 | 1/2010 | Collins et al. |
| 2010/0022535 A1 | 1/2010 | Lee et al. |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0094420 A1 | 4/2010 | Grohowski |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0131011 A1 | 5/2010 | Stark |
| 2010/0137990 A1 | 6/2010 | Apatsidis et al. |
| 2010/0145461 A1 | 6/2010 | Landry et al. |
| 2010/0160977 A1 | 6/2010 | Gephart et al. |
| 2010/0168798 A1 | 7/2010 | Clineff et al. |
| 2010/0191292 A1 | 7/2010 | DeMeo et al. |
| 2010/0228301 A1 | 9/2010 | Greenhalgh et al. |
| 2010/0262242 A1 | 10/2010 | Chavatte et al. |
| 2010/0268228 A1 | 10/2010 | Petersen |
| 2010/0280619 A1 | 11/2010 | Yuan et al. |
| 2010/0280622 A1 | 11/2010 | McKinley |
| 2010/0286778 A1 | 11/2010 | Eisermann et al. |
| 2010/0298889 A1 | 11/2010 | Wilberg et al. |
| 2010/0331851 A1 | 12/2010 | Huene |
| 2010/0331893 A1 | 12/2010 | Geist et al. |
| 2011/0009869 A1 | 1/2011 | Marino et al. |
| 2011/0009966 A1 | 1/2011 | Michelson |
| 2011/0022089 A1 | 1/2011 | Assell et al. |
| 2011/0029019 A1 | 2/2011 | Ainsworth et al. |
| 2011/0040338 A1* | 2/2011 | Jackson ............ A61B 17/7032 606/305 |
| 2011/0040362 A1 | 2/2011 | Godara et al. |
| 2011/0046737 A1 | 2/2011 | Teisen |
| 2011/0060373 A1 | 3/2011 | Russell et al. |
| 2011/0060375 A1 | 3/2011 | Bonutti |
| 2011/0066190 A1 | 3/2011 | Schaller et al. |
| 2011/0082551 A1 | 4/2011 | Kraus |
| 2011/0093020 A1 | 4/2011 | Wu |
| 2011/0098747 A1 | 4/2011 | Donner et al. |
| 2011/0098816 A1 | 4/2011 | Jacob et al. |
| 2011/0098817 A1 | 4/2011 | Eckhardt et al. |
| 2011/0106175 A1 | 5/2011 | Rezach |
| 2011/0153018 A1 | 6/2011 | Walters et al. |
| 2011/0160866 A1 | 6/2011 | Laurence et al. |
| 2011/0178561 A1 | 7/2011 | Roh |
| 2011/0184417 A1 | 7/2011 | Kitch et al. |
| 2011/0184518 A1 | 7/2011 | Trieu |
| 2011/0184519 A1 | 7/2011 | Trieu |
| 2011/0184520 A1 | 7/2011 | Trieu |
| 2011/0196372 A1 | 8/2011 | Murase |
| 2011/0213432 A1 | 9/2011 | Geist et al. |
| 2011/0230966 A1 | 9/2011 | Trieu |
| 2011/0238074 A1 | 9/2011 | Ek |
| 2011/0238124 A1 | 9/2011 | Richelsoph |
| 2011/0238181 A1 | 9/2011 | Trieu |

(56) References Cited

U.S. PATENT DOCUMENTS

| | | |
|---|---|---|
| 2011/0245930 A1 | 10/2011 | Alley et al. |
| 2011/0257755 A1 | 10/2011 | Bellemere et al. |
| 2011/0264229 A1 | 10/2011 | Donner |
| 2011/0276098 A1 | 11/2011 | Biedermann et al. |
| 2011/0295272 A1 | 12/2011 | Assell et al. |
| 2011/0295370 A1 | 12/2011 | Suh et al. |
| 2011/0313471 A1 | 12/2011 | McLean et al. |
| 2011/0313532 A1 | 12/2011 | Hunt |
| 2011/0319995 A1 | 12/2011 | Voellmicke et al. |
| 2012/0004730 A1 | 1/2012 | Castro |
| 2012/0035667 A1 | 2/2012 | Van Nortwick et al. |
| 2012/0083887 A1 | 4/2012 | Purcell et al. |
| 2012/0095560 A1 | 4/2012 | Donner |
| 2012/0179256 A1 | 7/2012 | Reiley |
| 2012/0191191 A1 | 7/2012 | Trieu |
| 2012/0215315 A1 | 8/2012 | Hochschuler et al. |
| 2012/0226318 A1 | 9/2012 | Wenger et al. |
| 2012/0253398 A1 | 10/2012 | Metcalf et al. |
| 2012/0259372 A1 | 10/2012 | Glazer et al. |
| 2012/0271424 A1 | 10/2012 | Crawford |
| 2012/0277866 A1 | 11/2012 | Kalluri et al. |
| 2012/0296428 A1 | 11/2012 | Donner |
| 2012/0323285 A1 | 12/2012 | Assell et al. |
| 2013/0018427 A1 | 1/2013 | Pham et al. |
| 2013/0030456 A1 | 1/2013 | Assell et al. |
| 2013/0030529 A1 | 1/2013 | Hunt |
| 2013/0035727 A1 | 2/2013 | Datta |
| 2013/0053852 A1 | 2/2013 | Greenhalgh et al. |
| 2013/0053854 A1 | 2/2013 | Schoenefeld et al. |
| 2013/0053902 A1 | 2/2013 | Trudeau |
| 2013/0053963 A1 | 2/2013 | Davenport |
| 2013/0072984 A1 | 3/2013 | Robinson |
| 2013/0085535 A1 | 4/2013 | Greenhalgh et al. |
| 2013/0096683 A1 | 4/2013 | Kube |
| 2013/0116793 A1 | 5/2013 | Kloss |
| 2013/0123850 A1 | 5/2013 | Schoenefeld et al. |
| 2013/0123935 A1 | 5/2013 | Hunt et al. |
| 2013/0131678 A1 | 5/2013 | Dahners |
| 2013/0144343 A1 | 6/2013 | Arnett et al. |
| 2013/0158609 A1 | 6/2013 | Mikhail et al. |
| 2013/0172736 A1 | 7/2013 | Abdou |
| 2013/0197590 A1 | 8/2013 | Assell et al. |
| 2013/0203088 A1 | 8/2013 | Baerlecken et al. |
| 2013/0218215 A1 | 8/2013 | Ginn et al. |
| 2013/0218282 A1 | 8/2013 | Hunt |
| 2013/0231746 A1 | 9/2013 | Ginn et al. |
| 2013/0237988 A1 | 9/2013 | Mauldin |
| 2013/0245703 A1 | 9/2013 | Warren et al. |
| 2013/0245763 A1 | 9/2013 | Mauldin |
| 2013/0253595 A1 | 9/2013 | Zucherman et al. |
| 2013/0267836 A1 | 10/2013 | Mauldin et al. |
| 2013/0267961 A1 | 10/2013 | Mauldin et al. |
| 2013/0267989 A1 | 10/2013 | Mauldin et al. |
| 2013/0274890 A1 | 10/2013 | McKay |
| 2013/0325129 A1 | 12/2013 | Huang |
| 2014/0012334 A1 | 1/2014 | Armstrong et al. |
| 2014/0012340 A1 | 1/2014 | Beck et al. |
| 2014/0012384 A1 | 1/2014 | Kana et al. |
| 2014/0031934 A1 | 1/2014 | Trieu |
| 2014/0031935 A1 | 1/2014 | Donner et al. |
| 2014/0031938 A1 | 1/2014 | Lechmann et al. |
| 2014/0031939 A1 | 1/2014 | Wolfe et al. |
| 2014/0046380 A1 | 2/2014 | Asfora |
| 2014/0074175 A1 | 3/2014 | Ehler et al. |
| 2014/0088596 A1 | 3/2014 | Assell et al. |
| 2014/0088707 A1 | 3/2014 | Donner et al. |
| 2014/0121776 A1 | 5/2014 | Hunt |
| 2014/0135927 A1 | 5/2014 | Pavlov et al. |
| 2014/0142700 A1 | 5/2014 | Donner et al. |
| 2014/0172026 A1 | 6/2014 | Biedermann et al. |
| 2014/0172027 A1 | 6/2014 | Biedermann et al. |
| 2014/0200618 A1 | 7/2014 | Donner et al. |
| 2014/0207240 A1 | 7/2014 | Stoffman et al. |
| 2014/0257294 A1 | 9/2014 | Gedet et al. |
| 2014/0257408 A1 | 9/2014 | Trieu et al. |
| 2014/0276846 A1 | 9/2014 | Mauldin et al. |
| 2014/0276851 A1 | 9/2014 | Schneider et al. |
| 2014/0277139 A1 | 9/2014 | Vrionis et al. |
| 2014/0277165 A1 | 9/2014 | Katzman et al. |
| 2014/0277460 A1 | 9/2014 | Schifano et al. |
| 2014/0277462 A1 | 9/2014 | Yerby et al. |
| 2014/0277463 A1 | 9/2014 | Yerby et al. |
| 2014/0288649 A1 | 9/2014 | Hunt |
| 2014/0288650 A1 | 9/2014 | Hunt |
| 2014/0296982 A1 | 10/2014 | Cheng |
| 2014/0330382 A1 | 11/2014 | Mauldin |
| 2014/0364917 A1 | 12/2014 | Sandstrom et al. |
| 2015/0012051 A1 | 1/2015 | Warren et al. |
| 2015/0039037 A1 | 2/2015 | Donner et al. |
| 2015/0080951 A1 | 3/2015 | Yeh |
| 2015/0080972 A1 | 3/2015 | Chin et al. |
| 2015/0094765 A1 | 4/2015 | Donner et al. |
| 2015/0112444 A1 | 4/2015 | Aksu |
| 2015/0147397 A1 | 5/2015 | Altschuler |
| 2015/0150683 A1 | 6/2015 | Donner et al. |
| 2015/0173805 A1 | 6/2015 | Donner et al. |
| 2015/0173904 A1 | 6/2015 | Stark |
| 2015/0182268 A1 | 7/2015 | Donner et al. |
| 2015/0190149 A1 | 7/2015 | Assell et al. |
| 2015/0190187 A1 | 7/2015 | Parent et al. |
| 2015/0209094 A1 | 7/2015 | Anderson |
| 2015/0216566 A1 | 8/2015 | Mikhail et al. |
| 2015/0238203 A1 | 8/2015 | Asfora |
| 2015/0250513 A1 | 9/2015 | De Lavigne Sainte |
| 2015/0250611 A1 | 9/2015 | Schifano et al. |
| 2015/0250612 A1 | 9/2015 | Schifano et al. |
| 2015/0257892 A1 | 9/2015 | Lechmann et al. |
| 2015/0313720 A1 | 11/2015 | Lorio |
| 2015/0320450 A1 | 11/2015 | Mootien et al. |
| 2015/0320451 A1 | 11/2015 | Mootien et al. |
| 2015/0320469 A1 | 11/2015 | Biedermann et al. |
| 2015/0342753 A1 | 12/2015 | Donner et al. |
| 2016/0000488 A1 | 1/2016 | Cross, III |
| 2016/0022429 A1 | 1/2016 | Greenhalgh et al. |
| 2016/0095711 A1 | 4/2016 | Castro |
| 2016/0095721 A1 | 4/2016 | Schell et al. |
| 2016/0100870 A1 | 4/2016 | Lavigne et al. |
| 2016/0106477 A1 | 4/2016 | Hynes et al. |
| 2016/0106479 A1 | 4/2016 | Hynes et al. |
| 2016/0120661 A1 | 5/2016 | Schell et al. |
| 2016/0143671 A1 | 5/2016 | Jimenez |
| 2016/0157908 A1 | 6/2016 | Cawley et al. |
| 2016/0166291 A1 | 6/2016 | Goel et al. |
| 2016/0166301 A1 | 6/2016 | Papangelou et al. |
| 2016/0175113 A1 | 6/2016 | Lins |
| 2016/0184103 A1 | 6/2016 | Fonte et al. |
| 2016/0213487 A1 | 7/2016 | Wilson et al. |
| 2016/0242820 A1 | 8/2016 | Whipple et al. |
| 2016/0242912 A1 | 8/2016 | Lindsey et al. |
| 2016/0249940 A1 | 9/2016 | Stark |
| 2016/0287171 A1 | 10/2016 | Sand et al. |
| 2016/0287301 A1 | 10/2016 | Mehl et al. |
| 2016/0310188 A1 | 10/2016 | Marino et al. |
| 2016/0310197 A1 | 10/2016 | Black et al. |
| 2016/0324643 A1 | 11/2016 | Donner et al. |
| 2016/0324656 A1 | 11/2016 | Morris et al. |
| 2016/0374727 A1 | 12/2016 | Greenhalgh et al. |
| 2017/0014235 A1 | 1/2017 | Jones et al. |
| 2017/0020573 A1 | 1/2017 | Cain et al. |
| 2017/0020585 A1 | 1/2017 | Harshman et al. |
| 2017/0049488 A1 | 2/2017 | Vestgaarden |
| 2017/0086885 A1 | 3/2017 | Duncan et al. |
| 2017/0128083 A1 | 5/2017 | Germain |
| 2017/0128214 A1 | 5/2017 | Mayer |
| 2017/0135733 A1 | 5/2017 | Donner et al. |
| 2017/0135737 A1 | 5/2017 | Krause |
| 2017/0143513 A1 | 5/2017 | Sandstrom et al. |
| 2017/0156879 A1 | 6/2017 | Janowski |
| 2017/0156880 A1 | 6/2017 | Halverson et al. |
| 2017/0202511 A1 | 7/2017 | Chang et al. |
| 2017/0209155 A1 | 7/2017 | Petersen |
| 2017/0216036 A1 | 8/2017 | Cordaro |
| 2017/0224393 A1 | 8/2017 | Lavigne et al. |
| 2017/0246000 A1 | 8/2017 | Pavlov et al. |

(56) References Cited

U.S. PATENT DOCUMENTS

| | | |
|---|---|---|
| 2017/0258498 A1 | 9/2017 | Redmond et al. |
| 2017/0258506 A1 | 9/2017 | Redmond et al. |
| 2017/0258606 A1 | 9/2017 | Afzal |
| 2017/0266007 A1 | 9/2017 | Gelaude et al. |
| 2017/0296344 A1 | 10/2017 | Souza et al. |
| 2017/0303938 A1 | 10/2017 | Rindal et al. |
| 2017/0333205 A1 | 11/2017 | Joly et al. |
| 2017/0348034 A1 | 12/2017 | LaPierre et al. |
| 2017/0354442 A1 | 12/2017 | Kim et al. |
| 2017/0360570 A1 | 12/2017 | Berndt et al. |
| 2018/0008256 A1 | 1/2018 | Fallin et al. |
| 2018/0036041 A1 | 2/2018 | Pham et al. |
| 2018/0042652 A1 | 2/2018 | Mari et al. |
| 2018/0042735 A1 | 2/2018 | Schell et al. |
| 2018/0092677 A1 | 4/2018 | Peterson et al. |
| 2018/0104063 A1 | 4/2018 | Asaad |
| 2018/0104068 A1 | 4/2018 | Sack |
| 2018/0110624 A1 | 4/2018 | Amone |
| 2018/0110626 A1 | 4/2018 | McShane, III et al. |
| 2018/0200063 A1 | 7/2018 | Kahmer et al. |
| 2018/0214192 A1 | 8/2018 | Roby et al. |
| 2018/0228613 A1 | 8/2018 | Jones et al. |
| 2018/0228617 A1 | 8/2018 | Srour et al. |
| 2018/0228621 A1 | 8/2018 | Reiley et al. |
| 2018/0235643 A1 | 8/2018 | Lins et al. |
| 2018/0243097 A1 | 8/2018 | Jones et al. |
| 2018/0256232 A1 | 9/2018 | Russell |
| 2018/0256351 A1 | 9/2018 | Bishop et al. |
| 2018/0256352 A1 | 9/2018 | Nyahay et al. |
| 2018/0256361 A1 | 9/2018 | Bishop et al. |
| 2018/0280139 A1 | 10/2018 | Jones et al. |
| 2018/0280140 A1 | 10/2018 | Jones et al. |
| 2018/0289504 A1 | 10/2018 | Arthurs et al. |
| 2018/0296227 A1 | 10/2018 | Meek et al. |
| 2018/0296347 A1 | 10/2018 | Hamzey et al. |
| 2018/0296363 A1 | 10/2018 | Berry |
| 2018/0303520 A1 | 10/2018 | Rajpal |
| 2018/0303623 A1 | 10/2018 | Shoshtaev |
| 2018/0303624 A1 | 10/2018 | Shoshtaev |
| 2018/0317971 A1 | 11/2018 | Prevost |
| 2018/0360512 A1 | 12/2018 | Mari |
| 2018/0368894 A1 | 12/2018 | Wieland et al. |
| 2019/0000636 A1 | 1/2019 | Kim et al. |
| 2019/0008562 A1 | 1/2019 | Melton et al. |
| 2019/0046684 A1 | 2/2019 | Roth |
| 2019/0076258 A1 | 3/2019 | Black et al. |
| 2019/0076266 A1 | 3/2019 | Trudeau et al. |
| 2019/0083270 A1 | 3/2019 | Milz et al. |
| 2019/0091027 A1 | 3/2019 | Asaad et al. |
| 2019/0117827 A1 | 4/2019 | Roth |
| 2019/0125371 A1 | 5/2019 | Asfora et al. |
| 2019/0125408 A1 | 5/2019 | Asfora et al. |
| 2019/0133613 A1 | 5/2019 | Reiley et al. |
| 2019/0133769 A1 | 5/2019 | Tetsworth et al. |
| 2019/0133783 A1 | 5/2019 | Unger et al. |
| 2019/0142606 A1 | 5/2019 | Freudenberger |
| 2019/0150910 A1 | 5/2019 | Jones et al. |
| 2019/0151113 A1 | 5/2019 | Sack |
| 2019/0151114 A1 | 5/2019 | Sack |
| 2019/0167326 A1 | 6/2019 | Greenhalgh et al. |
| 2019/0183653 A1 | 6/2019 | Gregersen et al. |
| 2019/0231554 A1 | 8/2019 | Bishop et al. |
| 2019/0239935 A1 | 8/2019 | Willis et al. |
| 2019/0247094 A1 | 8/2019 | Yacoub et al. |
| 2019/0254840 A1 | 8/2019 | Gray et al. |
| 2019/0262048 A1 | 8/2019 | Sutika |
| 2019/0262049 A1 | 8/2019 | Tempco et al. |
| 2019/0290441 A1 | 9/2019 | Tong et al. |
| 2019/0298528 A1 | 10/2019 | Lindsey et al. |
| 2019/0298542 A1 | 10/2019 | Kloss |
| 2019/0328546 A1 | 10/2019 | Palagi et al. |
| 2019/0343564 A1 | 11/2019 | Tempco et al. |
| 2019/0343565 A1 | 11/2019 | Tempco et al. |
| 2019/0343566 A1 | 11/2019 | Tempco et al. |
| 2019/0343567 A1 | 11/2019 | Tempco et al. |
| 2019/0343640 A1 | 11/2019 | Donner et al. |
| 2019/0343641 A1 | 11/2019 | Mauldin et al. |
| 2019/0343644 A1 | 11/2019 | Ryan et al. |
| 2019/0343645 A1 | 11/2019 | Miccio et al. |
| 2019/0343652 A1 | 11/2019 | Petersheim et al. |
| 2019/0343653 A1 | 11/2019 | McKay |
| 2019/0388131 A1 | 12/2019 | Mehl et al. |
| 2019/0388228 A1 | 12/2019 | Donner et al. |
| 2019/0388242 A1 | 12/2019 | Harris et al. |
| 2020/0000595 A1 | 1/2020 | Jones et al. |
| 2020/0008817 A1 | 1/2020 | Reiley et al. |
| 2020/0022817 A1 | 1/2020 | Crossgrove et al. |
| 2020/0038069 A1 | 2/2020 | Jones et al. |
| 2020/0046512 A1 | 2/2020 | Newman et al. |
| 2020/0069431 A1 | 3/2020 | Boehm et al. |
| 2020/0093603 A1 | 3/2020 | Manwill et al. |
| 2020/0100822 A1 | 4/2020 | Lipow |
| 2020/0129214 A1 | 4/2020 | Pepper et al. |
| 2020/0138485 A1 | 5/2020 | Kuwamura et al. |
| 2020/0138492 A1 | 5/2020 | Kavanagh |
| 2020/0146721 A1 | 5/2020 | Sadiq |
| 2020/0149137 A1 | 5/2020 | Roth |
| 2020/0170679 A1 | 6/2020 | Sciubba et al. |
| 2020/0206390 A1 | 7/2020 | Roth |
| 2020/0222088 A1 | 7/2020 | Kraus |
| 2020/0222195 A1 | 7/2020 | Assell et al. |
| 2020/0246158 A1 | 8/2020 | Bergey |
| 2020/0254140 A1 | 8/2020 | Roth |
| 2020/0268449 A1 | 8/2020 | Solitro et al. |
| 2020/0268518 A1 | 8/2020 | Suh et al. |
| 2020/0276019 A1 | 9/2020 | Shetty et al. |
| 2020/0281729 A1 | 9/2020 | Schifano et al. |
| 2020/0297496 A1 | 9/2020 | Mullin |
| 2020/0305896 A1 | 10/2020 | Castro |
| 2020/0315647 A1 | 10/2020 | Fojtik et al. |
| 2020/0315666 A1 | 10/2020 | Nichols et al. |
| 2020/0315669 A1 | 10/2020 | Dejardin |
| 2020/0323563 A1 | 10/2020 | Rezach et al. |
| 2020/0345507 A1 | 11/2020 | Reiley |
| 2020/0345508 A1 | 11/2020 | Reiley |
| 2020/0345509 A1 | 11/2020 | Reiley |
| 2020/0345510 A1 | 11/2020 | Reiley |
| 2020/0375750 A1 | 12/2020 | Abbasi et al. |
| 2020/0397491 A1 | 12/2020 | Frey et al. |
| 2021/0022882 A1 | 1/2021 | Dang et al. |
| 2021/0085470 A1 | 3/2021 | Ty |
| 2021/0107093 A1 | 4/2021 | Tempco |
| 2021/0153911 A1 | 5/2021 | Stuart et al. |
| 2021/0169660 A1 | 6/2021 | Reckling et al. |
| 2021/0196332 A1 | 7/2021 | Patel |
| 2021/0212734 A1 | 7/2021 | Mesiwala et al. |
| 2021/0212833 A1 | 7/2021 | Chin et al. |
| 2021/0228360 A1 | 7/2021 | Hunt et al. |
| 2021/0228363 A1 | 7/2021 | Suddaby |
| 2021/0236146 A1 | 8/2021 | Donner et al. |
| 2021/0244449 A1 | 8/2021 | Castro |
| 2021/0244452 A1 | 8/2021 | Castro |
| 2021/0275233 A1 | 9/2021 | Fang et al. |
| 2021/0338454 A1 | 11/2021 | Afzal |
| 2021/0346038 A1 | 11/2021 | Fiechter et al. |
| 2021/0353337 A1 | 11/2021 | Kaufmann et al. |
| 2021/0353338 A1 | 11/2021 | Meek et al. |
| 2021/0393298 A1 | 12/2021 | Castro |
| 2021/0393408 A1 | 12/2021 | Ginn |
| 2021/0393409 A1 | 12/2021 | Ginn |
| 2022/0031365 A1 | 2/2022 | Suh et al. |
| 2022/0031474 A1 | 2/2022 | Reckling et al. |
| 2022/0096098 A1 | 3/2022 | Sand et al. |
| 2022/0117640 A1 | 4/2022 | Schneider et al. |
| 2022/0151668 A1 | 5/2022 | Mauldin et al. |
| 2022/0273447 A1 | 9/2022 | Ginn |
| 2022/0273448 A1 | 9/2022 | Ginn et al. |
| 2022/0296377 A1 | 9/2022 | Ginn et al. |
| 2022/0296378 A1 | 9/2022 | Ginn |
| 2022/0304672 A1 | 9/2022 | Kalhorn et al. |
| 2022/0304813 A1 | 9/2022 | Ginn et al. |
| 2022/0304814 A1 | 9/2022 | Ginn |
| 2022/0361924 A1 | 11/2022 | Castro |
| 2022/0409381 A1 | 12/2022 | Ginn |

(56) References Cited

U.S. PATENT DOCUMENTS

| | | |
|---|---|---|
| 2023/0000630 A1 | 1/2023 | Ginn et al. |
| 2023/0000631 A1 | 1/2023 | Ginn et al. |
| 2023/0076180 A1 | 3/2023 | Schifano et al. |
| 2023/0088477 A1 | 3/2023 | Roussouly et al. |
| 2023/0145974 A1 | 5/2023 | Asfora |
| 2023/0190442 A1 | 6/2023 | Castro |
| 2023/0263553 A1 | 8/2023 | Compton et al. |
| 2023/0263554 A1 | 8/2023 | Stuart et al. |
| 2023/0270559 A1 | 8/2023 | Mesiwala et al. |
| 2023/0285054 A1 | 9/2023 | Mehl et al. |
| 2023/0293206 A1 | 9/2023 | Mundis et al. |
| 2023/0321317 A1 | 10/2023 | Suh |
| 2023/0329765 A1 | 10/2023 | Lavigne et al. |
| 2023/0390078 A1 | 12/2023 | Bergey et al. |
| 2023/0404762 A1 | 12/2023 | Ginn et al. |
| 2024/0050131 A1 | 2/2024 | Bannigan et al. |
| 2024/0081873 A1 | 3/2024 | Gilbride |
| 2024/0252717 A1 | 8/2024 | Suh et al. |
| 2024/0261107 A1 | 8/2024 | Ginn et al. |
| 2024/0285410 A1 | 8/2024 | Ginn et al. |
| 2024/0366401 A1 | 11/2024 | Bergey |
| 2024/0374399 A1 | 11/2024 | Stuart et al. |
| 2024/0390151 A1 | 11/2024 | Ginn et al. |
| 2024/0398453 A1 | 12/2024 | Mauldin et al. |
| 2024/0415547 A1 | 12/2024 | Wentz et al. |
| 2025/0009396 A1 | 1/2025 | Vestgaarden |
| 2025/0025309 A1 | 1/2025 | Casey |
| 2025/0099259 A1 | 3/2025 | Cordaro |

FOREIGN PATENT DOCUMENTS

| | | |
|---|---|---|
| CN | 1909848 A | 2/2007 |
| CN | 101795632 A | 8/2010 |
| CN | 102361601 A | 2/2012 |
| CN | 102429716 A | 5/2012 |
| CN | 104968283 A | 10/2015 |
| CN | 109124748 A | 6/2017 |
| DE | 102011001264 A1 | 9/2012 |
| DE | 102012106336 A1 | 1/2014 |
| EP | 1287796 A1 | 3/2003 |
| EP | 2070481 B1 | 2/2012 |
| EP | 2796104 A1 | 10/2014 |
| EP | 2590576 B1 | 10/2015 |
| EP | 2749238 B1 | 3/2017 |
| EP | 2887899 B1 | 8/2017 |
| EP | 2341852 B1 | 8/2018 |
| EP | 2496162 B1 | 10/2018 |
| EP | 3484387 A1 | 5/2019 |
| EP | 3501457 A1 | 6/2019 |
| EP | 356044/8 A1 | 10/2019 |
| EP | 3593745 A2 | 1/2020 |
| EP | 3616634 A1 | 3/2020 |
| EP | 3661441 A1 | 6/2020 |
| EP | 2408389 B1 | 4/2021 |
| JP | 59200642 A | 11/1984 |
| JP | 05-176942 A | 7/1993 |
| JP | 05184615 A | 7/1993 |
| JP | 09149906 A | 10/1997 |
| JP | 10-85231 A | 4/1998 |
| JP | 11318931 A | 11/1999 |
| JP | 2002509753 A | 4/2002 |
| JP | 2003511198 A | 3/2003 |
| JP | 2003533329 A | 11/2003 |
| JP | 2003534046 A | 11/2003 |
| JP | 2004121841 | 4/2004 |
| JP | 2004512895 | 4/2004 |
| JP | 2004516866 | 6/2004 |
| JP | 2006506181 | 2/2006 |
| JP | 2007535973 A | 12/2007 |
| JP | 2008540036 A | 11/2008 |
| JP | 2009000501 A | 1/2009 |
| JP | 2009521990 A | 6/2009 |
| JP | 2009533159 A | 9/2009 |
| JP | 2010137016 A | 6/2010 |
| JP | 2011041802 A | 3/2011 |
| JP | 2011512939 A | 4/2011 |
| JP | 2012030105 A | 2/2012 |
| JP | 2014000402 A | 1/2014 |
| JP | 2014147820 A | 8/2014 |
| JP | 2015510506 A | 4/2015 |
| JP | 2015171520 A | 10/2015 |
| JP | 2015531282 A | 11/2015 |
| JP | 2016515857 A | 6/2016 |
| JP | 2017528251 A | 9/2017 |
| JP | 2017533759 A | 11/2017 |
| JP | 2019506993 A | 3/2019 |
| KR | 102537768 B1 | 5/2023 |
| WO | WO97/31517 A2 | 8/1997 |
| WO | WO01/17445 A1 | 3/2001 |
| WO | WO02/38054 | 5/2002 |
| WO | WO03/007839 A2 | 1/2003 |
| WO | WO04/02344 | 1/2004 |
| WO | WO2004/043277 A1 | 5/2004 |
| WO | WO2005/009729 A2 | 2/2005 |
| WO | WO2006/003316 | 1/2006 |
| WO | WO2006/023793 A2 | 3/2006 |
| WO | WO2006/074321 A2 | 7/2006 |
| WO | WO2006/116850 A1 | 11/2006 |
| WO | WO2008/153723 A1 | 12/2008 |
| WO | WO2009/025884 A2 | 2/2009 |
| WO | WO2009/029074 A1 | 3/2009 |
| WO | WO2010/105196 A1 | 9/2010 |
| WO | WO2011/010463 A1 | 1/2011 |
| WO | WO2011/110865 A2 | 9/2011 |
| WO | WO2011/124874 A1 | 10/2011 |
| WO | WO2011/149557 A1 | 12/2011 |
| WO | WO2012/015976 A1 | 2/2012 |
| WO | WO2012/048008 A1 | 4/2012 |
| WO | WO2013/000071 A1 | 1/2013 |
| WO | WO2013/052807 A2 | 4/2013 |
| WO | WO2013/119907 A1 | 8/2013 |
| WO | WO2013/134678 A1 | 9/2013 |
| WO | WO2014/145902 A1 | 9/2014 |
| WO | WO2017/147140 A1 | 8/2017 |
| WO | WO2017/147537 A1 | 8/2017 |
| WO | WO2017/201371 A1 | 11/2017 |
| WO | WO2019/152737 A1 | 8/2019 |
| WO | WO2020/168269 A1 | 8/2020 |

OTHER PUBLICATIONS

Al-Khayer et al.; Percutaneous sacroiliac joint arthrodesis, a novel technique; J Spinal Disord Tech; vol. 21; No. 5; pp. 359-363; Jul. 2008.

Khurana et al.; Percutaneous fusion of the sacroiliac joint with hollow modular anchorage screws, clinical and radiological outcome; J Bone Joint Surg; vol. 91-B; No. 5; pp. 627-631; May 2009.

Lu et al.; Mechanical properties of porous materials; Journal of Porous Materials; 6(4); pp. 359-368; Nov. 1, 1999.

Peretz et al.; The internal bony architecture of the sacrum; Spine; 23(9); pp. 971-974; May 1, 1998.

Richards et al.; Bone density and cortical thickness in normal, osteopenic, and osteoporotic sacra; Journal of Osteoporosis; 2010(ID 504078); 5 pgs; Jun. 9, 2010.

Wise et al.; Minimally invasive sacroiliac arthrodesis, outcomes of a new technique; J Spinal Disord Tech; vol. 21; No. 8; pp. 579-584; Dec. 2008.

Mesiwala et al.; U.S. Appl. No. 17/649,265 entitled "Implants for spinal fixation and or fusion," filed Jan. 28, 2022.

Mesiwala et al.; U.S. Appl. No. 17/649,296 entitled "Implants for spinal fixation and or fusion," filed Jan. 28, 2022.

Mauldin et al.; U.S. Appl. No. 17/650,473 entitled "Fenestrated implant," filed Feb. 9, 2022.

Stuart et al.; U.S. Appl. No. 17/664,353 entitled "Bone stabilizing implants and methods of placement across SI joints," filed May 20, 2022.

Mauldin et al.; U.S. Appl. No. 17/664,582 entitled "Integrated implant," filed May 23, 2022.

Stuart et al.; U.S. Appl. No. 17/812,945 entitled "Sacro-iliac joint stabilizing implants and methods of implantation," filed Jul. 15, 2022.

(56) References Cited

OTHER PUBLICATIONS

Mauldin et al.; U.S. Appl. No. 17/822,360 entitled "Fenestrated implant," filed Aug. 25, 2022.
Mauldin et al.; U.S. Appl. No. 18/509,864 entitled "Systems, device, and methods for joint fusion," filed Nov. 15, 2023.
Sand et al.; U.S. Appl. No. 18/527,030 entitled "Systems and methods for decorticating the sacroiliac joint," filed Dec. 1, 2023.
Lindsey et al.; U.S. Appl. No. 18/066,872 entitled "Threaded implants and methods of use across bone segments," filed Dec. 15, 2022.
Mauldin et al.; U.S. Appl. No. 17/805,165 entitled "Systems, device, and methods for joint fusion," filed Jun. 2, 2022.
Mesiwala et al.; U.S. Appl. No. 18/632,102 entitled "Implants for spinal fixation or fusion," filed Apr. 10, 2024.
Mesiwala et al.; U.S. Appl. No. 18/716,090 entitled "Fusion cages and methods for sacro-iliac joint stabilization," filed Jun. 3, 2024.
Reiley et al.; U.S. Appl. No. 18/317,832 entitled "Implants for bone fixation or fusion," filed May 15, 2023.
Stuart et al.; U.S. Appl. No. 18/356,880 entitled "Sacro-iliac join stabilizing implants and methods of implantation," filed Jul. 21, 2023.
Thiesen et at.; The three-dimensional bone mass distribution of the posterior pelvic ring and its key role in transsacral screw placement; Scientific Reports; 10(1); doi.org/10.1038/s41598-020-61954-8; 8 pages; Mar. 2020.
Stuart et al.; U.S. Appl. No. 18/805,412 entitled "Pelvic stabilization implants, methods of use and manufacture," filed Aug. 14, 2024.
Reckling et al.; U.S. Appl. No. 18/809,229 entitled "Sacro-iliac joint stabilizing implants and methods of implantation," filed Aug. 19, 2024.
Mesiwala et al.; U.S. Appl. No. 18/810,211 entitled "Implants for spinal fixation and or fusion," filed Aug. 20, 2024.
Schneider et al.; U.S. Appl. No. 18/927,238 entitled "Matrix implant," filed Oct. 25, 2024.

* cited by examiner

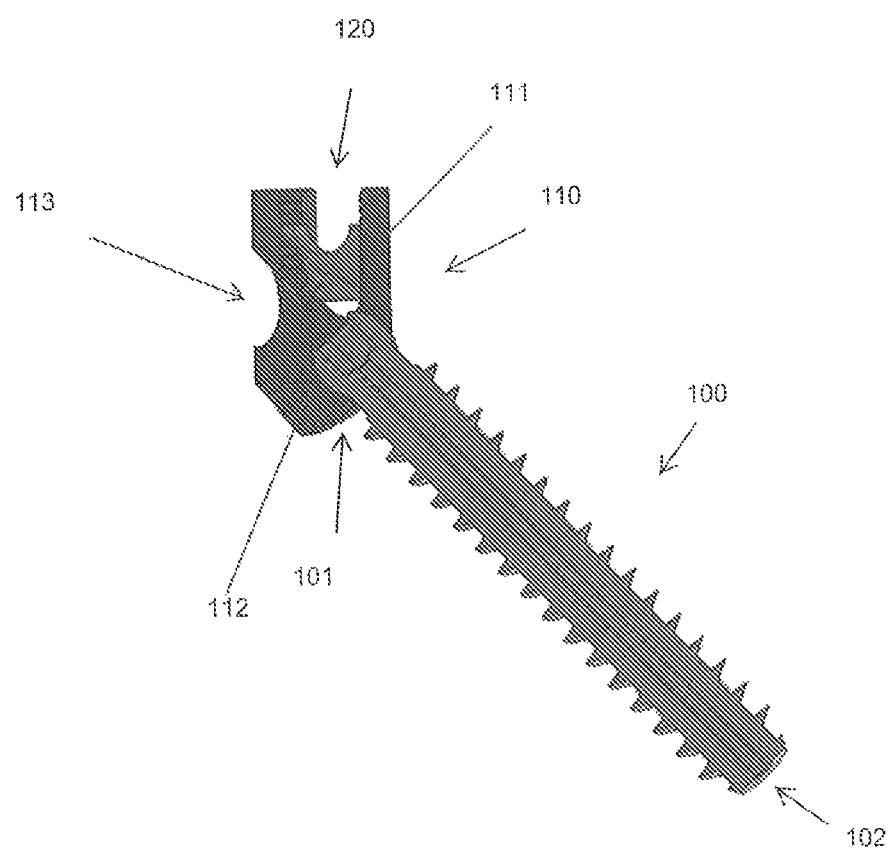

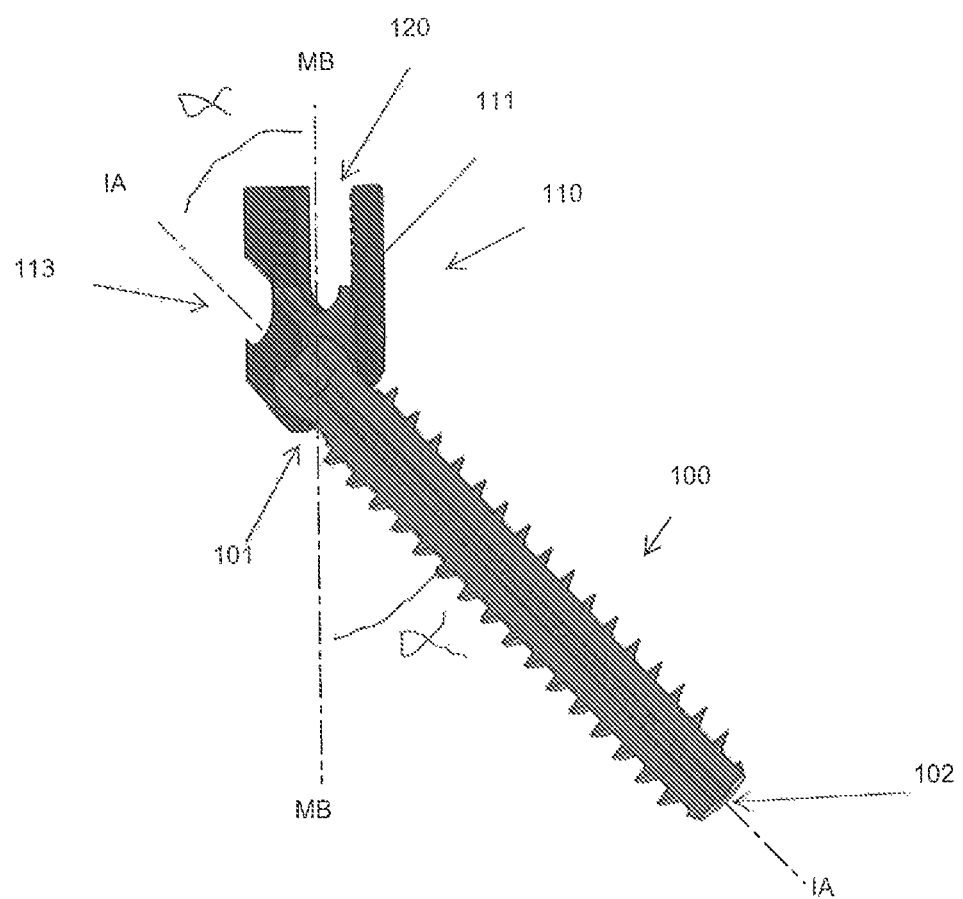

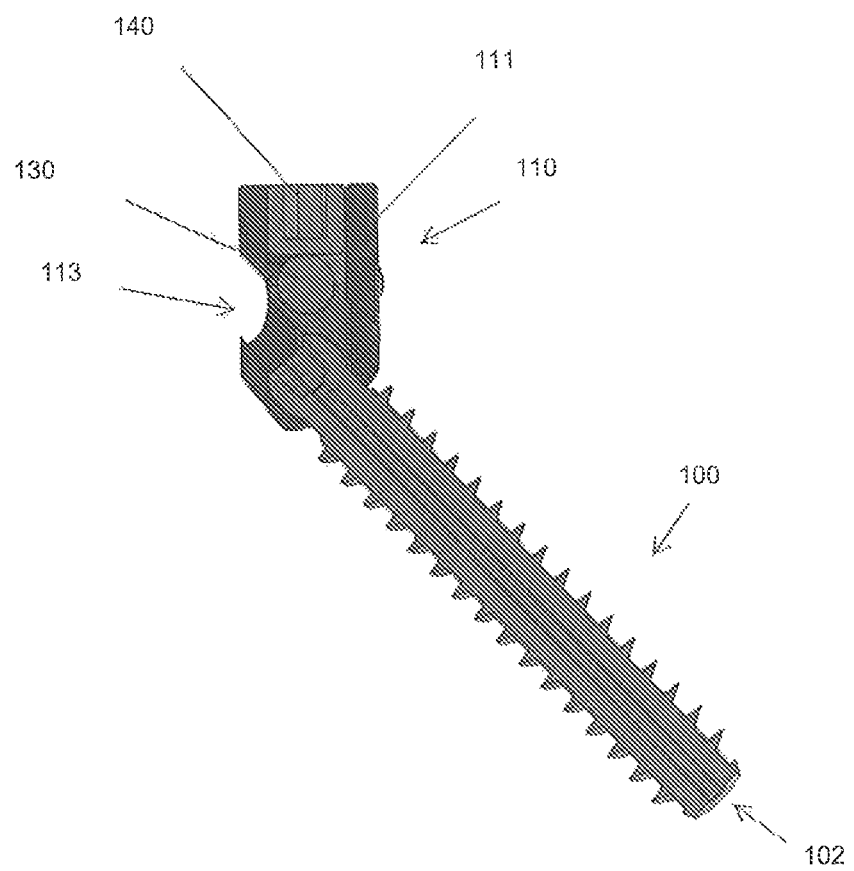

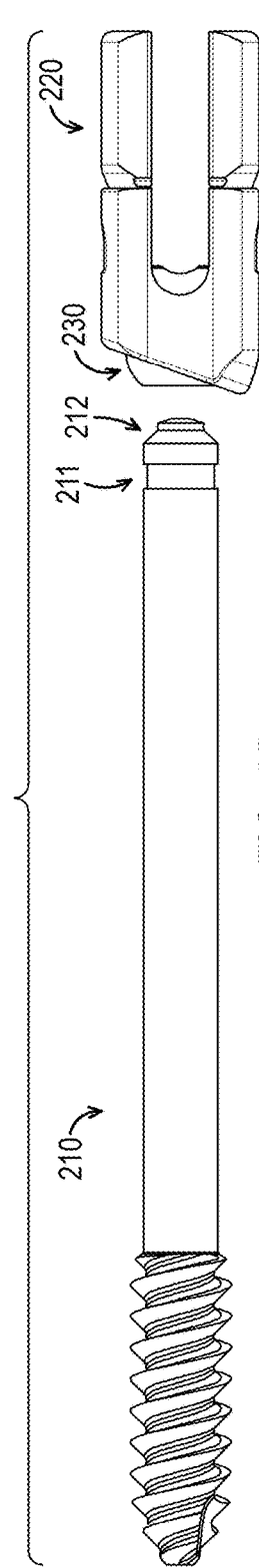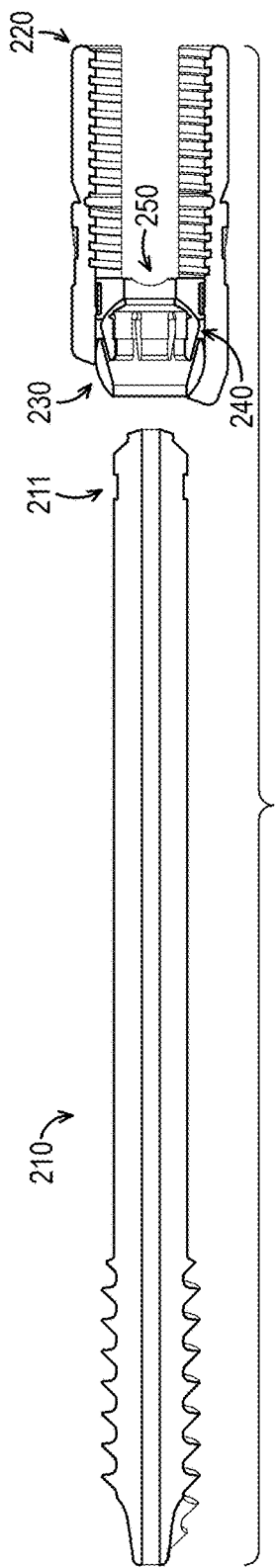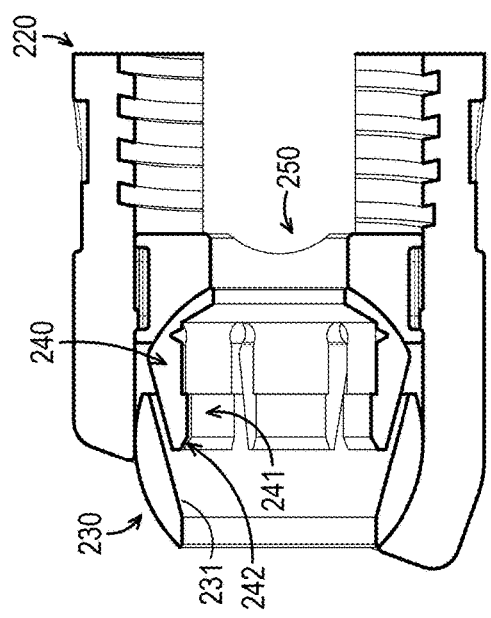
FIG. 2B
FIG. 2C
FIG. 2D

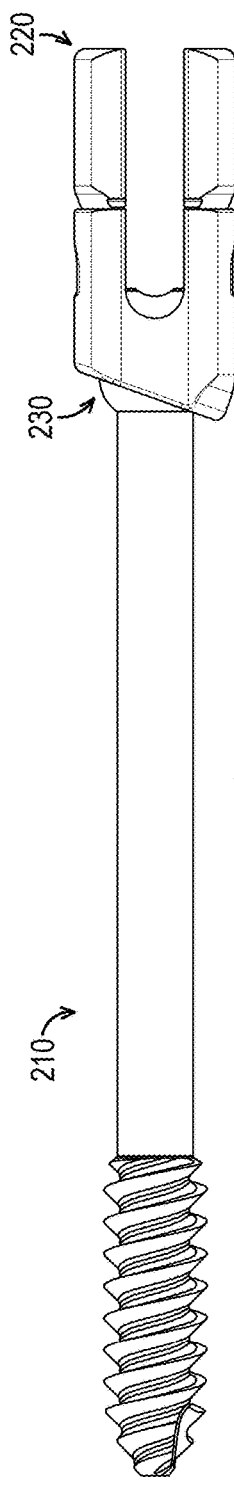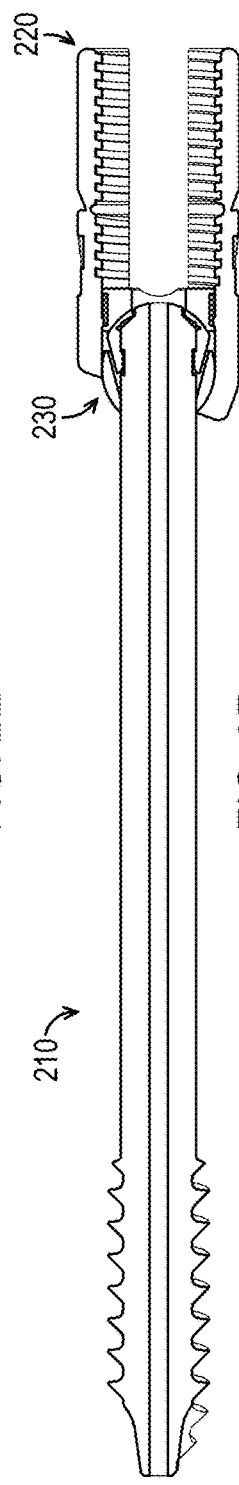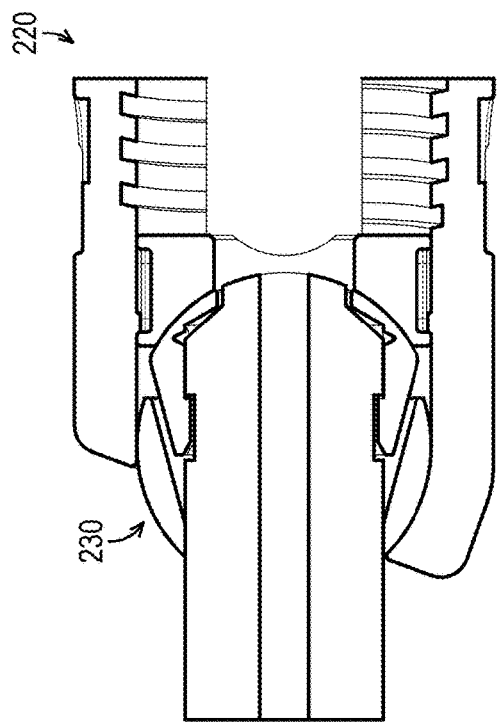
FIG. 2E
FIG. 2F
FIG. 2G

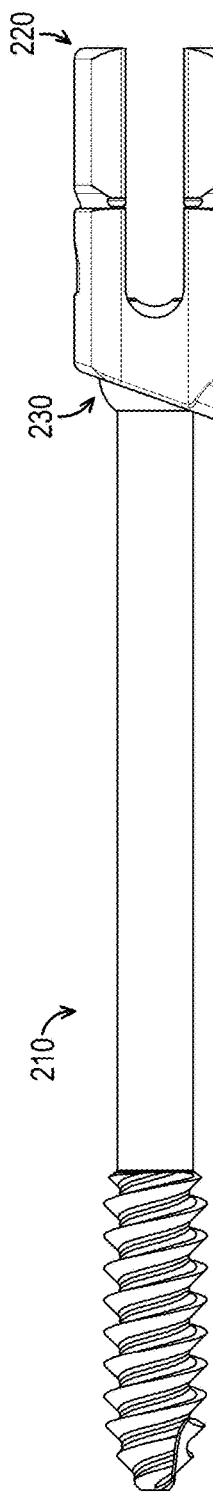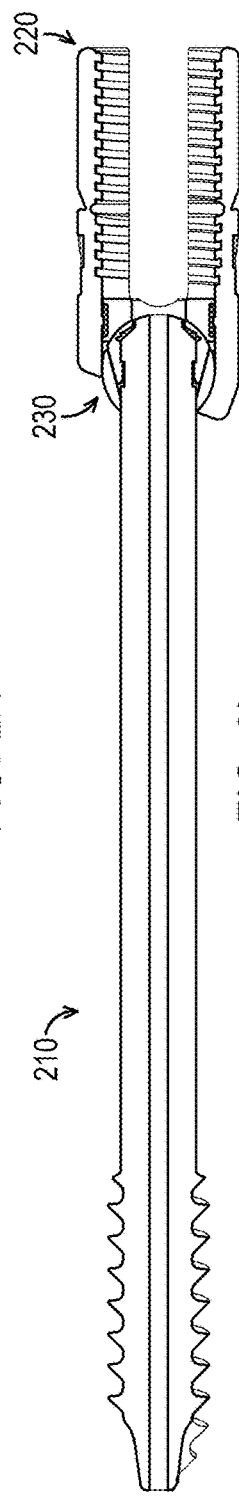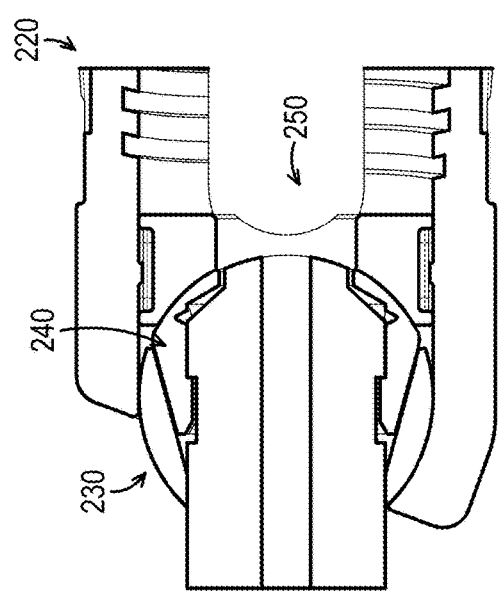

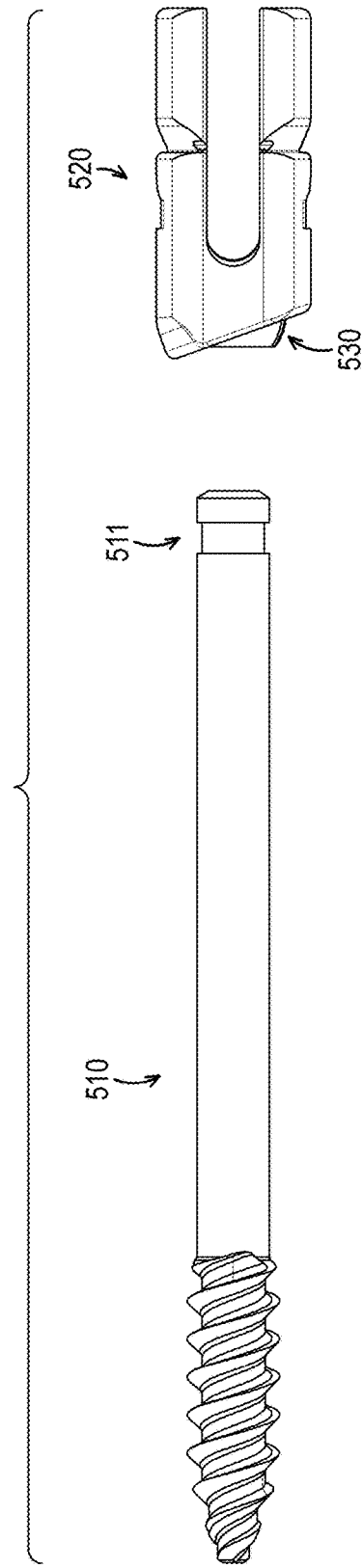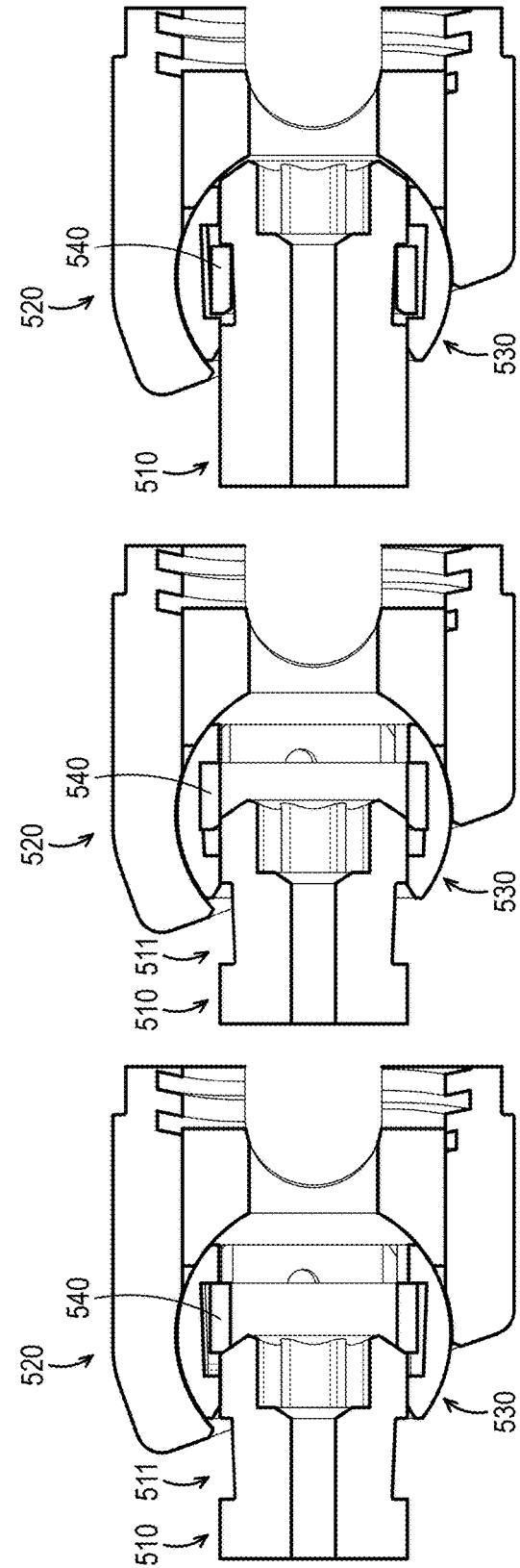
FIG. 5A
FIG. 5B
FIG. 5C
FIG. 5D

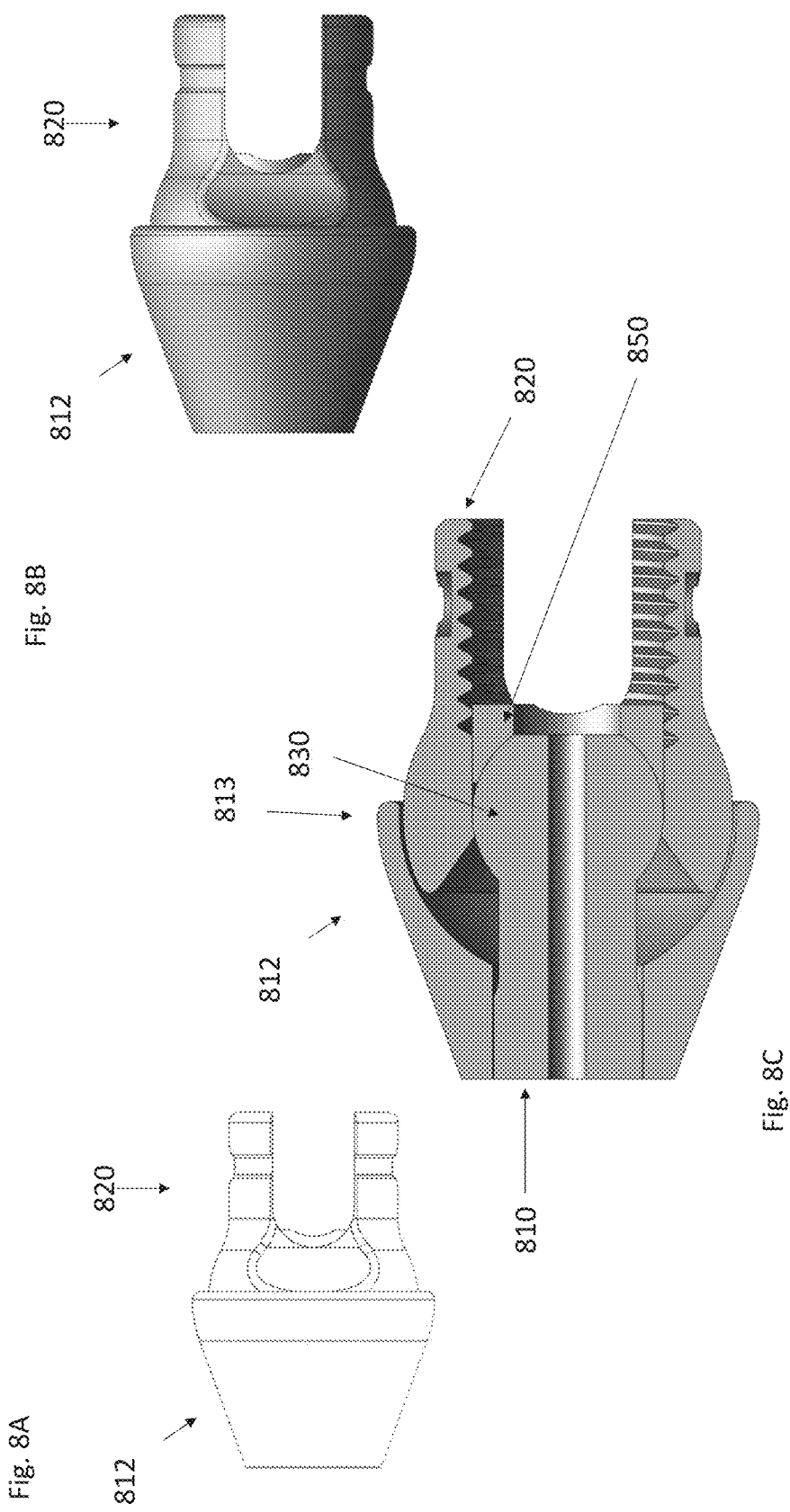

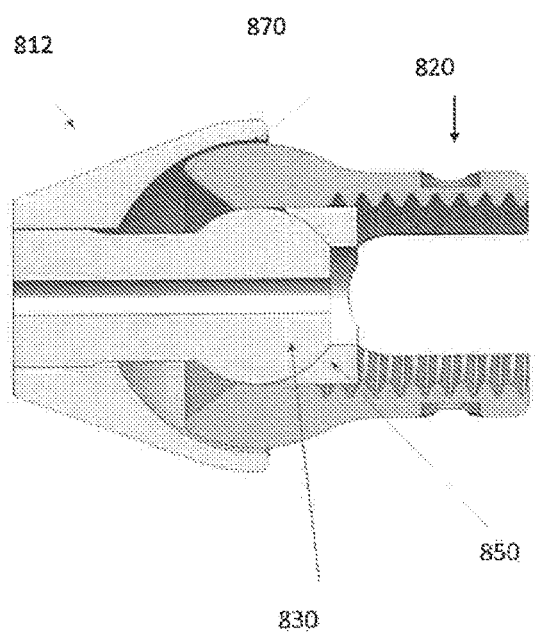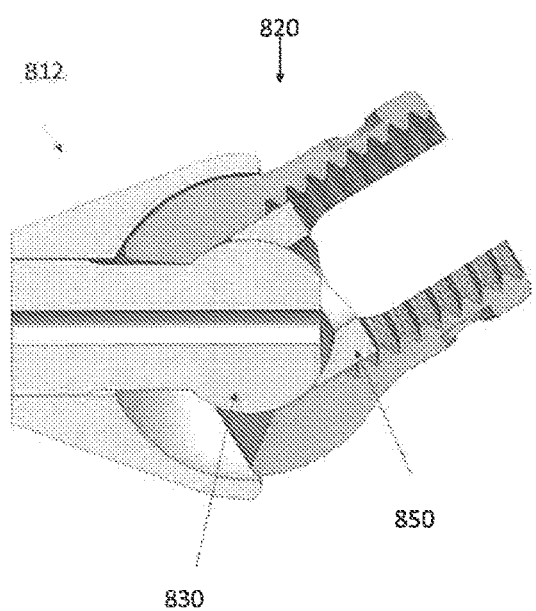
Fig. 8D
Fig. 8E

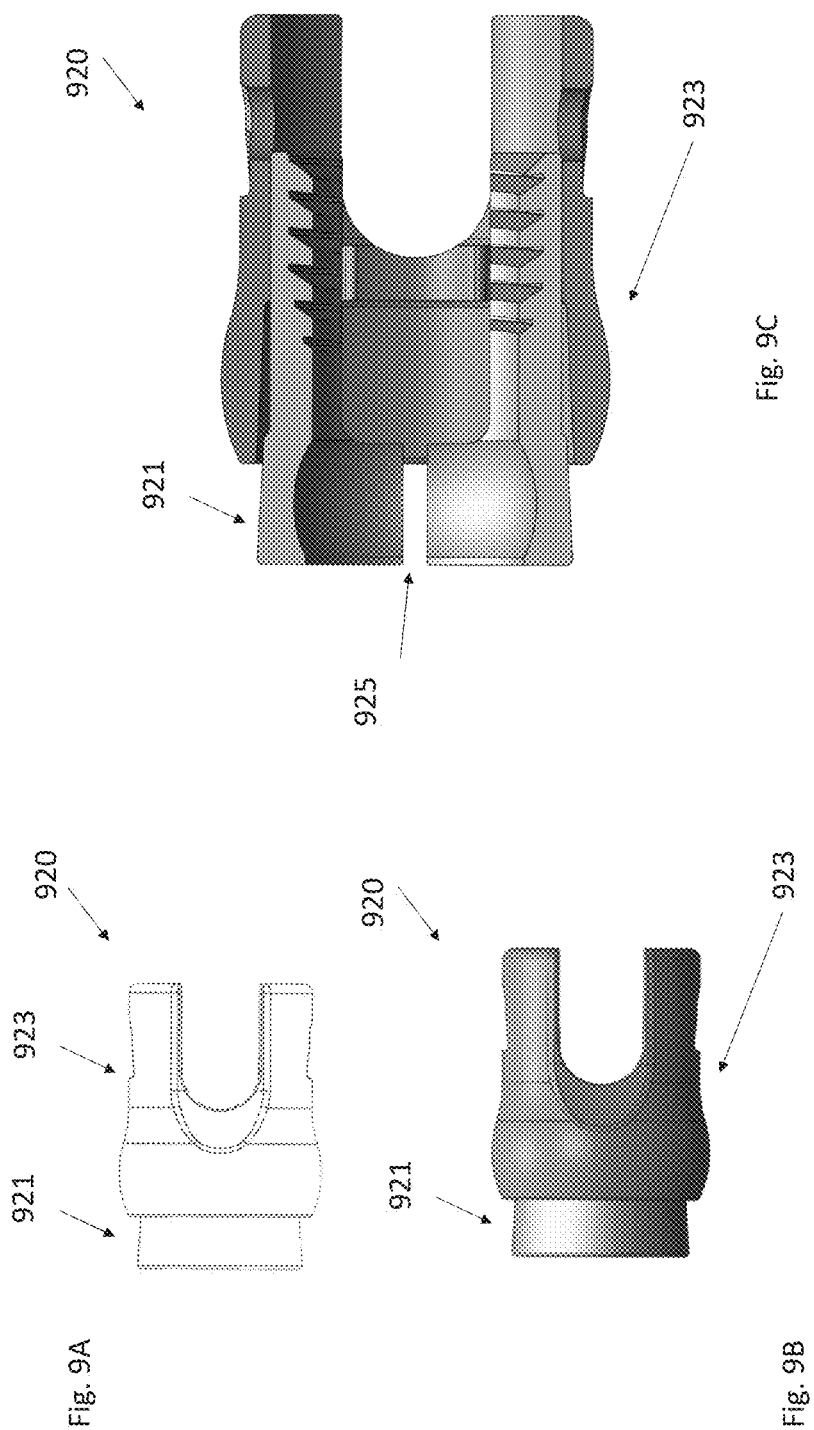

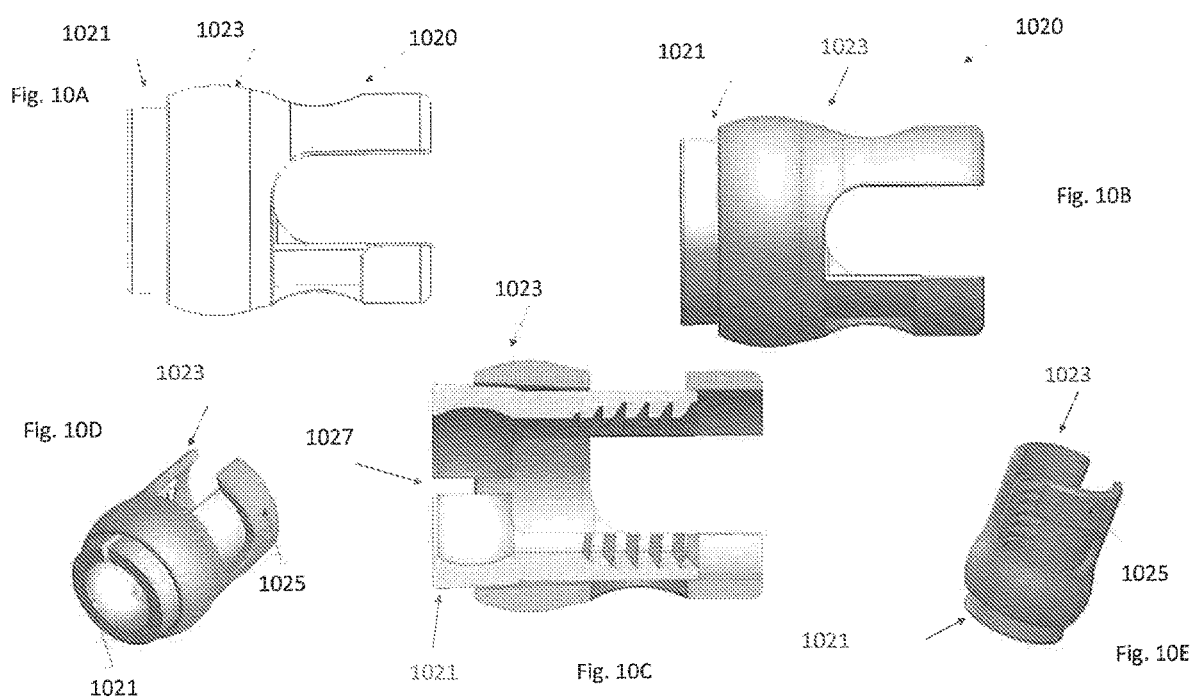

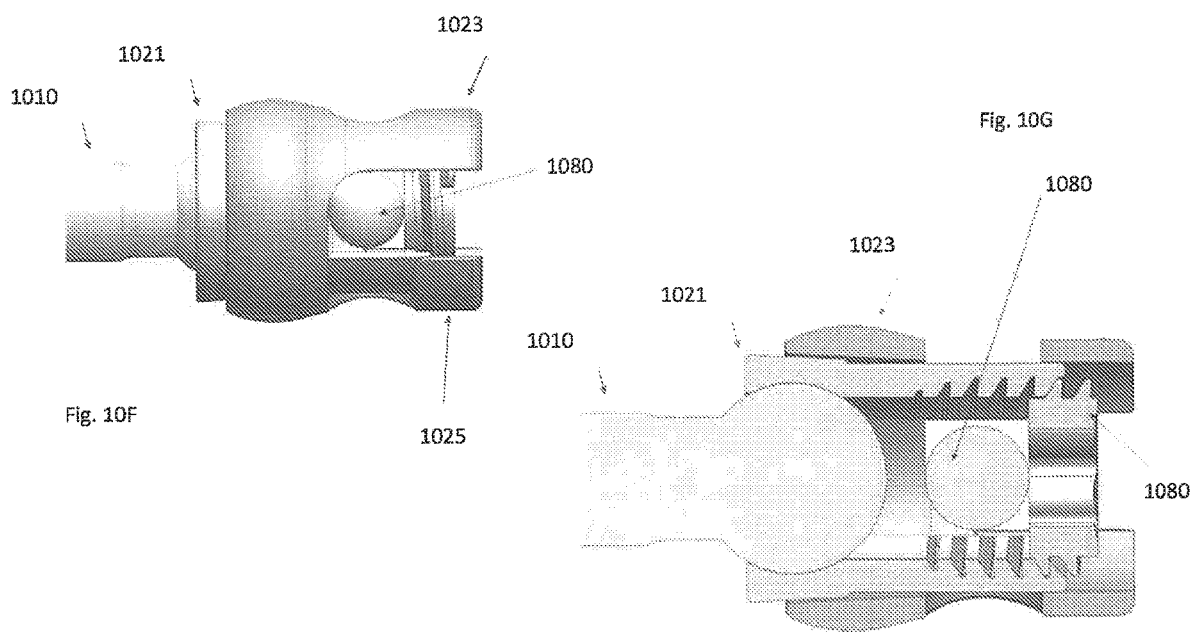

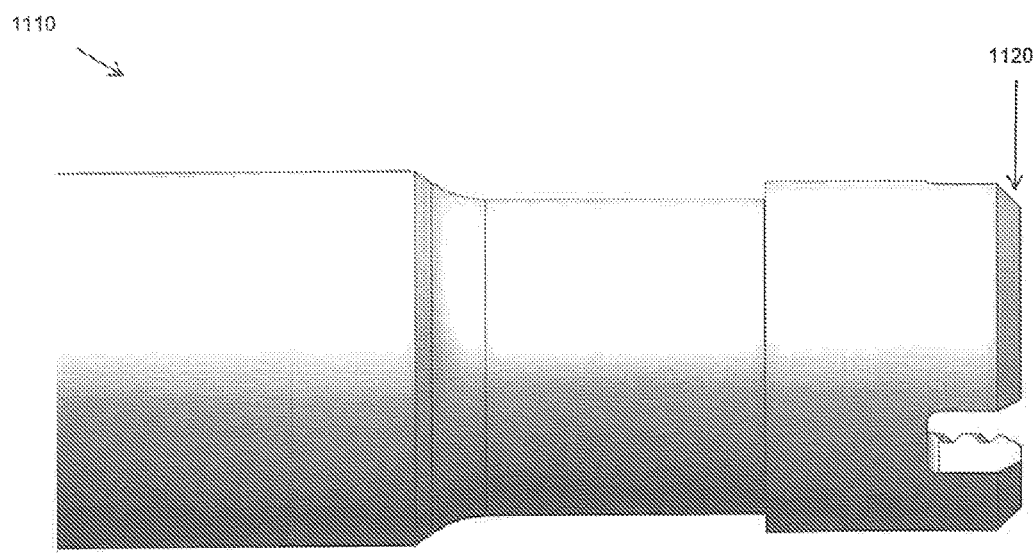
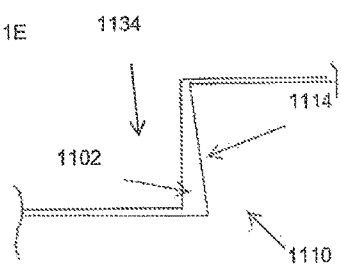
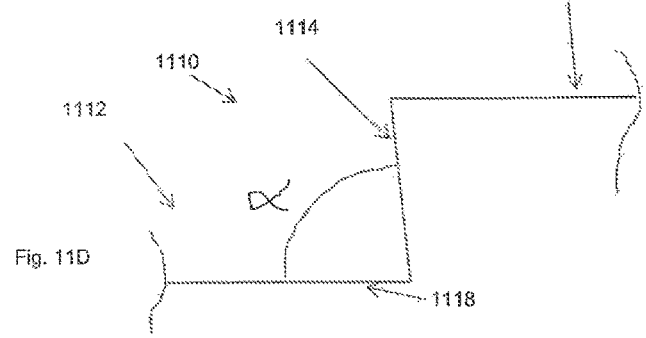
Fig. 11C
Fig. 11E
Fig. 11D

ROD COUPLING ASSEMBLIES FOR BONE STABILIZATION CONSTRUCTS

CROSS REFERENCE TO RELATED APPLICATIONS

This application claims the benefit of priority to U.S. Provisional Application No. 62/938,546, filed Nov. 21, 2019, the entire disclosure of which is incorporated by reference herein for all purposes.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Bone implants may be used to assist in the fixation of bones in spine surgeries such as, but not limited to, spinal fusions. Proximal regions of the bone implants may be configured to be coupled to a tulip. The tulip is generally rotatable relative to the implant in a first moveable state, the tulip being further configured to accept a rod for fixation.

Implants, tulips, and assemblies are generally needed to securely couple the implant, tulip and the rod.

SUMMARY OF THE DISCLOSURE

One aspect of the disclosure is a rod coupling system. The rod coupling system may include a bone implant and a tulip assembly.

In this aspect, the bone implant may have a proximal region spaced from a distal region, the proximal region sized and configured to interface with a tulip assembly. The tulip assembly may include a tulip and a collet sized and configured to be disposed at least partially within the tulip. The bone implant proximal region may include a radially recessed collet receiving region configured and sized to receive therein a radially inward protruding implant interface region of the collet, the recessed collet receiving region including a radially extending surface that is disposed at an angle less than ninety degrees relative to a bone implant longitudinal axis, the angle measured distally relative to the radially extending surface. The tulip assembly may have an opening therethrough sized and configured to receive a stabilizing rod therethrough. The implant interface region of the collet may include a radially extending surface disposed at an angle relative to a collet longitudinal axis, the radially extending surface of the implant interface region positioned to be facing the radially extending surface of the recessed collet receiving region when the implant interface region is interfaced with the recessed collet receiving region.

In this aspect, the radially extending surface of the implant interface region of the collet may be orthogonal to the longitudinal axis of the collet.

In this aspect, the radially extending surface of the recessed collet receiving region may be disposed at an angle less than 85 degrees relative to the longitudinal axis of the implant.

In this aspect, the radially extending surface of the recessed collet receiving region may be disposed at an angle greater than 45 degrees relative to the longitudinal axis of the implant.

In this aspect, the radially extending surface of the recessed collet receiving region may be disposed at an angle greater than 75 degrees relative to the longitudinal axis of the implant.

In this aspect, the radially extending surface of the recessed collet receiving region may be disposed at an angle from seventy degrees to eighty-nine degrees relative to the longitudinal axis of the implant.

In this aspect, the tulip assembly may optionally be modular such that it may be adapted to be delivered separately from the bone implant and movably secured to the bone implant after the bone implant has been at least partially implanted within bone. The implant proximal end may include an internal thread sized and configured to receive therein a threaded guide rod, the tulip assembly adapted to be advanced over the threaded guide rod and advanced over the proximal end of the implant to couple the tulip assembly and the bone implant.

In this aspect, the bone implant proximal region may include a chamfered proximal end to facilitate expansion of a collet distal end as the collet is advanced over the chamfered proximal end, the recessed collet receiving region causing the radially inward protruding implant interface region of the collet to move radially inward into the recessed collet receiving region as the collet is advanced distally over the bone implant proximal region. Coupling the collet and implant may occur before the implant is implanted into bone In this aspect, the bone implant proximal region may be configured to facilitate opening of the collet distal end as the collet is advanced over the proximal end, the recessed collet receiving region causing the radially inward protruding implant interface region of the collet to revert towards an at-rest state into the recessed collet receiving region as the collet is advanced further over the bone implant.

In this aspect, the recessed collet receiving region may have a depth from 0.1 mm to 2.0 mm.

In this aspect, the bone implant proximal region may be void of an external thread.

In this aspect, the bone implant proximal region may have an outermost sleeve surface that is sized and configured to extend over at least a portion of a distal end of the tulip. An outermost sleeve surface may be a surface of an outer implant sleeve, the outer implant sleeve disposed about an implant inner shank.

In this aspect, the recessed collet receiving region may have an annular configuration about the bone implant.

One aspect of this disclosure is a bone implant with a recessed collet receiving region, the recessed collet receiving region including a radially extending surface that is disposed at an angle less than ninety degrees relative to a bone implant longitudinal axis, the angle measured distally relative to the radially extending surface, the radially extending surface angled so as to reduce the likelihood of the collet expanding and becoming loose in response to an axial force compared to a system alike in all ways but instead having a radially extending surface that is orthogonal to the bone implant longitudinal axis.

This aspect may include any other suitable features of bone implants, systems or assemblies herein.

One aspect of this disclosure is a tulip assembly for securing to a bone implant and to a stabilizing rod. The tulip assembly may be modular or not modular.

In this aspect, the tulip may include one or more side openings that are sized and configured to receive an elongate stabilizing rod therethrough.

This aspect may include a collet with a partially spherical configuration, the collet sized to be disposed at least partially within the tulip, the tulip having an inner surface and the collet having an outer surface that are together sized and configured to interface with each other when the collet is disposed within the tulip, the tulip inner surface and the collet outer surface both configured relative to each other to cause the tulip to be movable relative to the collet in a movable arrangement.

In this aspect, the collet may include a radially inward protruding implant interface region, the protruding implant interface region including a radially extending surface disposed at an angle relative to a collet longitudinal axis and an axially extending surface that meets the radially extending surface, the radially inward protrusion facilitating a collet distal end to collapse towards a recessed region in a bone implant proximal region as the collet is advanced over the proximal region of the bone implant.

In this aspect, the tulip assembly may include a saddle sized and configured to be disposed within the tulip and at least partially proximal to the collet, the saddle having a distal region with an inner curved surface shaped to mate with a curved proximal region of the collect, the saddle having a proximal end with a rod recessed region with a configuration shaped to interface with the elongate rod.

In this aspect, a collet radially inward protrusion may have a height of 0.1 mm to 2.0 mm.

In this aspect, the radially extending surface may be orthogonal to a collet longitudinal axis.

In this aspect, the axially extending surface may be parallel to a collet longitudinal axis.

In this aspect, the axially extending surface may be tapered and may be disposed at an angle between zero and twenty degrees relative to a collet longitudinal axis.

One aspect of the disclosure is a bone implant adapted to be coupled to a tulip assembly. The bone implant has an elongate body with a long axis and a proximal region, wherein the proximal region sized and configured to be coupled within a collet of a tulip assembly. In this aspect, the proximal region may include a radially recessed collet receiving region including a radially extending surface that is disposed at an angle less than ninety degrees relative to the long axis, a distal axially extending surface and a proximal axially extending surface, the distal and proximal axially extending surfaces on either side of the radially extending surface, the proximally axially extending surface disposed further radially outward from the long axis than the distal axially extending surface.

In this aspect, a proximal end of the proximal region may have a chamfered configuration.

In this aspect, the distal axially extending surface may be parallel with the long axis.

In this aspect, the distal axially extending surface may be at an angle from zero to twenty-five degrees relative to the long axis.

In this aspect, the proximally axially extending surface may be parallel with the long axis.

In this aspect, the elongate body proximal region may be void of an outer thread.

In this aspect, the radially recessed collet receiving region may have an annular configuration about the proximal region of the elongate body.

In this aspect, the radially recessed collet receiving region may have a depth from 0.1 mm to 2.0 mm relative to an outer dimension of the implant axially adjacent to the recessed collet receiving region.

One aspect of this disclosure is a bone implant that is adapted to be coupled to a tulip assembly. The bone implant may have a long axis and a proximal region, wherein the proximal region is sized and configured to be coupled to a collet of a tulip assembly. The proximal region may include a radially recessed collet receiving area having a proximal end with an undercut ledge.

This aspect may include any other suitable feature of any implant, system or assembly herein.

BRIEF DESCRIPTION OF THE DRAWINGS

FIGS. 1B, 1C, 1D and 1E are sectional views showing an exemplary rod stabilizing sequence of steps.

FIG. 2B illustrates an exemplary rod coupling system with the implant uncoupled from a tulip assembly.

FIG. 2C illustrates a sectional view of an exemplary rod coupling system with the implant uncoupled from a tulip assembly.

FIG. 2D illustrates a sectional view of a portion of an exemplary tulip assembly.

FIG. 2E illustrates an exemplary rod coupling system with the implant coupled with a tulip assembly.

FIG. 2F illustrates a sectional view of an exemplary rod coupling system with the implant coupled to a tulip assembly.

FIG. 2G illustrates a sectional view of a portion of an exemplary tulip assembly interfacing a proximal region of a bone implant.

FIG. 2H illustrates an exemplary rod coupling system with the implant coupled and fixedly secured with a tulip assembly.

FIG. 2I illustrates a sectional view of an exemplary rod coupling system with the implant coupled and fixedly secured to a tulip assembly.

FIG. 2J illustrates a sectional view of a portion of an exemplary tulip assembly interfacing and fixedly secured with a proximal region of a bone implant.

FIG. 5A illustrates an exemplary rod coupling system with the implant uncoupled from a tulip assembly.

FIGS. 5B, 5C and 5D illustrates an exemplary rod coupling system with the implant coupled to a tulip assembly, with a split annular member part of the tulip assembly.

FIGS. 8A, 8B, 8C, 8D, 8E, 8F and 8G illustrate an exemplary embodiment in which a proximal portion of the implant is sized and configured relative to a tulip to interface with a surface of the tulip of the tulip assembly.

FIGS. 9A, 9B, 9C, 9D, 9E and 9F illustrate an example of a tulip assembly that includes an inner tulip member and an outer tulip member.

FIGS. 10A, 10B, 10C, 10D, 10E, 10F, 10G, 10H and 10I illustrate an example of a tulip assembly that includes an inner tulip member and an outer tulip member.

FIGS. 11A, 11B, 11C, 11D, 11E, 11F, 11G, 11H, 11I and 11J are an example of a rod coupling assembly in which an implant proximal end includes a collet receiving region with a proximal end having an undercut ledge configuration.

DETAILED DESCRIPTION

The disclosure herein is related to rod coupling systems or assemblies. The rod coupling assemblies herein include a tulip, and wherein the assemblies are adapted and configured to be coupled to a stabilizing rod that is part of a bone stabilization construct. The rod coupling assemblies in this context may also be considered to include an implant, or have an implantable portion, that is secured in tissue (e.g. bone), wherein the implant is coupled to the tulip. The rod may be part of a larger construct that may be used to stabilize one or more regions of a patient's body, such as a spine or pelvis. In some embodiments, the rod coupling assemblies herein may be disposed in a lower region of the spine, such in the region of a sacro-iliac joint.

The disclosure herein that is related to the rod coupling assemblies is related to some aspects of the disclosure in published application WO2020/168269, which is fully incorporated by reference herein for all purposes. For example, and without limitation, FIGS. 25A-26B in publication WO2020/168269 show an exemplary rod coupling assembly that includes a head portion 2506 that may be provided with a coupler 2524 and a main body 2526 and a nut (not shown). The nut may have external threads that mate with internal threads located in the proximal recess of main body 2526 to tighten a spinal rod (not shown) against the bottom of channels 2528 in main body 2526. As shown in FIG. 25B, the proximal end of shank portion 2502 may be provided with a circumferential rib or barb 2530 for securing head portion 2506 to shank portion 2502 in a snap-fit manner. The head portion may be considered part of a rod coupling assembly. The head portion may be considered part of the implant, even though it is not directly engaging tissue.

Figure 1A:
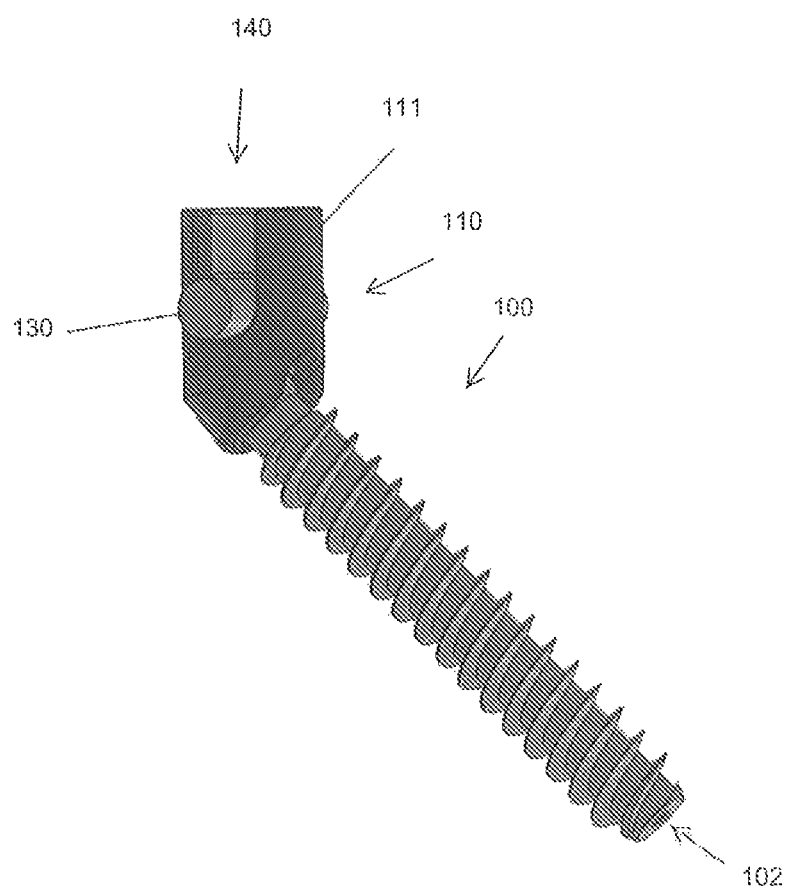
FIG. 1A illustrates an exemplary rod coupling system in an exemplary stabilized state.
Figure 1C:
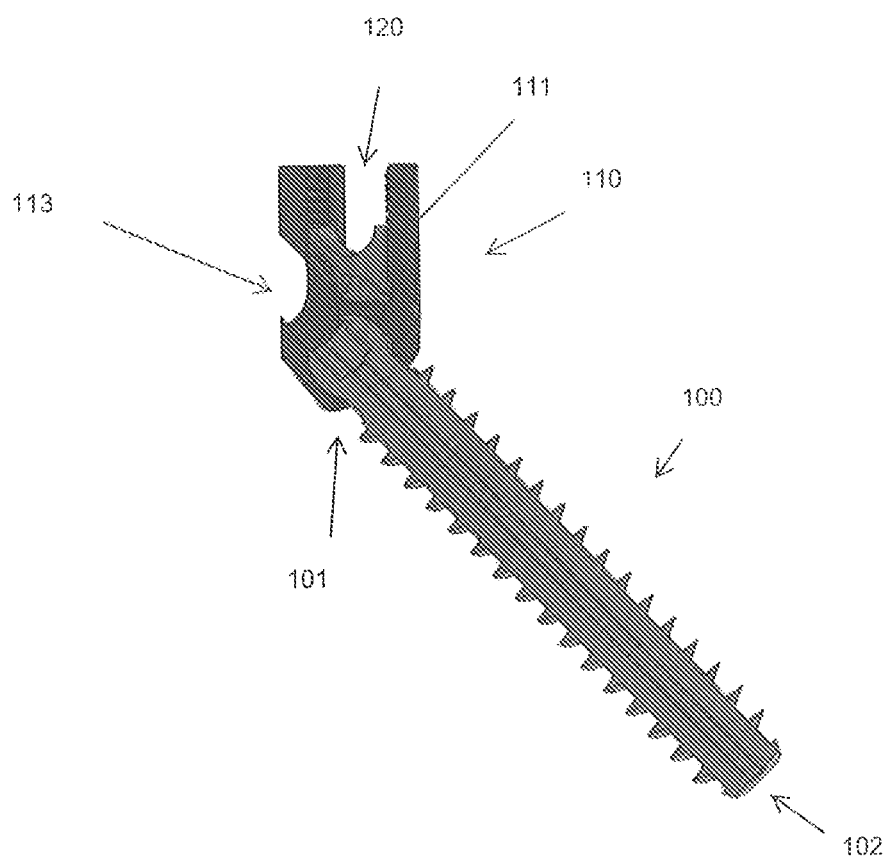

FIGS. 1A-1E herein illustrate an exemplary rod coupling assembly 110, which is shaped and sized to be secured to implant portion 100 as well as rod 130 (only a portion of which is shown). Assembly 110 includes main body 111, which may also be referred to herein as a tulip. Implant 100 has a rounded (optionally at least partially spherical) proximal end 101 that is shaped and sized to stably but movably interface with a curved inner surface 112 of main body 111 (shown in FIG. 1B) and a curved inner surface of implant stabilizing member 120 (e.g., a saddle), as shown in FIG. 1D. In the position in FIG. 1D (as well as the fully assembled views in FIGS. 1A and 1E), the main body 111 is rotatable to some degree relative to the proximal end 101 of implant 100 due to the spherical surfaces of the three components (implant 100, main body 111, and implant stabilizing member 120). The position of the curved surfaces is such that the implant axis "IA" (FIG. 1D) is not collinear with the main body axis "MB." Preferably, the angle (as shown) is at least 15 degrees, and in some embodiments is between 35 and 55 degrees, optionally around 45 degree (e.g. between 42 and 48 degrees). The orientation of the spherical surfaces can thus impart and allow a favored or preferred angle between the main body (e.g., tulip) and the implant, while allowing for some rotational freedom between the two.

In the position shown in FIGS. 1A and 1C-1E, channel 113 in tulip 111 is in communication with and aligned with the internal channel in the implant, which includes distal port 102. This allows, if desired, an agent to be delivered through the tulip and through the implant and into the subject. The channel or port 113 in the tulip also allows access to the rotational drive mechanism such as a hex or torx drive.

Once implant stabilizing member 120 (e.g., saddle) is advanced to the position shown in FIG. 1D, rod 130 may be positioned relative to the rod channel in the tulip such that the rod is extending through the rod channel. FIGS. 1A and 1E illustrate a portion of a rod that is positioned in the tulip. Rods and tulips are at a high level known in the art. To secure the rod in place, rod stabilizing member 140 (e.g., a threaded set cap) may be advanced via threaded rotation into the main body until it engages the rod 130 and help secures it in place, as shown in FIGS. 1A and 1E. Implant stabilizing member 120 also has a proximal curved surface (as shown in FIG. 1B) configured to stably interface with a portion of the rod, as shown in the sectional view of FIG. 1E. In an exemplary use, rod 130 may be extending in a direction that is generally considered superior-to-inferior, and may be part of a spine stabilization system that includes additional bone anchors ("implant"). Once the rod is secured, the entire assembly, including the implant, is essentially a secure and stable construct.

Figure 2A:
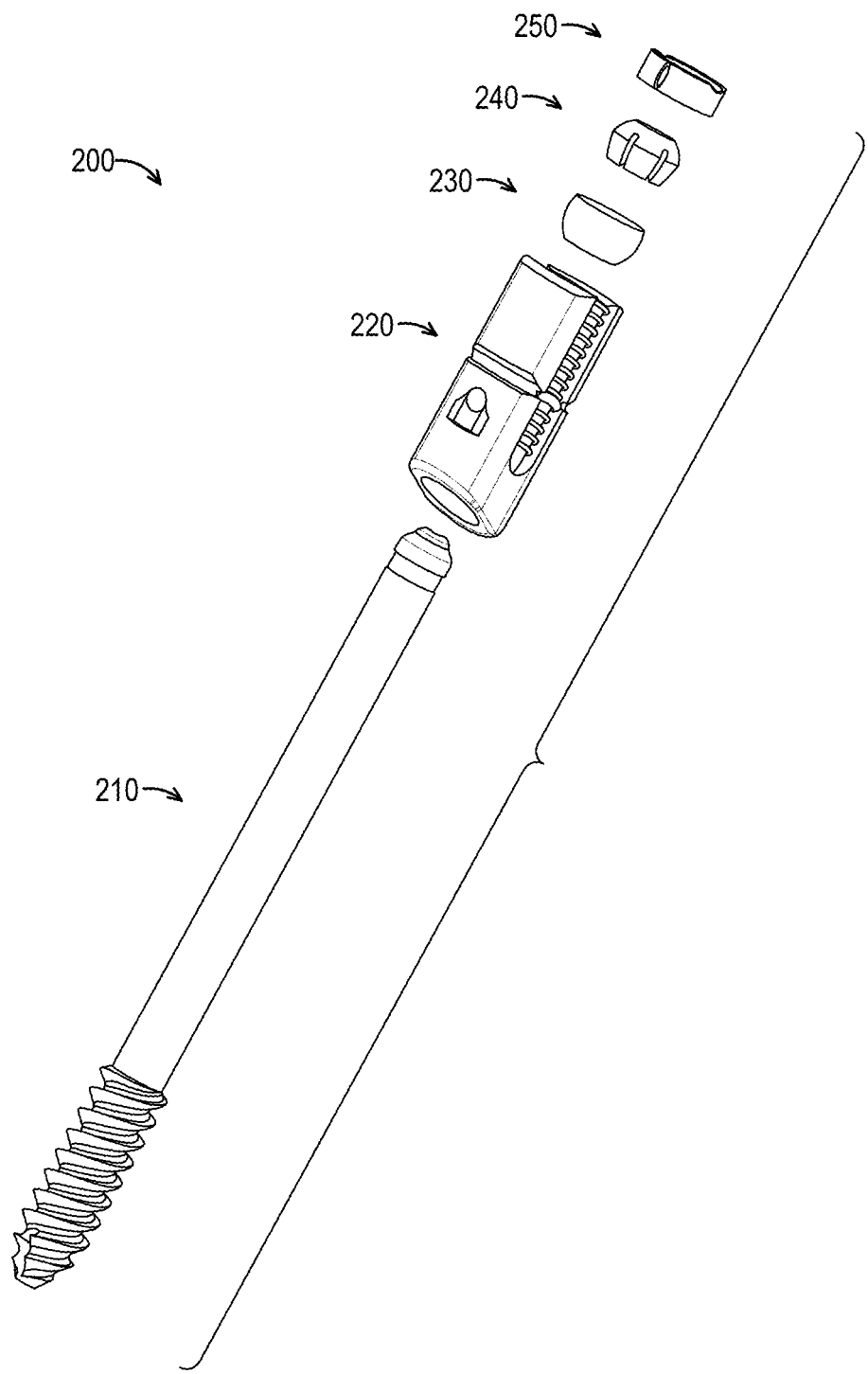
FIG. 2A illustrates an exploded view of an exemplary rod coupling system.

FIGS. 2A-2J illustrate a portion of an exemplary rod coupling assembly 200, but excludes illustrating the rod and set cap (e.g., a set cap 140 from FIGS. 1A-1E) for clarity. FIGS. 2A-2J illustrate the portion of the rod coupling assembly that illustrates how the main body or tulip 220 is secured relative to the implant portion 210. In any of the embodiments here, a rod can be secured relative to the tulip 220 using any of the disclosure herein, such as rod stabilizing member 140 shown in the embodiment in FIG. 1A. FIG. 2A shows an exploded view of rod coupling assembly 200, which may be considered to include a proximal region of implant portion 210. The rod coupling assembly 200 includes main body or tulip 220, distal collet portion 230, proximal collet portion 240, and saddle 250. Implant 210 may be at least partially threaded, as shown, and can be sized and shaped to anchor into bone.

The tulip 220 is configured to receive in a channel therein both spherical collet portions and the saddle, as shown in FIG. 2D. Proximal collet portion 240 includes slits formed therein, as shown. In FIGS. 2B, 2C and 2D, the split collet is disengaged from the mating tapered inner surface 231. The proximal portion of implant portion 210 may then be advanced within the collets, with the implant proximal end causing the collet fingers to deflect outward, or split. Continued advancement of the implant portion causes the collet fingers to deflect back inward about the implant groove 211, as is shown in FIGS. 2E-2G.

Saddle 250 may include one or more slots (shown in FIG. 2A) that are sized and configured to interface with swaged bosses to limit the amount of travel relative to the tulip.

The rod, not shown for clarity, may then be advanced through tulip 220, and a threaded set cap, not shown for clarity, can be advanced distally, causing the rod to be pushed against saddle 250, which compresses the collet, as shown in FIGS. 2H-2J. The implant proximal portion is now secured relative to the rod coupling assembly, and the rod is stably coupled to the rod coupling assembly.

In the embodiments in FIGS. 2-7 and 11 herein, once the desired angle is obtained between the tulip and the implant, the set screw is advanced, causing the set screw and the rod to advance the saddle against the collet. The slotted collet is then compressed against the tulip, which compresses and secures the collet against the proximal portion of the implant. This is the general method by which the assemblies are secured to the implant as well as the rod.

Figure 3B:
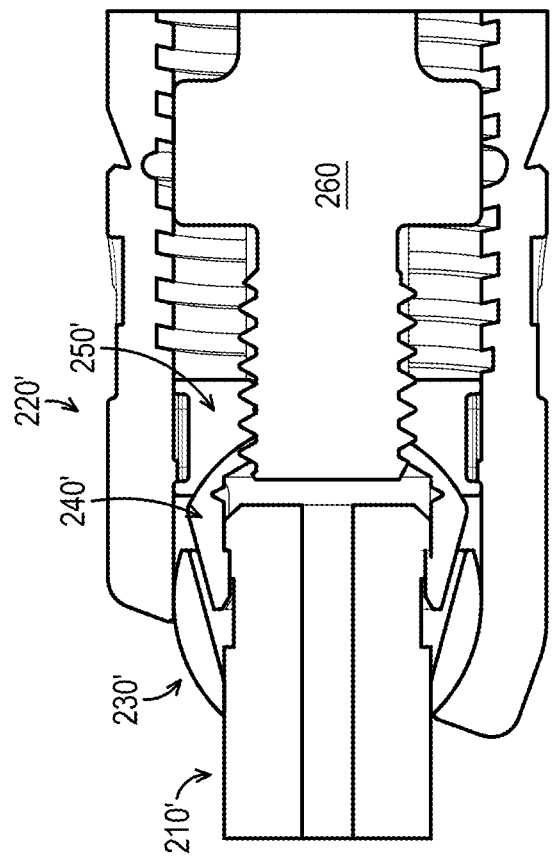
FIGS. 3A and 3B illustrate a rod coupling assembly interfaced with a threaded tool that may be used for removal.
Figure 3A:
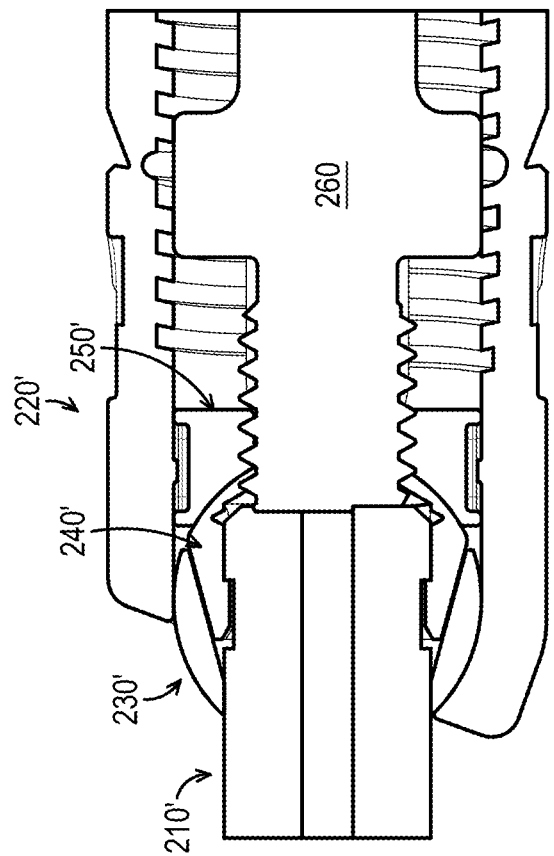

FIGS. 3A and 3B illustrate a variation on the embodiment in FIGS. 2A-2H (similar parts being similarly labeled), wherein the rod coupling assembly includes a saddle and proximal collet that are threaded to interface with threaded tool 260. Once the threaded tool 260 is threaded into the saddle and collet, as shown in FIG. 3A, the tool is then pulled proximally with respect to the tulip 220', pulling the saddle and collet proximally and disengaging from the distal spherical collet. This allows the saddle to be retracted proximally, which provides the option to remove the tulip if needed (e.g., if the implant portion were to become loose). The tulip can also have a side channel (as in FIGS. 1A-1E) that can provide access to the proximal end of the implant if needed, such as if the tulip is rotated and the physician cannot get access to the tulip main channel. The distal collet portion 230 (or 230') allows for favored angle rotation of the tulip 220 relative to the implant portion 210.

FIGS. 4A-4H is an exemplary embodiment of a rod coupling assembly 400 that includes main body or tulip 420, spherical collet 430 (shown with slits in FIG. 4A), saddle 450, set cap 460, and split annular member 440. Implant portion 410 is also shown, a proximal region of which includes groove 411 or other similar type of depression or recessed region formed therein. The implant 410 may come assembled with split annular member 440 (e.g. split ring), such as in the configuration in FIGS. 4A and 4B. Main body or tulip 420 houses spherical member 430 and saddle 450. A rod that can pass through the tulip is not shown for clarity, but threaded set cap 460 can be advanced within the main body and advanced until it secures the rod in place, details of which are described elsewhere herein.

Figure 4A:
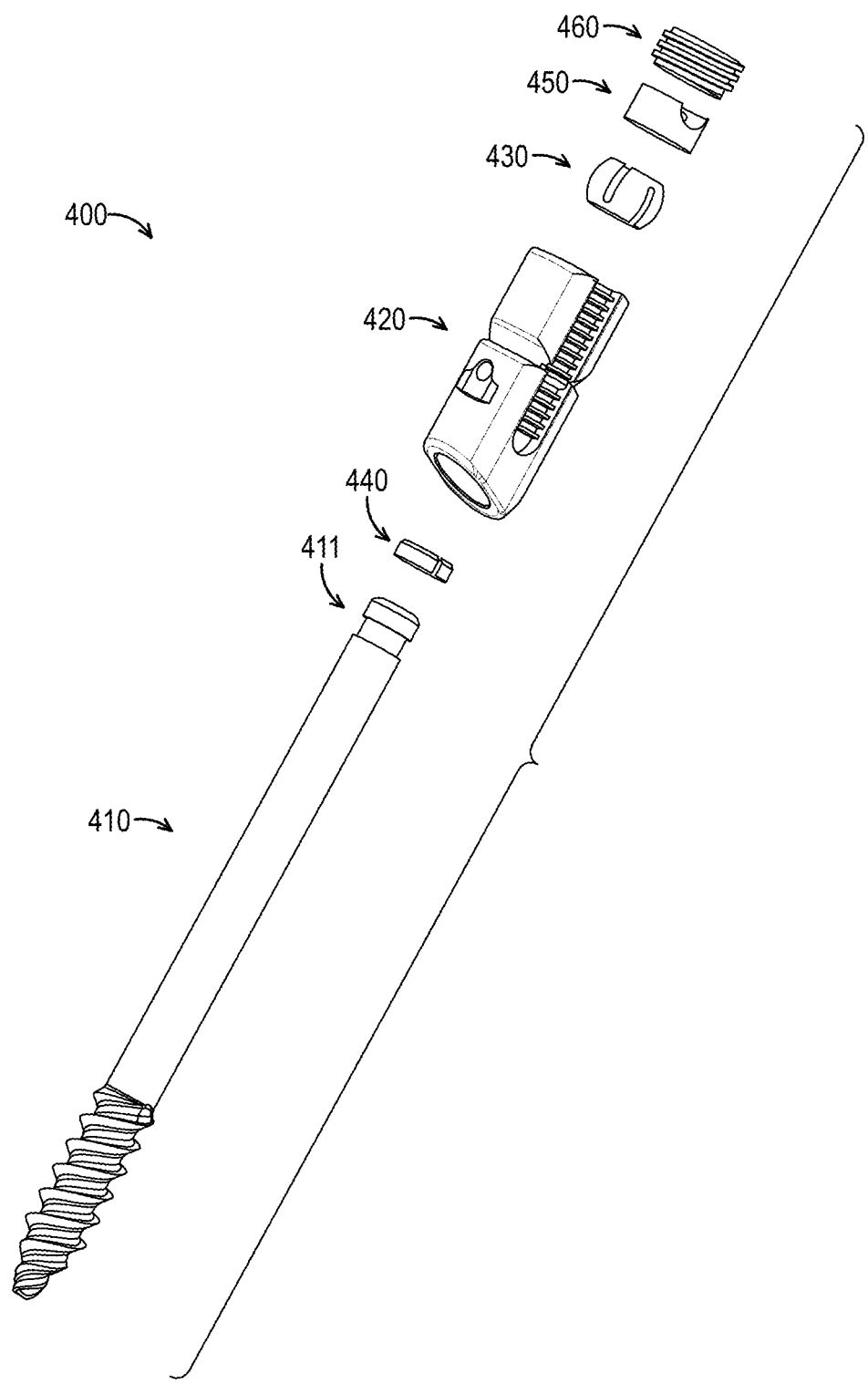
FIG. 4A illustrates an exploded view of an exemplary rod coupling system.
Figure 4B:
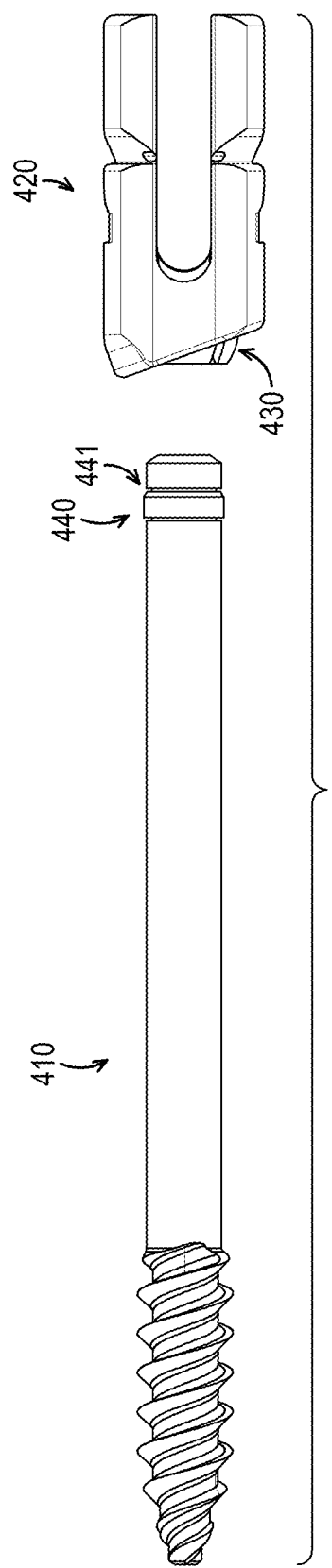
FIG. 4B illustrates an exemplary rod coupling system with the implant uncoupled from a tulip assembly.
Figure 4C:
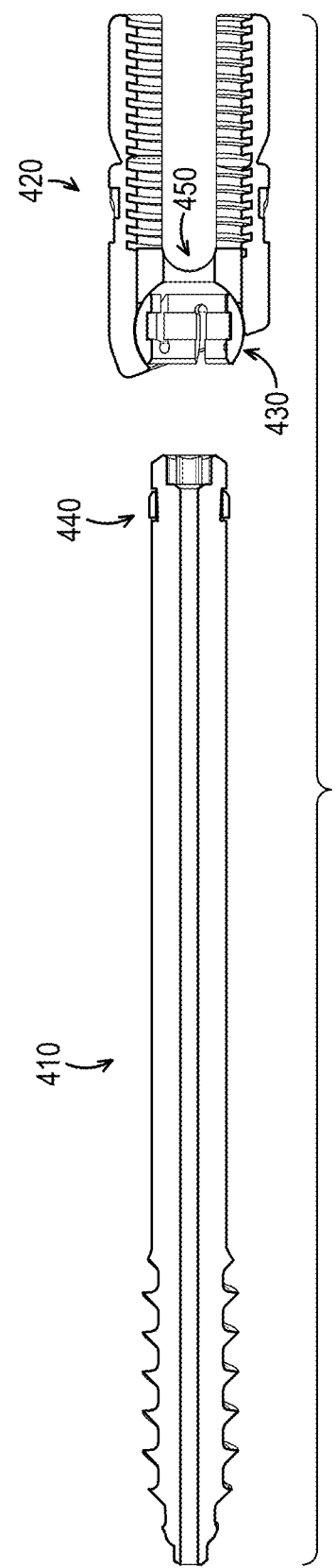
FIG. 4C illustrates a sectional view of an exemplary rod coupling system with the implant uncoupled from a tulip assembly.
Figure 4D:
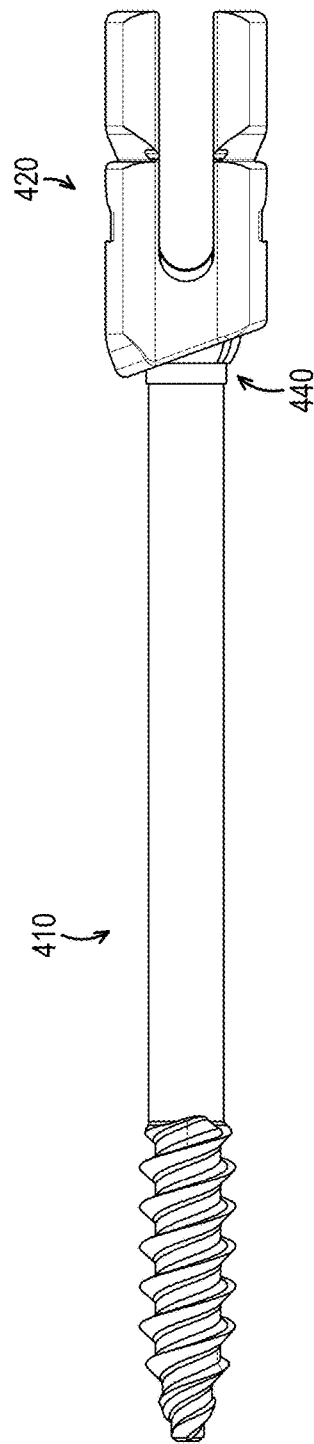
FIG. 4D illustrates an exemplary rod coupling system with the implant coupled with a tulip assembly.
Figure 4F:
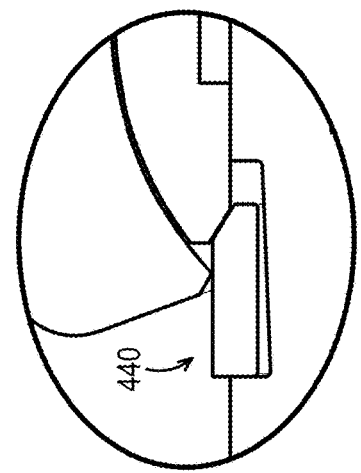
FIGS. 4E, 4F, 4G and 4H illustrate a rod coupling system with split annular member configured to interface with a bone implant.
Figure 4E:
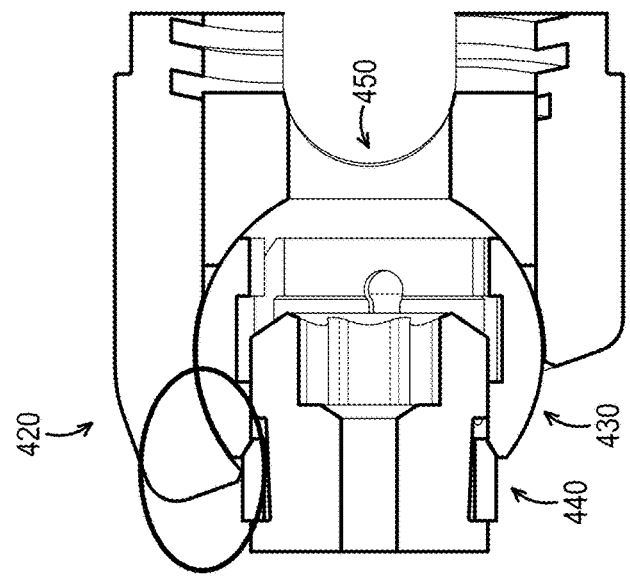
Figure 4H:
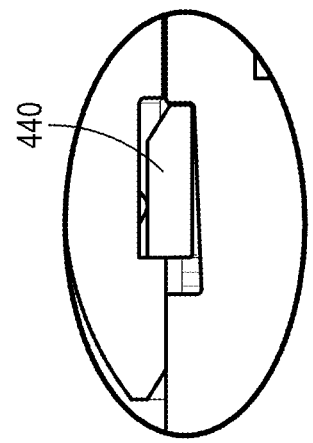
Figure 4G:
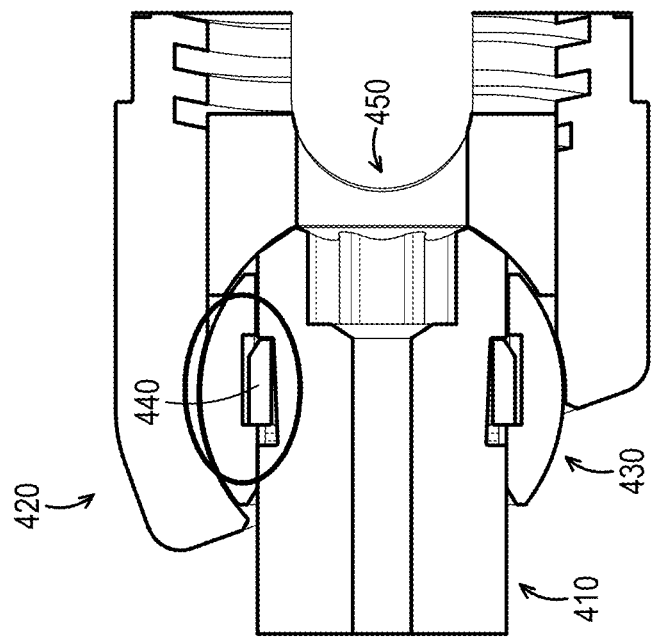

Split annular member 440 has a tapered proximal surface 441, shown in FIGS. 4B and 4C. When the implant portion 410 and annular member 440 are advanced into the tulip 420 and spherical collet 430, as shown in FIGS. 4D, 4E and 4F, split annular member 440 is pushed distally into the deepest part of the tapered implant groove 411. When set-cap 460 is torqued, split annular member 440 is pushed into the shallow portion of the tapered implant groove 411 and into the groove within the spherical collet 430, as shown in FIGS. 4G and 4H.

FIGS. 5A-5D illustrate an exemplary rod coupling assembly that is similar to the embodiment in FIGS. 4A-4H, and similar or the same parts are similarly labeled. All disclosure from the description of FIGS. 4A-4H can be expressly incorporated into the embodiment of FIGS. 5A-5D unless indicated to the contrary. In FIGS. 5A-5D, split annular member 540 is relatively larger than in FIGS. 4A-4H, and can be pre-assembled within a groove in spherical member 530, as shown in FIGS. 5B-5D. The movement of the annular member in this embodiment is opposite that in FIGS. 4A-4H. As the proximal region of implant 510 is advanced into the spherical member 530, annular member 540 is pushed proximally into the deepest part of spherical member groove, as shown in FIG. 5C. As the proximal region of implant 510 is further advanced, annular member 540 snaps into implant groove 511. As the set cap is torqued, split annular member 540 is pushed into the shallow portion of the spherical member groove, as shown in FIG. 5D.

Figure 6A:
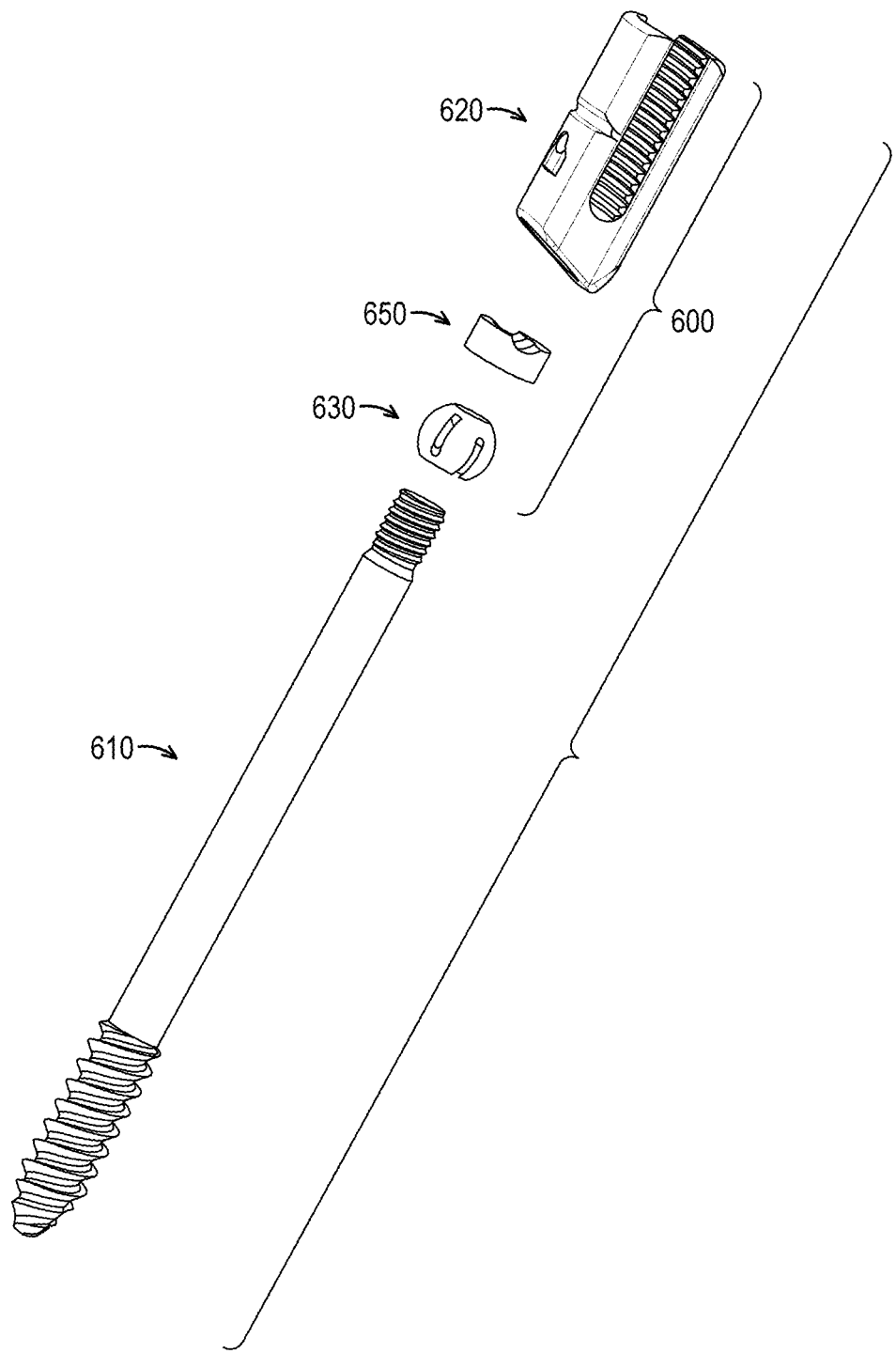
FIG. 6A illustrates an exploded view of an exemplary rod coupling system.
Figure 6B:
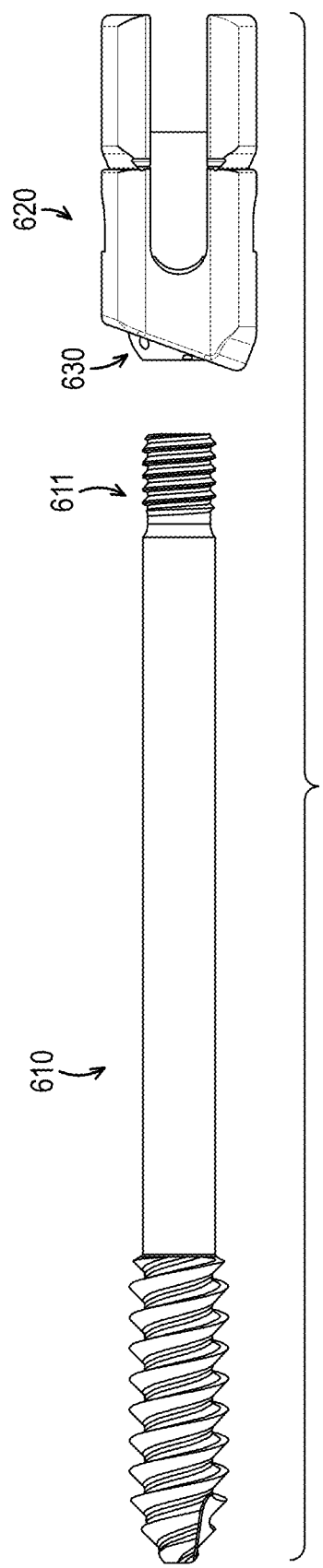
FIG. 6B illustrates an exemplary rod coupling system with the implant uncoupled from a tulip assembly.
Figure 6C:
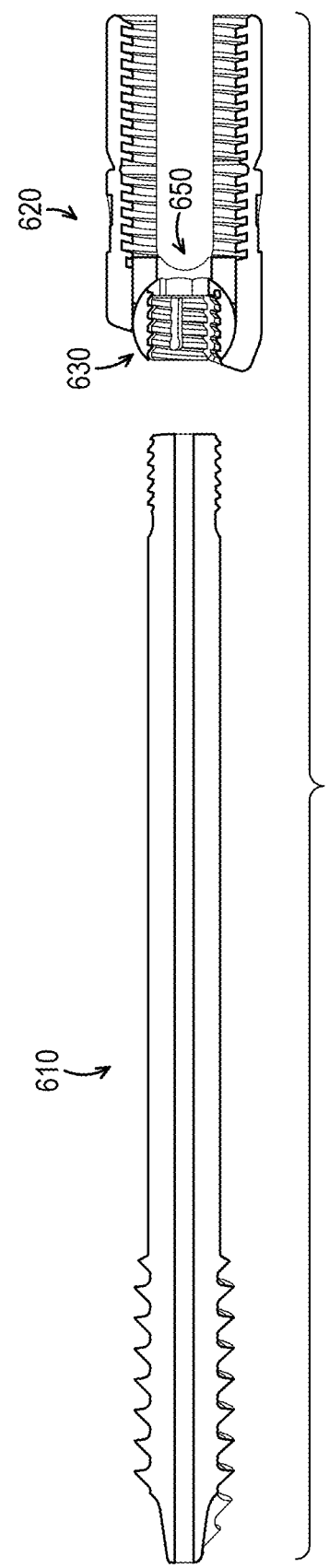
FIG. 6C illustrates a sectional view of an exemplary rod coupling system with the implant uncoupled from a tulip assembly.
Figure 6D:
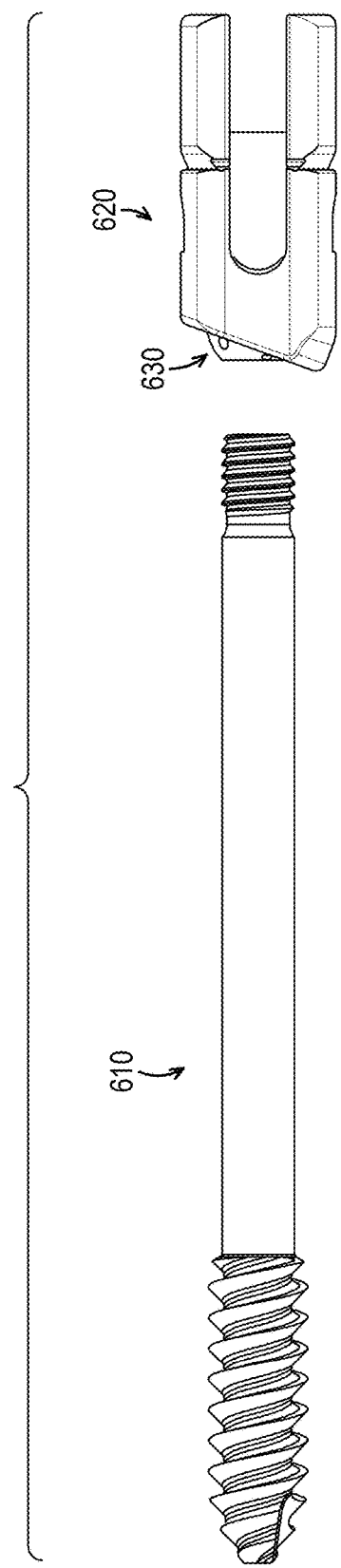
FIG. 6D illustrates an exploded view of an exemplary rod coupling system.
Figure 6E:
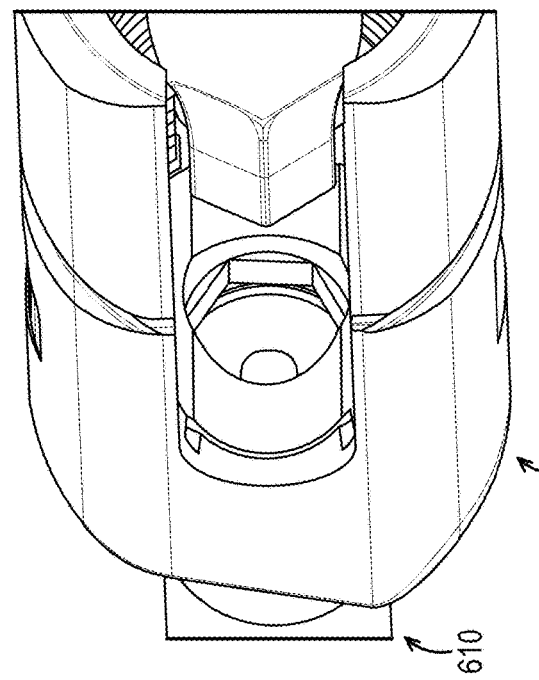
FIG. 6E is a perspective view of an exemplary rod coupling system with the implant coupled to a tulip assembly.

FIG. 6A-6E illustrate an embodiment of a rod coupling assembly 600 that includes main body or tulip 620, saddle 650, spherical collet 630, and a set cap (not shown). Threads 611 on the proximal region of implant 610 (FIG. 1B) interface with internal threads in spherical collet, which are shown in FIG. 6C. The main body or tulip 620 and collet 630 assembly is threaded onto the implant, and the tulip 620 driver engages hex or torx in the spherical collet, as shown in FIG. 6E. The thread can be a saw tooth thread. The spherical collet has slits formed therein so that as the spherical collet is rotated it is slightly compressed radially. A rod can then be positioned through the tulip, and a set cap can be torqued to secure the rod in place.

Figure 7A:
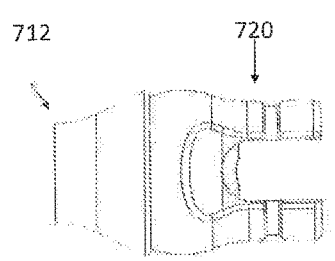
FIGS. 7A, 7B, 7C, 7D and 7E illustrate an exemplary embodiment in which a proximal portion of the implant is sized and configured relative to a tulip to interface with a surface of the tulip of the tulip assembly.
Figure 7B:
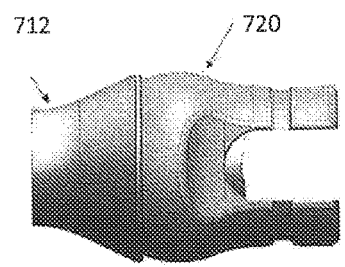
Figure 7C:
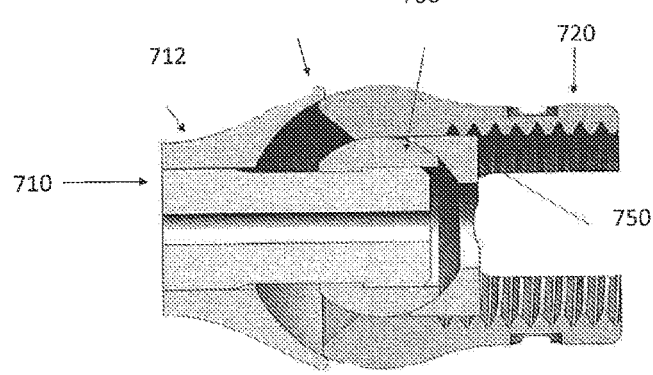
Figure 7D:
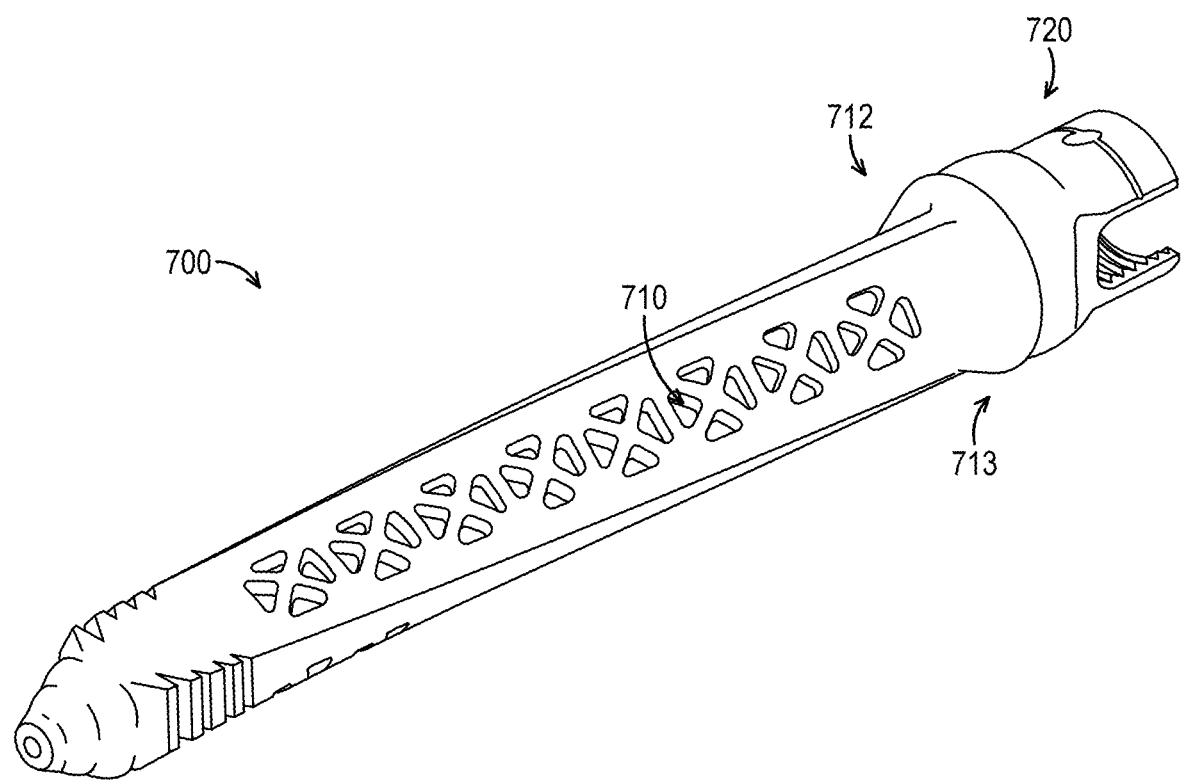
Figure 7E:
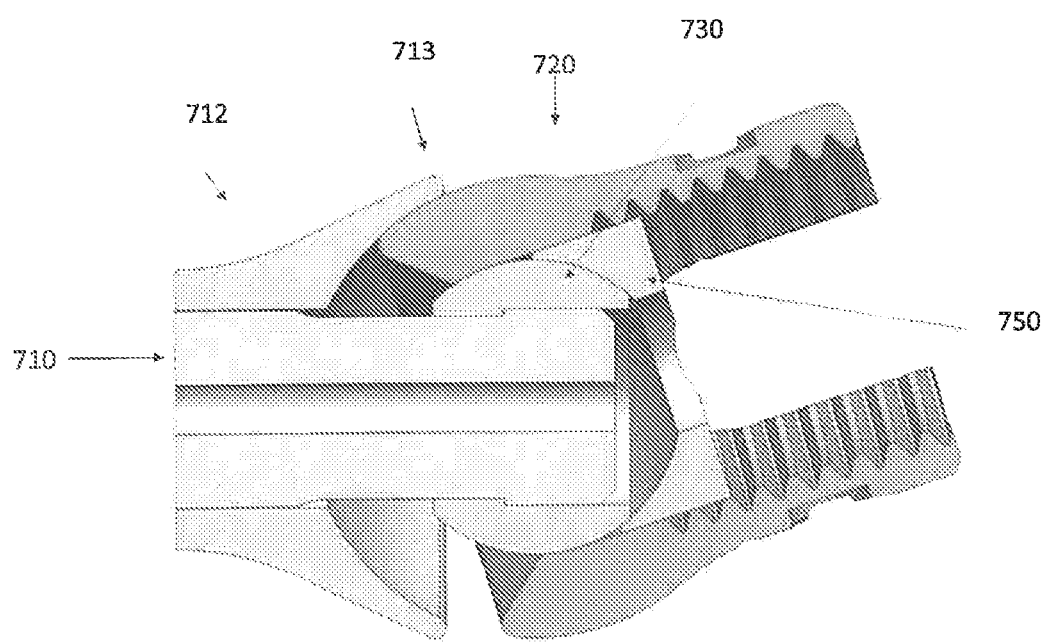

When a rod is secured to a rod coupling assembly of an anchoring implant (such as any of those described herein), bending loads may be applied to the tulip and to the implant. It may be beneficial for the rod coupling assembly and/or implant to be configured and/or sized to help resist the bending loads. FIGS. 7A-7E illustrate a merely exemplary rod coupling assembly in which a portion of the implant, or implant portion, interfaces with the main body, or tulip, and in particular, provides support for the tulip to provide more resistance to bending loads. In FIG. 7C, shank 710 of the implant 700 is an example of an elongate member of the implantable portion, such as any of the elongate inner members (e.g., shanks) in PCT published application WO2020/168269, the disclosure of which is incorporated by reference herein. Outer sleeve 712 refers generally to an outer member that is disposed at least partially about the inner member or shank 710. FIG. 7D illustrates a non-limiting example of an implant 700 that includes an outer sleeve 712 and an inner elongate body 710 (e.g., shank portion). The sleeve includes a proximal region 713 that has a configuration that extends radially outward and extends such that its proximal end is disposed radially outside of and about at least a portion of the tulip 720 and provides support to the tulip. The tulip may also act a locking mechanism for the outer sleeve.

The sleeve 710 in this exemplary embodiment may be any of the outer elongate members herein, including PCT published application WO2020/168269, such as body 2504 in FIG. 25B. Additionally, any of the outer elongate members (e.g., body 2504 in FIG. 25B in PCT published application WO2020/168269), may include a proximal region that extends radially outward, as does the sleeve 710 in FIGS. 7A-7E. The implants in this embodiment may take a wide variety of shapes and configuration and may include a proximally extending region 713 that is sized and conjured to interface with an outer surface of the tulip.

Figure 8F:
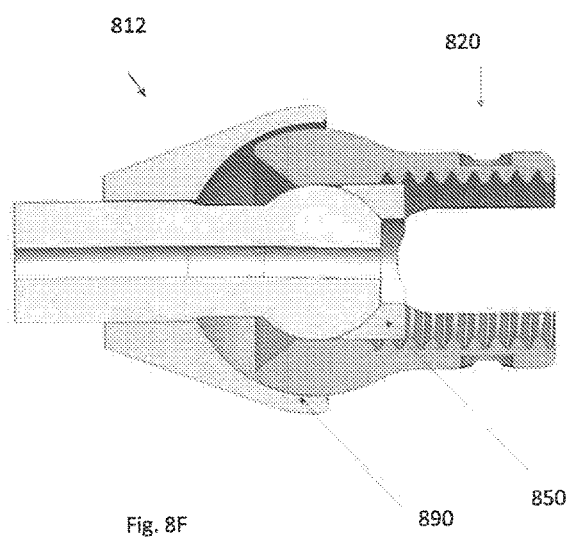
Figure 8G:
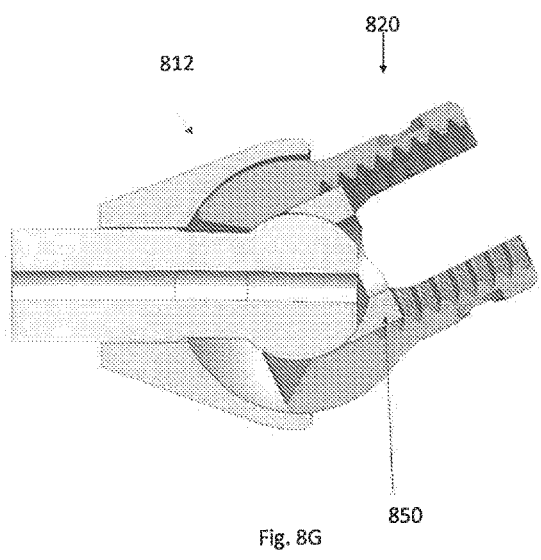

FIGS. 8A-8G illustrate an embodiment of a rod coupling assembly that is similar in some ways to the embodiment shown in FIGS. 7A-7E, and may incorporate any suitable disclosure by reference into the embodiment. In this embodiment, a sleeve portion 812 of the implant extends around tulip 820 to a greater extent than in FIGS. 7A-7E, providing more support and more resistance to bending loads. The spherical component in this embodiment is part of implant as implant spherical element 830, shown in FIG. 8C. FIGS. 8D and 8E illustrate clearance 870 between tulip 820 and implant sleeve 812 under normal or no loading. FIGS. 8F and 8G illustrates an extreme load scenario, and illustrates how outer sleeve 812 acts as a brace and prevents excessive deflection of the neck region of the inner shank 810. The rod and set screw are not shown for clarity.

Figure 9D:
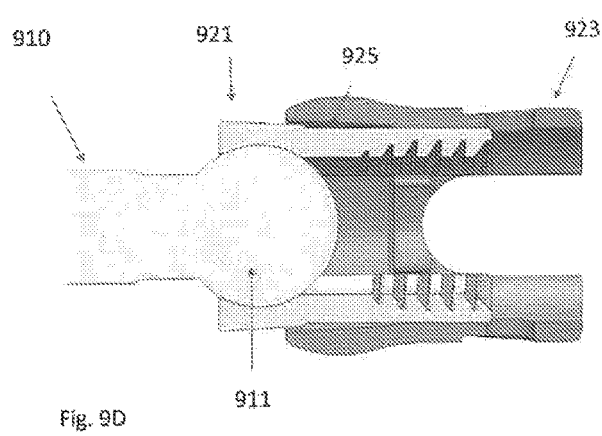
Figure 9E:
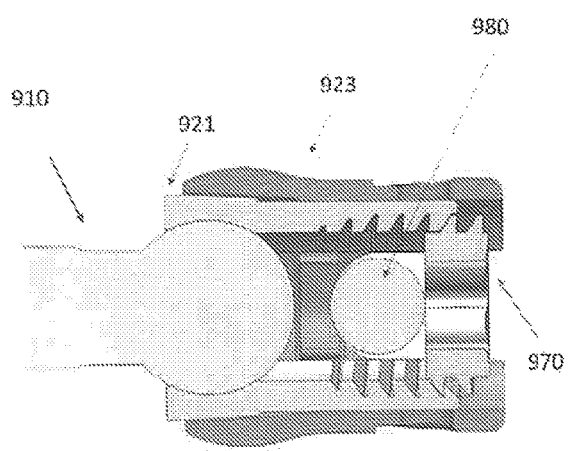
Figure 9F:
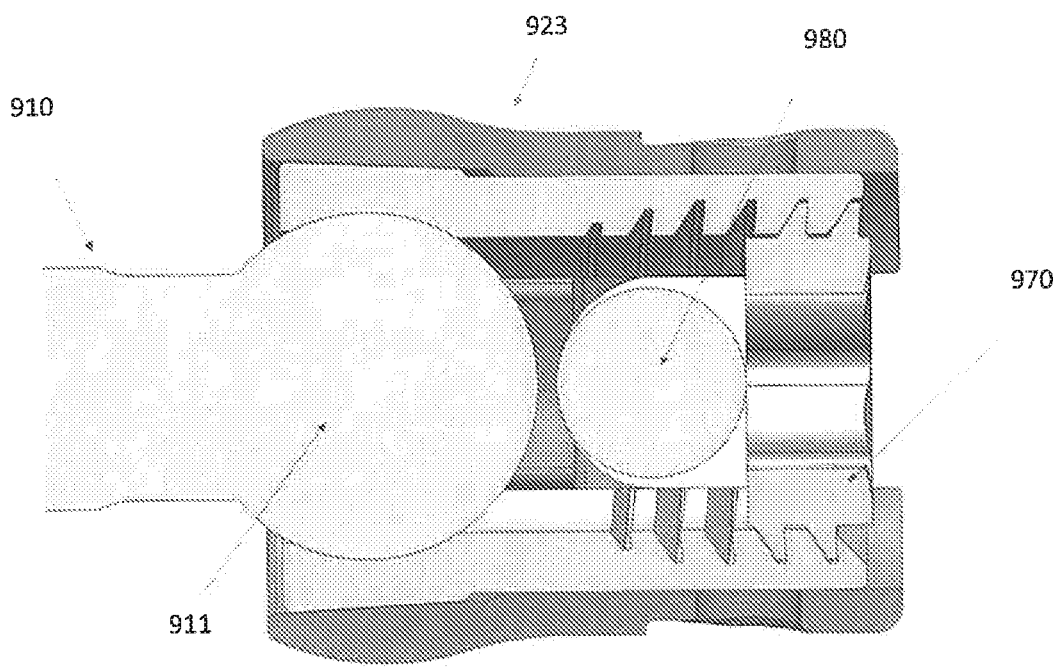
Figure 10H:
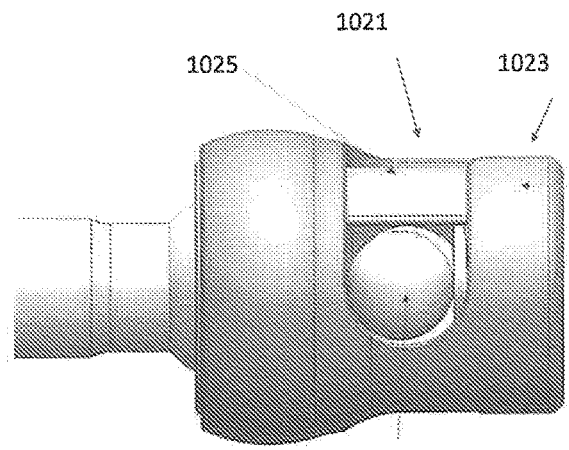
Figure 10I:
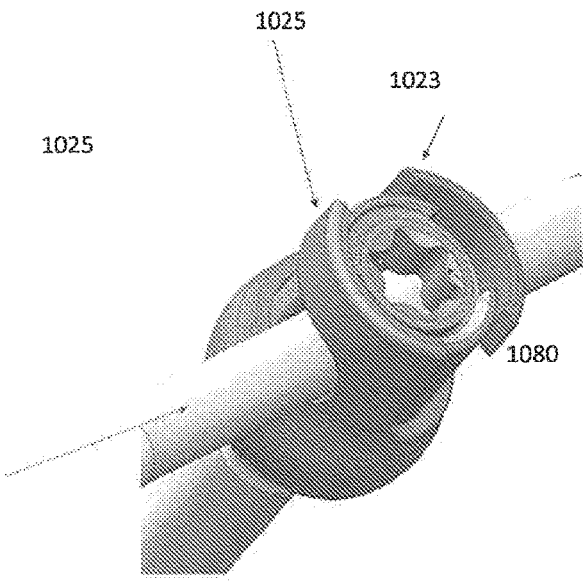

As discussed herein, some rod coupling assemblies may be under bending loads once implanted. FIGS. 9A-9F illustrate an exemplary tulip that includes an inner tulip member and an outer tulip member. Tulip 920 shown in FIGS. 9A-9F may be used with implants other than those shown or described herein. Tulip 920 includes outer tulip 923 and inner tulip 921. The tulips in FIGS. 9A-9F may be incorporated into any suitable embodiment herein unless indicated to the contrary. FIGS. 9A-9C illustrate the tulip member 921 and 923 without the rest of the rod coupling assemblies. FIG. 9D illustrates an exemplary implant portion 910 with a spherical member 911 being positioned within inner tulip 921. As shown, clearance 925 between outer tulip 923 and inner tulip 921 in the unlocked position allows the spherical member 911 to snap into the inner tulip interface, as shown. Then, in FIG. 9E, after rod 980 placement, set cap 970 tightening causes inner tulip 921 to be pulled and moved proximally relative to outer tulip 923, as shown. As shown in FIG. 9F, the taper interface between outer tulip 923 and inner tulip 921 allows the tulip assembly to lock onto the spherical member 911. In this final configuration, the outer tulip helps prevent inner tulip splaying, to which some tulips may be susceptible under bending loads. As shown in the figure, the rod coupling assembly may also include a saddle that can be advanced to the spherical member, such as any of the saddles herein. This embodiment of an example of an inner tulip member that is configured to be moved axially relative to an outer tulip member when in use.

FIGS. 10A-10I illustrate an exemplary embodiment of a rod coupling assembly that is similar to the embodiment shown in FIGS. 9A-9F with inner and outer tulip members. Any of the suitable disclosure from the embodiment in FIGS. 9A-9F may be incorporated into the disclosure of 10A-10I unless indicated to the contrary, such as the set cap threading causing the inner tulip to be drawn proximally within the outer tulip. As shown, and as is the case in the embodiment in FIGS. 9A-9F, inner tulip 1021 has a distal end with at least one slit 1025 therein, allowing it to be expanded and collapsed to some extent during axial movement. One difference in this embodiment is the configuration of the outer tulip 1023, and the manner in which it may be rotated (for example only, a quarter or ¼ turn) prior to final set cap 1080 tightening. Rotating outer tulip 1023 causes a portion 1025 of outer tulip 1023 to extend over a region of inner tulip, as shown, which can provide more radial support to the tulips arms, and can reduce the likelihood of inner tulip splaying. In other embodiments, the outer tulip and or the inner tulip could have different configurations, and could be rotated more or less than a quarter turn (90 degrees), such as between 0 and 180 degrees, such as from 5 to 135 degree, such as from 45 to 135 degrees, such as 90 degrees.

FIGS. 11A-11J illustrate an additional exemplary embodiment of rod coupling system or assembly 1100 that includes exemplary bone implant 1110 and tulip assembly 1130. It is understood that alternative systems may include bone implant 1110 and other types of tulip assemblies (including those not described herein). It is also understood that alternative systems may include tulip subassembly 1130 and other types of bone implant (including those not described herein). It is further understood that alternative systems may include one or more features of bone implant 1110 and other types and features of tulip subassemblies (including those not described herein). It is also understood that alternative systems may include one or more features of tulip subassembly 1130 and other types and features of bone implants (including those not described herein).

System 1100 and other similar systems herein that include a tulip assembly and bone implant may also be referred to herein as a rod coupling assembly or system, as the system may be used to couple or secure a stabilizing rod relative to the tulip assembly and bone implant.

System 1110, bone implant 1110 and tulip assembly 1130 may be understood to include other features set forth herein even if the textual description thereof does not expressly disclose those features.

An exemplary aspect of this embodiment is that an interface between a collet and a proximal region of the bone implant is sized and configured so as to reduce the likelihood of the distal end of the collet from expanding and possibly becoming loose in response to axial forces (e.g., proximal forces) on the tulip. For example, proximal forces on the tulip from rod movement may translate to the collet, which may tend to undesirably cause the collet distal end to loosen or expand over time.

Additionally, the collect and implant interface in the exemplary embodiment in FIGS. 11A-11J is configured to resist or minimize the likelihood of becoming loose from axial forces caused by rod reduction. Rod reduction can be generally described as when a physician may position the rod proud of the tulip and reduces it (i.e., forces the rod into the implant tulip) in order to get a correction in anatomy. This step occurs before the collet is tightened in place. These reductions exert a great amount of force on the implant, and because the collet is not yet tightened, the collet may come apart. The collet and implant interface in FIGS. 11A-11J is an example of such an interface that is sized and configured to ensure, or increase the likelihood of, the collet remaining closed during these reductions.

To reduce the likelihood of collet loosening or expansion in response to these forces and in these scenarios, the implant undercut creates or produces a gap 1102 (FIG. 11E) between the non-parallel surface 1114 and the collet surface that faces surface 1114. The collet surface may be orthogonal to the long axis. When an axial force is applied to tulip, gap 1102 provides space so that less distally directed force is applied to the vertical surface of collet, reducing the likelihood of collet expansion and loosening. The reduction in likelihood is compared to a system that may be alike in all ways but instead having a radially extending surface 1114 that is orthogonal to the bone implant longitudinal axis LA, or compared to systems in which a gap does not exist.

The undercut in the proximal end of the bone implant recess 1112 may be described in a variety of ways. The undercut may be described as a recessed collet receiving region 1112 in the proximal region of the implant that includes a radially extending surface (e.g., 1114) that is disposed at an angle less than ninety degrees relative to a bone implant longitudinal axis, the angle measured distally relative to the radially extending surface, as shown as angle alpha in FIG. 11D. In FIG. 11D, the angle is also shown relative to axially extending surface 1118, but axially extending surface 1118 need not be flat as is shown, but instead may be curvilinear. In any embodiments herein, however, surface 1114 or an extension thereof may form an angle with a long axis of the implant or an axis that is parallel with the long axis, which may be the same angle alpha in both cases.

The undercuts herein may also be described and claimed functionally herein, such as the radially extending surface angled so as to reduce the likelihood of a distal end of the collet expanding and becoming loose in response to an axial force (e.g., solely proximally directed), compared to a system alike in all ways but instead having a radially extending surface that is orthogonal to the bone implant longitudinal axis.

The undercuts herein may be described as including a proximal region that includes a radially recessed collet receiving region or area including a radially extending surface that is disposed at an angle less than ninety degrees relative to the long axis. The undercuts herein may be described as including a proximal region that includes a radially recessed collet receiving area that includes a distal axially extending surface (e.g., surface 1118) and a proximal axially extending surface (e.g., 1116), the distal and proximal axially extending surfaces on either side of a radially extending surface (e.g., 1114), the proximally axially extending surface disposed further radially outward from the long axis than the distal axially extending surface, an example of which is shown in FIGS. 11D and 11E.

The undercut may be considered as including radially extending surface 1114 and one or more surfaces extending therefrom, such as axially extending surface 1118 and axially extending surface 1116. In this example, the undercut includes a distal end of axially extending surface 1116 extending further distally than a proximal end of radially extending surface 1114, as is shown in FIGS. 11D and 11E.

As described herein, an axially extending surface is not necessarily parallel with a long axis of the implant, but rather may be at an angle thereto and still considered to be axially extending, or may even be curvilinear and still be considered to be axially extending.

Figure 11A:
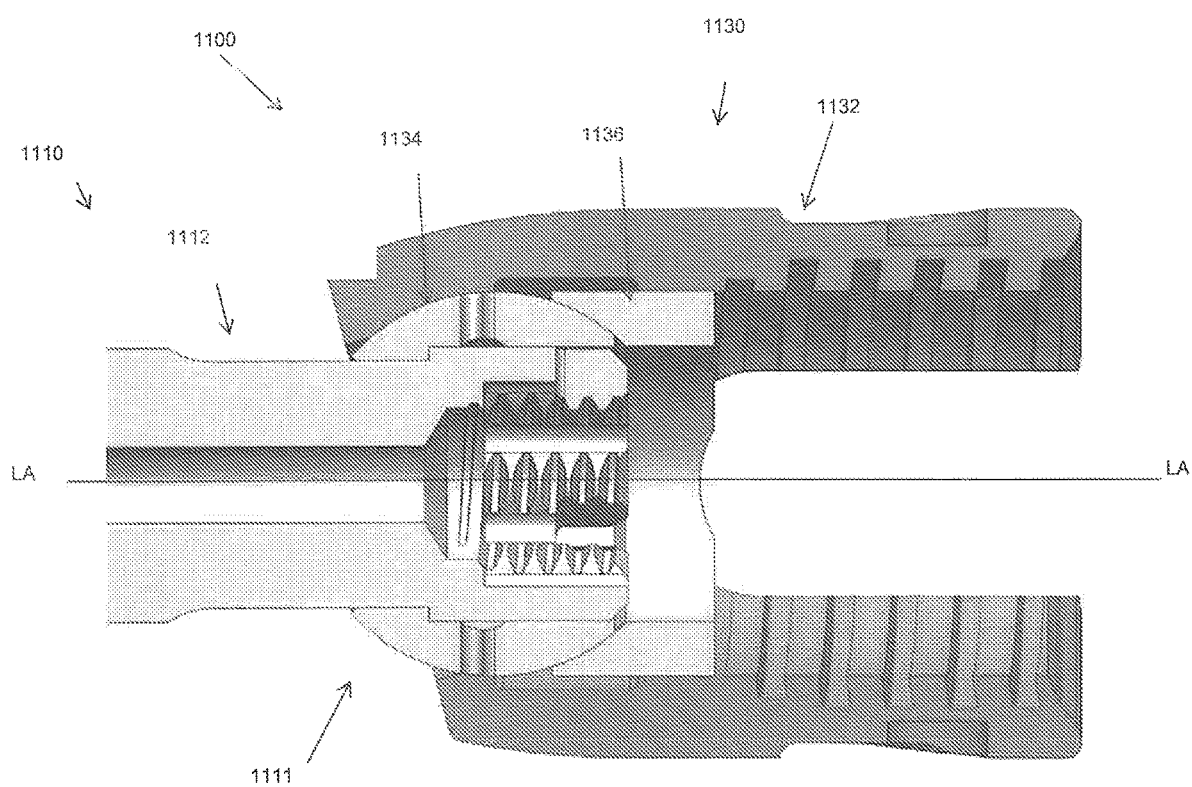
Figure 11B:
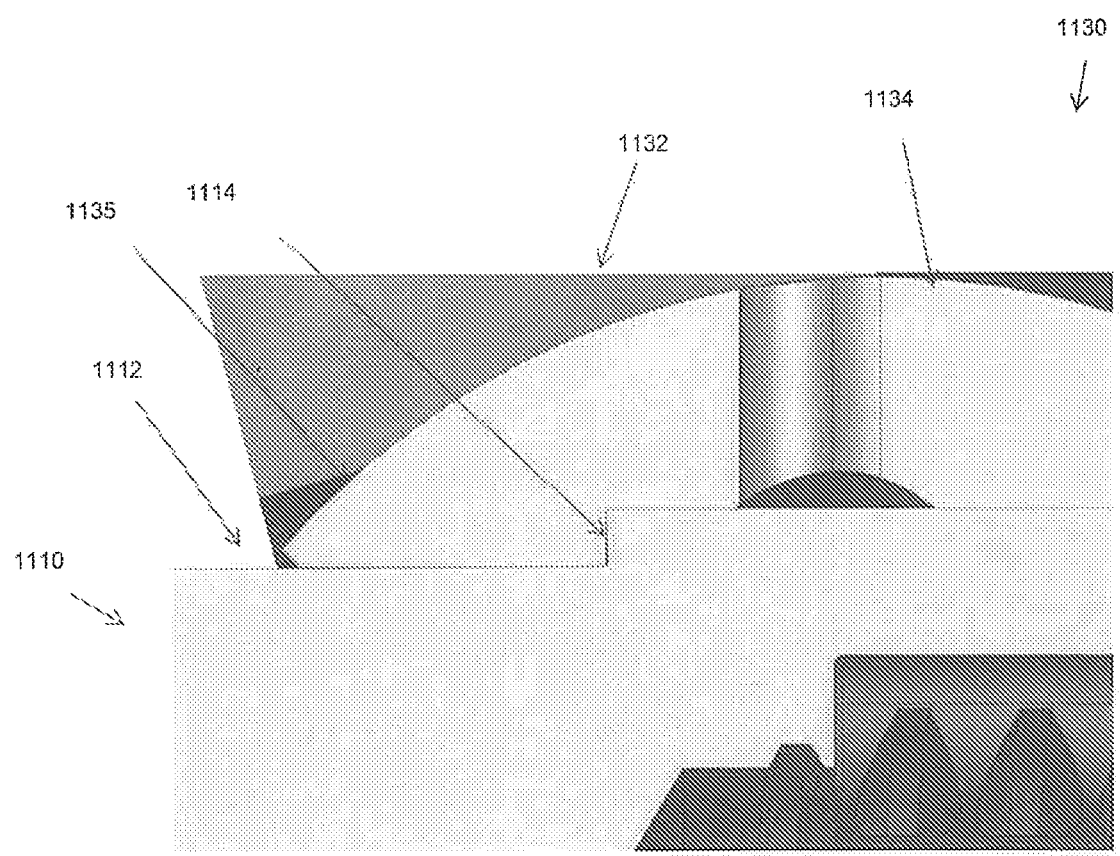

Collet 1134 or any collet herein may include common collet features, such as linear slits or slots formed therethrough that allow for expansion and collapse of a distal end of the collet. This may allow the collet to be advanced over the proximal end of the implant, causing collet expansion. In some embodiments, the proximal end of the implant may facilitate collet expansion, such as by having chamfered surface 1120 (FIG. 11C), which can help expand the distal end of the collet as it is slid distally over the proximal end of the implant. Once the collet implant interface region 1135 (FIG. 11B) is advanced distally to the recessed region 1112, the collet implant interface region 1135 collapses into the recess 1112 due to the collapsibility of the collet distal end due to the slits/slots. Snapping or collapsing into place into the recessed region 1112 secures the collet in place relative to the proximal region 1111 of the implant, as is shown in FIGS. 11A, 11B, and 11E. Tulip 1132 may still be moved relative to the collet 1134 until a set screw is threaded into the tulip (internal threads shown in FIG. 11A) to secure the rod in place (not shown in FIGS. 11A-11I), but any rod herein may be positioned through the tulip side openings.

Collet implant interface region 1135 shown in FIG. 11B is an example of a radially inward protruding implant interface region of the collet, and is shown disposed and interfaced with recessed region 1112 of collet 1134. The radially extending surface of the collet 1134 that is shown in FIG. 11E that is facing implant surface 1114 may be orthogonal to a central axis of the collet. In other embodiments it may be disposed at an angle relative to a long axis.

In some embodiments, the radially extending surface of the implant interface region of the collet (e.g., as shown in FIG. 11E) is orthogonal to a longitudinal axis of the collet.

In some embodiments, the radially extending surface of the recessed collet receiving region of the implant is disposed at an angle (e.g., angle alpha in FIG. 11D) that is less than 85 degrees relative to the longitudinal axis of the implant. In some embodiments, the angle alpha may be greater than 45 degrees relative to the longitudinal axis of the implant. In some embodiments, the angle alpha is greater than 75 degrees relative to the longitudinal axis of the implant. In some embodiments, the angle is from seventy degrees to eighty-nine degrees relative to the longitudinal axis of the implant.

In some embodiments, the recessed collet receiving region (such as region 1112) has a depth from 0.1 mm to 2.0 mm relative to an outer dimension of the implant axially adjacent to the recessed region 1112.

In any of the embodiments herein the bone implant proximal region may be void of an external thread, such as is shown in the example in FIGS. 11A-11J.

In some embodiments, the recessed collet receiving region of the implant has an annular configuration about the bone implant, such as is shown in FIG. 11C.

Even if not shown herein, a collet of any of the systems herein may have a partially spherical configuration, and the tulip may have a corresponding inner surface. The collet and tulips surfaces may be together sized and configured to interface with each other when the collet is disposed within the tulip. The tulip inner surface and the collet outer surface may be both sized and configured to cause the tulip to be movable relative to the collet in a movable state, such as in the embodiment in FIGS. 11A-11J.

Any of the tulip assemblies or rod coupling assemblies herein may include further a saddle sized and configured to be positioned within the tulip and at least partially proximal to the collet. The saddles herein may have a distal region with an inner curved surface shaped to mate with a curved proximal region of the collect. The saddles herein may have a proximal end with a recessed region having a configuration shaped to interface with an outer surface of the elongate rod (e.g., as shown in the embodiment in FIGS. 11A-11J).

Any of the collets herein may have one or more openings formed therein. Threaded a set screw into the tulip in FIG. 11A applies a force to a rod (not shown) and thereby to the saddle. This, along with the collet/tulip interface, causes compression of the collet around the implant proximal end. Once the tulip is at the desired angle, the set screw can be advanced as set forth herein and essentially stabilize the tulip relative to the rod and to the implant.

While exemplary bone implants are shown herein, bone implants that may be part of the rod coupling assemblies herein may be configured and sized as a wide variety of bone implants. For example, bone implants herein may be threaded along at least a portion of their lengths, or they may be non-threaded. The bone implants herein may be configured to be advanced into one or more of an ilium, or a sacrum or other vertebrae.

One aspect of this disclosure is a bone implant, with or without a tulip assembly associated therewith. The bone implant may have an elongate body with a long axis and a proximal region, wherein the proximal region is sized and configured to be coupled within a collet of a tulip assembly. The proximal region of the implant may include a radially recessed collet receiving region (e.g., region 1112) including a radially extending surface (e.g., surface 1114) that is disposed at an angle less than ninety degrees relative to the implant long (or central) axis. The collet receiving region of the implant may also include a distal axially extending surface and a proximal axially extending surface, the distal and proximal axially extending surfaces on either side of the radially extending surface, wherein the proximally axially extending surface is disposed further radially outward from the long or central axis than the distal axially extending surface.

The proximal ends of any bone implants herein may have a chamfered configuration, such as is labeled as 1120 in the example shown in FIG. 11C.

A distally axially extending surface (e.g., surface 1118) may be at an angle from zero to twenty-five degrees, inclusive, relative to the implant long axis.

Any of the bone implants herein may include a proximal region that has an inner lumen with an inner thread, such as is shown in FIG. 11A. In some embodiments that are coupled as modular tulip assemblies, the inner thread may be sized and configured to interface with an outer thread on a guide rod that may facilitate advancement of a modular tulip assembly including a collet over the proximal region of the elongate body.

Any of the undercut ledge configurations herein may also be described similarly to a cliff with an upper surface, at least a portion of which extends distally relative to a radially extending wall portion of the cliff.

Tulips assemblies herein may be coupled to the implant prior to insertion, or they may be modular and coupled to the implant after the implant is at least partially implanted into bone. Whether modular of coupled to the implant prior to bone implant implantation, the tulip assemblies may include any of the features of any tulip assemblies herein.

The tulips herein may include any suitable features common to existing tulips. FIGS. 11A-11J illustrate an exemplary tulip with first and second side openings that are sized and configured to receive an elongate rod therethrough. FIGS. 11A-11J illustrate an exemplary tulip assembly with a collet that includes a radially inward protruding implant interface region (e.g., region 1135), the protruding implant interface region including a radially extending surface disposed at an angle relative to a collet longitudinal axis and an axially extending surface that meets the radially extending surface, as shown. The radially inward protrusion facilitates the collapse of the collet distal end towards the recessed region of the bone implant proximal region as the collet is advanced over the proximal region of the bone implant (or the implant is moved axially within the collet). Any of the tulip assemblies herein may include a saddle that is sized to be disposed within the tulip and at least partially proximal to the collet. Any saddle may have a distal region with an inner curved surface shaped to mate with a curved proximal region of the collect. Any saddles herein may have a proximal end with a recessed region with a configuration shaped to interface with the elongate rod.

Any of the tulip assemblies herein may include a collet having one or more openings or slits therein that allow and cause the collet to apply a radially inward clamping force in response to forces applied to the collet from the tulip and the saddle.

Any of the tulip assemblies herein may include a radially inward protrusion (e.g., implant interface region 1135) that has a height from 0.1 mm to 2.0 mm, the dimension of which may be considered to be substantially the same as a depth as any of the recessed implant regions herein.

Any of the collets herein may include a protrusion that includes a radially extending surface that is orthogonal to a collet long axis, such as is shown in exemplary FIG. 11E.

Additional disclosure of system components and features disclosed in U.S. Pat. Nos. 8,845,693 and 9,655,656 may be relevant to disclosure herein, and the entire disclosures thereof are incorporated by reference herein for all purposes.

FIGS. 11F-11J illustrate merely exemplary method steps and delivery tools for coupling a modular tulip assembly to an implant.

Figure 11F:
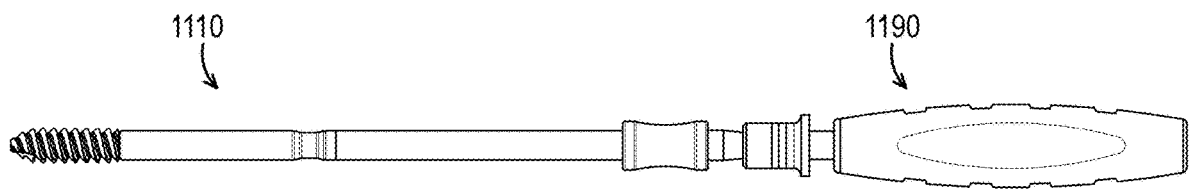
Figure 11G:
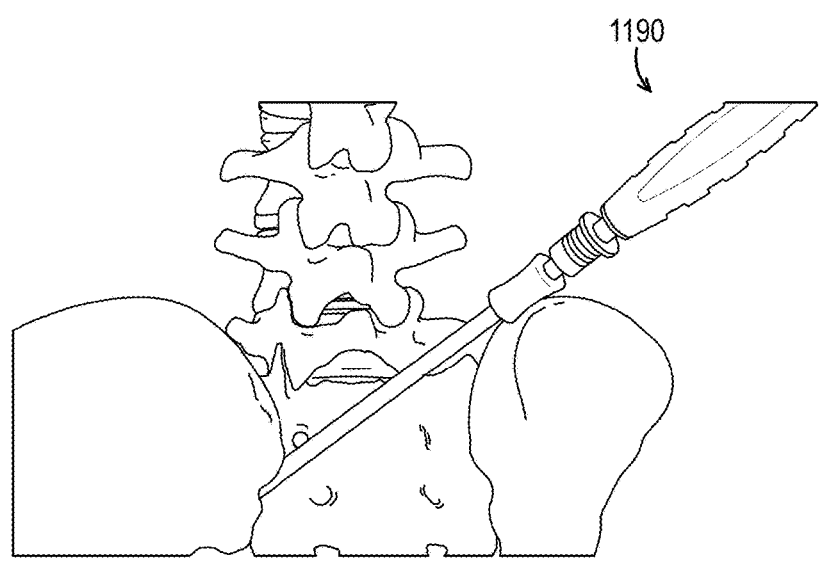
Figure 11H:
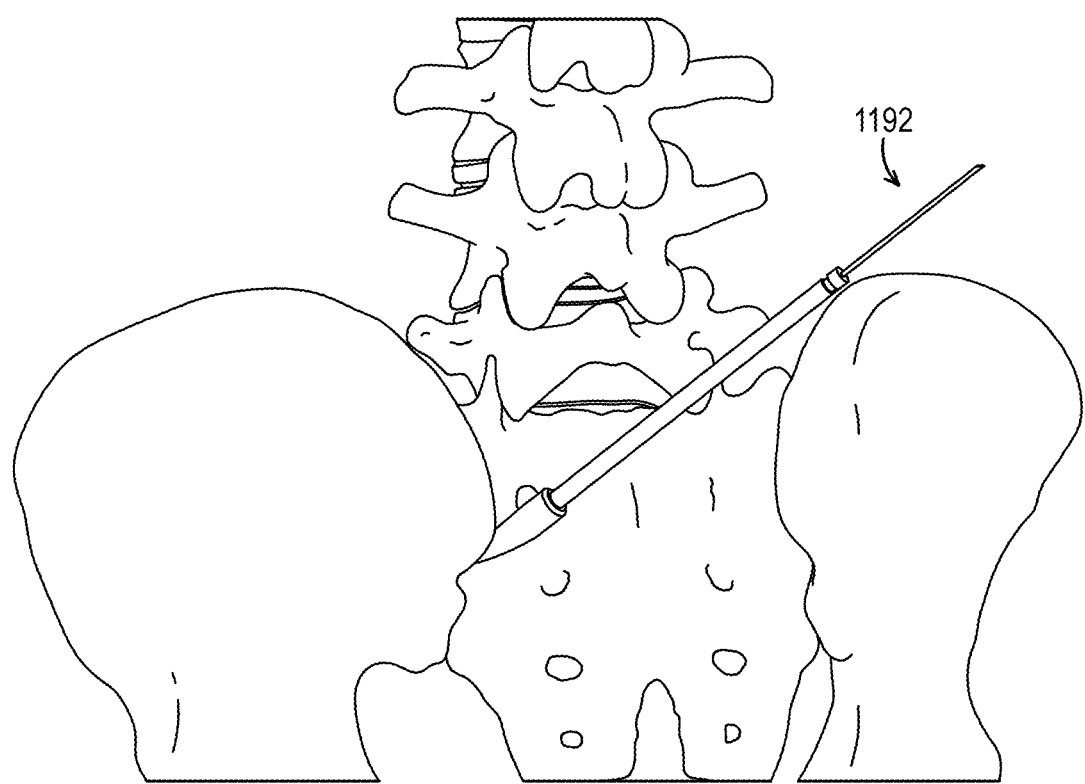
Figure 11I:
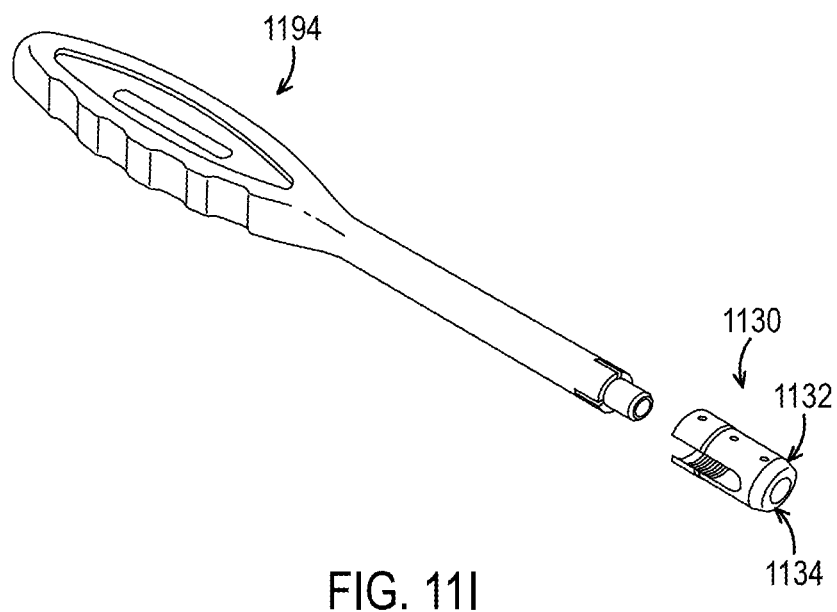
Figure 11J:
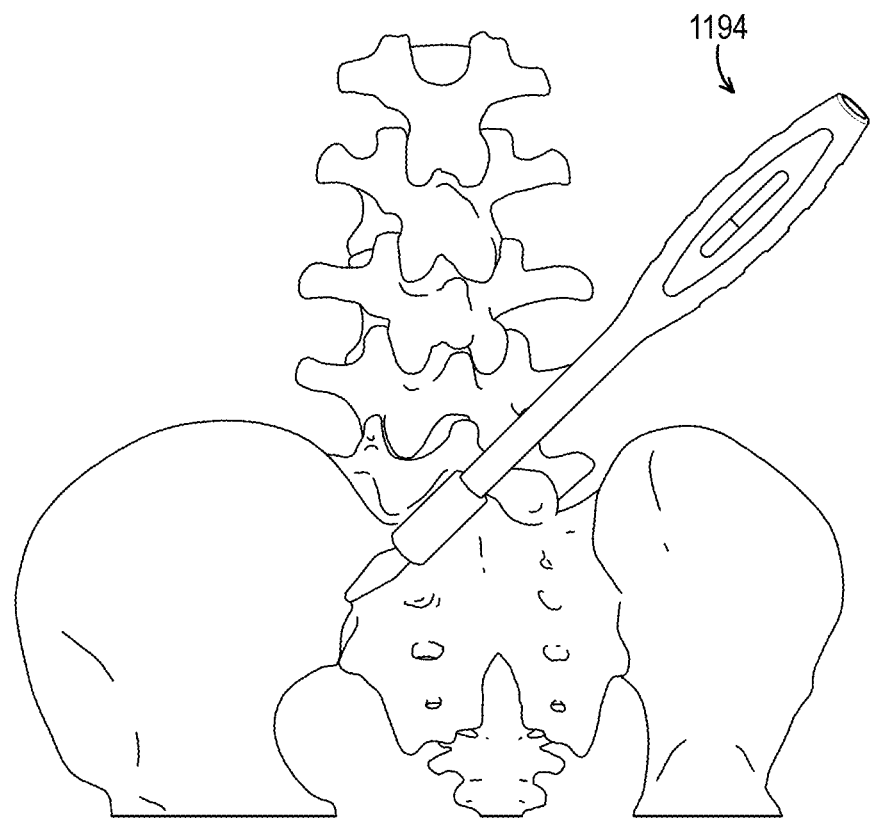

FIGS. 11F and 11G illustrate implant 1110 being implanted using implant delivery tool 1190. After removing implant delivery tool 1190, guide rod 1192 is coupled to the proximal region of the bone implant such that the guide rod extends proximally from the bone implant, as shown in FIG. 11H. After removing the guide rod, a tulip delivery tool 1194 that is coupled to a tulip assembly 1130 is used to advance the tulip assembly over the guide rod, as shown in FIGS. 11I and 11J. The method may further include advance the collet against a proximal end of the bone implant proximal region and causing a distal end of the collet to expand as it is advanced over the bone implant proximal region. The method may further include continuing to advance the collet over the bone implant proximal region until a radially inward protrusion of the collet moves radially inward into a recessed region of the bone implant, the recessed region of the bone implant having a proximal end with an undercut ledge configuration.

In some embodiments the bone implant is implanted with the tulip assembly already coupled thereto.

What is claimed is:

1. A rod coupling system including a bone implant and a tulip assembly for securing a rod relative to the bone implant, the system including:
    a bone implant having a proximal region spaced from a distal region, the proximal region sized and configured to interface with a tulip assembly, the tulip assembly including a tulip and a collet sized and configured to be disposed at least partially within the tulip,
        the bone implant proximal region including a radially recessed collet receiving region configured and sized to receive therein a radially inward protruding implant interface region of the collet, the recessed collet receiving region including a radially extending surface that is disposed at an angle less than ninety degrees relative to a bone implant longitudinal axis, the angle measured distally relative to the radially extending surface,
    a tulip assembly having an opening therethrough sized and configured to receive a stabilizing rod therethrough,
        the implant interface region of the collet including a radially extending surface disposed at an angle relative to a collet longitudinal axis, the radially extending surface of the implant interface region positioned to be facing the radially extending surface of the recessed collet receiving region when the implant interface region is interfaced with the recessed collet receiving region and such that a gap exists between the radially extending surface of the implant interface region and the radially extending surface of the recessed collet receiving region.

2. The system of claim 1, wherein the radially extending surface of the implant interface region of the collet is orthogonal to the longitudinal axis of the collet.

3. The system of claim 1, wherein the radially extending surface of the recessed collet receiving region is disposed at an angle less than 85 degrees relative to the longitudinal axis of the implant.

4. The system of claim 1, wherein the radially extending surface of the recessed collet receiving region is disposed at an angle greater than 45 degrees relative to the longitudinal axis of the implant.

5. The system of claim 1, wherein the radially extending surface of the recessed collet receiving region is disposed at an angle greater than 75 degrees relative to the longitudinal axis of the implant.

6. The system of claim 1, wherein the radially extending surface of the recessed collet receiving region is disposed at an angle from 70 degrees to 89 degrees relative to the longitudinal axis of the implant.

7. The system of claim 1, wherein the tulip assembly is modular and is adapted to be delivered separately from the bone implant and movably secured to the bone implant after the bone implant has been at least partially implanted within bone.

8. The system of claim 7, wherein the implant proximal region includes an internal thread sized and configured to receive therein a threaded guide rod, the tulip assembly adapted to be advanced over the threaded guide rod and advanced over the proximal region of the implant to movably secure the tulip assembly and the bone implant.

9. The system of claim 1, wherein the bone implant proximal region includes a chamfered proximal end to facilitate expansion of a collet distal end as the collet is advanced over the chamfered proximal end, the recessed collet receiving region causing the radially inward protruding implant interface region of the collet to move radially inward into the recessed collet receiving region as the collet is advanced distally over the bone implant proximal region.

10. The system of claim 1, wherein the bone implant proximal region is configured to facilitate opening of a collet distal end as the collet is advanced over the proximal region, the recessed collet receiving region causing the radially inward protruding implant interface region of the collet to revert towards an at-rest state into the recessed collet receiving region as the collet is advanced further over the bone implant.

11. The system of claim 1, wherein the recessed collet receiving region has a depth from 0.1 mm to 2.0 mm.

12. The system of claim 1, wherein the bone implant proximal region is void of an external thread.

13. The system of claim 1, wherein the bone implant proximal region has an outermost sleeve surface that is sized and configured to extend over at least a portion of a distal end of the tulip.

14. The system of claim 13, wherein the outermost sleeve surface is a surface of an outer implant sleeve, the outer implant sleeve disposed about an implant inner shank.

15. The system of claim 1, wherein the recessed collet receiving region has an annular configuration about the bone implant.

16. A rod coupling system including a bone implant and a tulip assembly for securing a rod relative to the bone implant, the system including:
a bone implant having a proximal region spaced from a distal region, the proximal region configured to interface with a tulip assembly, the tulip assembly including a tulip and a collet sized and configured to be disposed at least partially within the tulip,
the bone implant proximal region including a recessed collet receiving region configured and sized to receive therein a radially inward protruding implant interface region of the collet,
the recessed collet receiving region including a radially extending surface that is disposed at an angle less than ninety degrees relative to a bone implant longitudinal axis, the angle measured distally relative to the radially extending surface, the radially extending surface angled,
a tulip assembly having an opening therethrough configured to receive a rod therethrough,
the implant interface region of the collet including a radially extending surface disposed at an angle relative to a collet longitudinal axis, the radially extending surface of the implant interface region positioned to be facing the radially extending surface of the recessed collet receiving region when the bone implant interface region is interfaced with the recessed collet receiving region and such that a gap exists between the radially extending surface of the implant interface region and the radially extending surface of the recessed collet receiving region.

17. A rod coupling system including a bone implant and a tulip assembly for securing a rod relative to the bone implant, the system including:
a bone implant having a proximal region spaced from a distal region, the proximal region configured to interface with a tulip assembly that includes a collet and a tulip,
the bone implant proximal region including a recessed collet receiving region configured and sized to receive therein a bone implant interface region of the collet, the collet receiving region including a recessed axially extending surface and a radially extending surface that is disposed at an angle less than ninety degrees relative to a bone implant longitudinal axis, the recessed axially extending surface and the radially extending surface meeting one another,
a tulip assembly having an opening therethrough configured to receive a rod therethrough, the tulip assembly including a collet and saddle sized to be disposed at least partially within the tulip,
the collet having a partially spherical configuration, the tulip having an inner surface and the collet having an outer surface that are sized and configured to interface with each other when the collet is disposed within the tulip, the tulip inner surface and the collet outer surface both configured to cause the tulip to be movable relative to the collet in a movable state,
the collet including an implant interface region that includes a radially extending surface disposed at an angle relative to a collet longitudinal axis, the radially extending surface of the implant interface region positioned to be facing the radially extending surface of the recessed collet receiving region when the bone implant interface region is interfaced with the recessed collet receiving region and such that a gap exists between the radially extending surface of the implant interface region and the radially extending surface of the recessed collet receiving region,
the saddle sized to be disposed within the tulip and at least partially proximal to the collet, the saddle having a distal region with an inner curved surface shaped to mate with a curved proximal region of the collect, the saddle having a proximal end with a recessed region having a configuration shaped to interface with the rod,
the collet having one or more openings therein that cause the collet to apply a radially inward clamping force in response to force applied to the collet from the tulip and the saddle, a set screw sized and configured to be threaded into the tulip and apply a force to the rod and secure a position of the tulip relative to the bone implant.

\* \* \* \* \*